United States Patent
Asokan et al.

(10) Patent No.: US 11,718,862 B2
(45) Date of Patent: *Aug. 8, 2023

(54) METHODS AND COMPOSITIONS FOR CIRCULAR RNA MOLECULES

(71) Applicant: The University of North Carolina at Chapel Hill, Chapel Hill, NC (US)

(72) Inventors: Aravind Asokan, Chapel Hill, NC (US); Erin Borchardt, Naperville, IL (US); Rita Meganck, Raleigh, NC (US); William F. Marzluff, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/506,089

(22) Filed: Oct. 20, 2021

(65) Prior Publication Data

US 2022/0090137 A1 Mar. 24, 2022

Related U.S. Application Data

(63) Continuation of application No. 16/761,876, filed as application No. PCT/US2018/059652 on Nov. 7, 2018.

(60) Provisional application No. 62/582,796, filed on Nov. 7, 2017.

(51) Int. Cl.
| | |
|---|---|
| C07H 21/04 | (2006.01) |
| C12N 15/00 | (2006.01) |
| C12N 15/63 | (2006.01) |
| C12N 15/86 | (2006.01) |
| A01K 67/00 | (2006.01) |

(52) U.S. Cl.
CPC .... *C12N 15/86* (2013.01); *C12N 2750/14122* (2013.01); *C12N 2750/14143* (2013.01); *C12N 2840/203* (2013.01)

(58) Field of Classification Search
CPC .......... C12N 15/86; C12N 2750/14122; C12N 2750/14143; C12N 2840/203
See application file for complete search history.

(56) References Cited

U.S. PATENT DOCUMENTS

| | | | |
|---|---|---|---|
| 9,822,378 B2 | 11/2017 | Kruse | |
| 2013/0310443 A1* | 11/2013 | Srivastava | A61P 3/10 435/320.1 |
| 2019/0345503 A1* | 11/2019 | Chang | A61K 39/39 |

FOREIGN PATENT DOCUMENTS

| | | |
|---|---|---|
| WO | 2014186334 A1 | 11/2014 |
| WO | 2016172008 A1 | 10/2016 |
| WO | 2016172155 A1 | 10/2016 |

OTHER PUBLICATIONS

Meganck et al. "Engineering highly efficient backsplicing and translation of synthetic circRNAs" Molecular Therapy Nucleic Acids, 23:821-834 (2021).
Ashwal-Fluss et al. "circRNA Biogenesis Competes with Pre-mRNA Splicing" Molecular Cell, 56:55-66 (2014).
Atchison et al. "Adenovirus-Associated Defective Virus Particles" Science, 149(3685):754-756 (1965).
Bartel et al. "Directed evolution of novel adeno-associated viruses for therapeutic gene delivery" Gene Therapy, 19:694-700 (2012).
Borchardt et al. "Inducing circular RNA formation using the CRISPR endoribonuclease Csy4" RNA, 23(5):619-627 (2017).
Buller et al. "Herpes Simplex Virus Types 1 and 2 Completely Help Adenovirus-Associated Virus Replication" Journal of Virology, 40(1):241-247 (1981).
Capel et al. "Circular Transcripts of the Testis-Determining Gene Sry in Adult Mouse Testis" Cell, 73:1019-1030 (1993).
Chen et al. "Initiation of Protein Synthesis by the Eukaryotic Translational Apparatus on Circular RNAs" Science, 268(5209):415-417 (1995).
Chen, Ling-Ling "The biogenesis and emerging roles of circular RNAs" Nature Reviews Molecular Cell Biology, 17:205-211 (2016) (Abstract only).
Cocquerelle et al. "Mis-splicing yields circular RNA molecules" The FASEB Journal, 7(1):155-160 (1993).
Conn et al. "The RNA Binding Protein Quaking Regulates Formation of circRNAs" Cell, 160(6):1125-1134 (2015).
Danan et al. "Transcriptome-wide discovery of circular RNAs in Archaea" Nucleic Acids Research, 40(7):3131-3142 (2012).
Ebbesen et al. "Circular RNAs: Identification, biogenesis and function" Biochimica et Biophysica Acta (BBA)—Gene Regulatory Mechanisms, 1859(1):163-168 (2016) (Abstract only).
Enuka et al. "Circular RNAs are long-lived and display only minimal early alterations in response to a growth factor" Nucleic Acids Research, 44(3):1370-1383 (2016).
Gao et al. "CIRI: an efficient and unbiased algorithm for de novo circular RNA identification" Genome Biology, 16(4):1-16 (2015).
Gao et al. "Clades of Adeno-Associated Viruses Are Widely Disseminated in Human Tissues" Journal of Virology, 78(12):6381-6388 (2004).
Gao et al. "Novel adeno-associated viruses from rhesus monkeys as vectors for human gene therapy" Proceedings of the National Academy of Sciences USA, 99(18):11854-11859 (2002).
Glazar et al. "circBase: a database for circular RNAs" RNA, 20:1666-1670 (2014).

(Continued)

*Primary Examiner* — Quang Nguyen
(74) *Attorney, Agent, or Firm* — Myers Bigel, P.A.

(57) ABSTRACT

This invention is directed to AAV compositions for circular RNA expression and methods of expressing covalently closed, circular RNA.

28 Claims, 41 Drawing Sheets

Specification includes a Sequence Listing.

(56) References Cited

OTHER PUBLICATIONS

Guo et al. "Expanded identification and characterization of mammalian circular RNAs" Genome Biology, 15(409):1-14 (2014).
Hansen et al. "Natural RNA circles function as efficient microRNA sponges" Nature, 495:384-388 (2013).
Hauswirth et al. "Origin and termination of adeno-associated virus DNA replication" Virology, 78(2):488-499 (1977) (Abstract only).
Jeck et al. "Circular RNAs are abundant, conserved, and associated with ALU repeats" RNA, 19(2):141-157 (2013).
Jost et al. "Functional sequestration of microRNA-122 from Hepatitis C Virus by circular RNA sponges" RNA Biology, 15(8):1032-1039 (2018).
Kotin et al. "Site-specific integration by adeno-associated virus" Proceedings of the National Academy of Sciences USA, 87:2211-2215 (1990).
Legnini et al. "Circ-ZNF609 Is a Circular RNA that Can Be Translated and Functions in Myogenesis" Molecular Cell, 66(1):22-37 (2017).
Liang et al. "Short intronic repeat sequences facilitate circular RNA production" Genes & Development, 28(20):2233-2247 (2014).
Liang et al. "The Output of Protein-Coding Genes Shifts to Circular RNAs When the Pre-mRNA Processing Machinery Is Limiting" Molecular Cell, 68(5):940-954 (2017).
Licursi et al. "In vitro and in vivo comparison of viral and cellular internal ribosome entry sites for bicistronic vector expression" Gene Therapy, 18:631-636 (2011).
Meganck et al. "Tissue-Dependent Expression and Translation of Circular RNAs with Recombinant AAV Vectors In Vivo" Molecular Therapy: Nucleic Acids, 13:89-98 (2018).
Memczak et al. "Circular RNAs are a large class of animal RNAs with regulatory potency" Nature, 495:333-338 (2013).
Mingozzi et al. "Immune responses to AAV vectors: overcoming barriers to successful gene" Blood, 122(1):23-36 (2013).
Nakai et al. "Extrachromosomal Recombinant Adeno-Associated Virus Vector Genomes Are Primarily Responsible for Stable Liver Transduction In Vivo" Journal of Virology, 75(15):6969-6976 (2001).
Nigro et al. "Scrambled exons" Cell, 64(3):607-613 (1991) (Abstract only).
Pamudurti et al. "Translation of CircRNAs" Molecular Cell, 66(1):9-21 (2017).
Rybak-Wolf et al. "Circular RNAs in the Mammalian Brain Are Highly Abundant, Conserved, and Dynamically Expressed" Molecular Cell, 58(5):870-885 (2015).
Salzman et al. "Circular RNAs Are the Predominant Transcript Isoform from Hundreds of Human Genes in Diverse Cell Types" PLoS One, 7(2):e30733 (2012).
Samulski et al. "AAV-Mediated Gene Therapy for Research and Therapeutic Purposes" Annual Review of Virology, 1:427-451 (2014).
Shen et al. "Engraftment of a Galactose Receptor Footprint onto Adeno-associated Viral Capsids Improves Transduction Efficiency" Journal of Biological Chemistry, 288(40):28814-28823 (2013).
Srivastava et al. "Nucleotide Sequence and Organization of the Adeno-Associated Virus 2 Genome" Journal of Virology, 45(2):555-564 (1983).
Wang et al. "Circular RNA Is Expressed across the Eukaryotic Tree of Life" PLoS One, 9(3):e90859 (2014).
Wang et al. "Efficient backsplicing produces translatable circular mRNAs" RNA, 21(2):172-179 (2015).
Xiao et al. "A novel 165-base-pair terminal repeat sequence is the sole cis requirement for the adeno-associated virus life cycle" Journal of Virology, 71(2):941-948 (1997).
Yang et al. "Extensive translation of circular RNAs driven by N6-methyladenosine" Cell Research, 27:626-641 (2017).
You et al. "Neural circular RNAs are derived from synaptic genes and regulated by development and plasticity" Nature Neuroscience, 18(4):603-610 (2015).
Zhang et al. "Complementary Sequence-Mediated Exon Circularization" Cell, 159(1):134-147 (2014).
Zheng et al. "Circular RNA profiling reveals an abundant circHIPK3 that regulates cell growth by sponging multiple miRNAs" Nature Communications, 7(11215):1-13 (2016).
Zincarelli et al. "Analysis of AAV Serotypes 1-9 Mediated Gene Expression and Tropism in Mice After Systemic Injection" Molecular Therapy, 16(6):1073-1080 (2008).
Takara Bio Company "Transgenesis by Adeno-associated virus (AAV) vectors" English translation of Product Information (Jun. 24, 2017) https://web.archive.org/web/20170614141522/http://catalog.takara-bio.co.jp/product/basic_info.php?.

* cited by examiner

HIPK3
GCCTCAGCCTCTCAAAGTGCTAGGATTACAGGGATCTATAC<u>TTTTCTTTTGAGGGAAAATGT
TGGCACCGTTTCTAGGGCATATTGGCCATTTCAGCTTCTCAGTAAATATTTGTTAAGTAATT
AAATGCACTTGATTCTTTATTCTTAGCCTTTTAACGCAATACTCAGAATAGCTGAAGCACCA
ATTAACTGAAATGGAGATATTATAAAGATAGTTATCTTCTCCAAGGGAAAAAATCATCTTCA
TGGAAATTAATTACTTTTT</u>TACAAATTGTGAATTTGACCCTTAAGAGTTTTCTTCCTGATAT
TTAAAATTGAAAAAAAAATTGTTGACATTAATATTTCTTCTTTCCTTTTTTTTCTTTTCCTT
TTTTTTTTTTTTTTGCAG

GTAGGTAACAACTCCATACTTTTTGGTTGTTTATTAATGTGAAATTTCTGCTAAATGAAATA
CTTTTGTGTGTGTTTGTGGTAGAAGAGACCACTTCAGTTAAATAAGGAAATCAAGAGAGGAT
CAATTTAGGTTCGTTTTAAAGAGATTAAAAAAAATCAAGACATAAAATCTACCCAAGCAGGA
TAGAAATCTCCACTGCAAAGTTCCATGCCAAAGACATCTGGTTATTTTTATTTTTAATGGAA
GACTTGAAGGAATGATAGGTGATTAATAATGATCAAACAGAAGTCTTTAAATGTTGGAAAGT
ATTTACATTAATCTTTGTATATATCATTGGGCATTTTAGCACTTGAGAGAAATAGTTTATTA
AGATATAATCAATCATATGTAACTGAACATTTAGAAAAATTATATACAGGTTTGAGTAGCC
CTTATCTGAAACTTTTGGGGCCAGAAGTGTTTTGGATTCCAGATTTTTCCGGATTTTGGAAT
ATTTGCACTGCCAACTAGTTAAGCACCCCCAAATTTGAAAATTCGTTTCCTTTGAGTGTCAT
GTCAATGCCCAAAAAGTTTCAGATATTTGGATTTGAGATGCTCAACCTGTATAAGGATTCAG
AAAGTTATTCTGATTAATGATTTAAGATTCAGATATACAA**TAATCCCAGCAACTTGGGAGG
CTGAGG**CAGGAGAATCACTTGAACCCAGGAGATGGAGGTTGCAGTGAGCCGAGATCATGCCA
TTGCACTCCA

*FIG. 14A*

ZKSCAN1
AGTGACAGTGGAGATTGTACAGTTTTTTCCTCGATTTGTCAGGATTTTTTTTTTTTGACGG
AGTTTAACTTCTTGTCTCCCAGGTAGGAAGTGCAGTGGCGTAATCTCGGCTCACTACAACCT
CCACCTCCTGGGTTCAAGCGTTTCTCCTGCCTCAGCTTTCCGAGTAGCTGGGATTACAGGCG
CCTGCCACCATGCCCTGCTGACTTTTGTATTTTTAGTAGAGACGGGGTTTCACCATGTTGGC
CAGGCTGGTCTTGAACTCCTGACCGCAGGCGATTGGCCTGCCTCGGCCTCCCAAAGTGCTGA
GATTACAGGCGTGAGCCACCACCCCCGGCCTCAGGAGCGTTCTGATAGTGCCTCGA<u>TGTGCT</u>
<u>GCCTCCTATAAAGTGTTAGCAGC</u>ACAGATCACTTTTTGTAAAGGTACGTACTAATGACTTTT
TTTTTATACTTCAG

<u>GTAAGAAGCAAGGTTTCATTTAGGGGAAGGGAAATGATTCAGGACGAGAGTCTTTGTGCTGC</u>
<u>TGAGTGCCTGTGATGAAGAAGCATGTTAGTCCTGGGCAACGTAGCGAGACCCCATCTCTACA</u>
<u>AAAAATAGAAAAATTAGCCAGGTATAGTGGCGCACACCTGTGATTCCAGCTACGCAGGAGGC</u>
<u>TGAGGTGGGAGGATTGCTTGAGCCCAGGAGGTTGAGGCTGCAGTGAGCTGTAATCATGCCAC</u>
<u>TACTCCAACCTGGGCAACACAGCAAGGACCCTGTCTCAAAAGCTACTTACAGAAAAGAATTA</u>
<u>GGCTCG</u>GCACGGTAGCTCACACCTGTAATCCCAGCACTTTGGGAGGCTGAGGCGGGCAGATC
ACTTGAGGTCAGGAGTTTGAGACCAGCCTGGCCAACATGGTGAAACCTTGTCTCTACTAAAA
ATATGAAAATTAGCCAGGCATGGTGGCACATTCCTGTAATCCCAGCTACTCGGGAGGCTGAG
GCAGGAGAATCACTTGAACCCAGGAGGTGGAGGTTGCAGTAAGCCGAGATCGTACCACTGTG
CTCTAGCCTTGGTGACAGAGCGAGACTGTCTTAAAAAAAAAAAAAAAAAAAAAGAATTAAT
TAAAAATTTAAAAAAAATGAAAAAAGCTGCATGCTTGTTTTTGTTTTTAGTTATTCTAC
ATTGTTGTCATTATTACCAAATATTGGGGAAAATACAACTTACAGACCAATCTCAGGAGTTA
AATGTTACTACGAAGGCAAATGAACTATGCGTAATGAACCTGGTAGGCATTA

*FIG. 14B*

EPHB4

**CCAGCTACTCAGGAGGCTGAGGCAGAAGAATCATTTTAACCCGGGAGGCGGAGATTGCAGTG
AGCCAAGATCGCGCCACTGCGCTCCAGGCCTGGGTGACA**CCACGGA<u>GACAGGGGTTTGGGGC
TAAAAGCTATGAGCCGAGCCTCCGAGTCCAGTGGGA</u>GTTAATTCCCAGCTGACGGGGCCCTG
CCTGATTTCTCAG

GTGAGCACC<u>CTCCCTGGCTTCTGCGGCCACCCGGA</u>GTTCCCACTTACACCCAGAGGCCACTT
GGGTTAAGAAGCCAGGACAGACAGTGGGTCCCAGGTCACCTCCTCCAGCCTTTTCCTCTTGG
GCTAAGCCCTGGTCCTCTGCCTTTTCTTTTTTTTAAGACAGAGCCTCGCTC**TGTCGCCCAGG
CTGGAGTGCAGTGGCGCGATCTCGGCTCATTGCTGTCTCCACCTCCAGGGTTCAAGCGATTC
TCCTGCCTCAGTCTCCCAAGTAGCTG**GTACTATAGGCATGCACCACCATGCTGACTAATTTT
TGTATTTTTAGTAGACACAGGGTTTCACCATGTAGGCCAGGCTGGTATCAAACTCCTGACCT
CAAGTGATCTCCCCACCTCAGCCTCCCAAAGTGCTGGTATTACAGGTGTGAGGCACCACGCC
TGGCCAGCCCTCTGCCTTTAATTTTCCCTCTGGGAAAGGCTGGGCTCCTGGGACCTTCCTTT
CCCACTGCCCCATACAGCTGAAGGTTGTC

*FIG. 14C*

Laccase2

TCATTGAGAAATGACTGAGTTCCGGTGCTCTCAAGTCATTGATCTTTGTCGACTTTTATTTG
GTCTCTGTAATAACGACTTCAAAAACATTAAATTCTGTTGCGAAGCCAGTAAGCTACAAAAA
GAAAAAACAAGAGAGAATGCTATAGTCGTATAGTATAGTTTCCCGACTATCTGATACCCATT
ACTTATCTAGGGGGAATGCGAACCCAAAATTTTATCAGTTTTCTCGGATATCGATAGATATT
GGGGAATAAATTTAAATAAATAAATTTTGGGCGGGTTTAGGGCGTGGCAAAAAGTTTTTTGG
CAAATCGCTAGAAATTTACAAGACTTATAAAATTATGAAAAAATACAACAAAATTTTAAACA
CGTGGGCGTGACAGTTTTGGACGGTTTTAGGGCGTTAGAGTAGGCGAGGACAGGGTTACATC
GACTAGGCTTTGATCCTGATCAAGAATATATATACTTTATACCGCTTCCTTCTACATGTTAC
CTATTTTTCAACGAATCTAGTATACCTTTTTACTGTACGATTTATGGGTATAATAATAAGCT
AAATCGAGACTAAGTTTTATTGTTATATATATTTTTTTTATTTTATGCAG

GTAAGTATTCAAAATTCCAAAATTTTTTACTAGAAATATTCGATTTTTTAATAGGCAGTTTC
TATACTATTGTATACTATTGTAGATTCGTTGAAAAGTATGTAACAGGAAGAATAAAGCATTT
CCGACCATGTAAAGTATATATATTCTTAATAAGGATCAATAGCCGAGTCGATCTCGCCATGT
CCGTCTGTCTTATTATTTTATTACCGCCGAGACATCAGGAACTATAAAAGCTAGAAGGATGA
GTTTTAGCATACAGATTCTAGAGACAAGGACGCAGAGCAAGTTTGTTGATCCATGCTGCCAC
GCTTTAACTTTCTCAAATTGCCCAAAACTGCCATGCCCACATTTTTGAACTATTTTCGAAAT
TTTTTCATAATTGTATTACTCGTGTAAATTTCCATCAATTTGCCAAAAAACTTTTTGTCACG
CGTTAACGCCCTAAAGCCGCCAATTTGGTCACGCCCACACTATTGAACAATTATCAAATTTT
TTCTCATTTTATTCCCCAATATCTATCGATATCCCCGATTATGAAATTATTAAATTTCGCGT
TCGCATTCACACTAGCTGAGTAACGAGTATCTGATAGTTGGGGAAATCGACTTATTTTTAT
ATACAATGAAAATGAATTTAATCATATGAATATCGATTATAGCTTTTTATTTAATATGAATA
TTTATTTGGGCTTAAGGTGTAACCTCCTCGACATAAGACTCACATGGCGCAGGCACATTGAA
GACAAAATACTCATTGTCGGGTCTCGCACCCTCCAGCAGCACCTAAAATTATGTCTTCAAT
TATTGCCAACATTGGAGACACAATTAGTCTGTGGCACCTCAG

*FIG. 14D*

METHODS AND COMPOSITIONS FOR CIRCULAR RNA MOLECULES

STATEMENT OF PRIORITY

This application is a continuation application of U.S. application Ser. No. 16/761,876, filed May 6, 2020, which is a 35 U.S.C. § 371 national phase application of International Application Serial No. PCT/US2018/059652, filed Nov. 7, 2018, which claims the benefit, under 35 U.S.C. § 119(e), of U.S. Provisional Application Ser. No. 62/582,796, filed Nov. 7, 2017, the entire contents of each of which are incorporated by reference herein.

STATEMENT OF GOVERNMENT SUPPORT

This invention was made with government support under Grant Numbers HL089221, HL112761, NS099371 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-829CT_ST25.txt, 18,247 bytes in size, generated on Oct. 20, 2021, and filed via EFS-Web, is provided in lieu of a paper copy. This Sequence Listing is hereby incorporated herein by reference into the specification for its disclosures.

FIELD OF THE INVENTION

This invention is directed to compositions for circular RNA expression.

BACKGROUND OF THE INVENTION

Circular RNAs (circRNAs) are a class of noncoding RNAs in which the RNA is covalently closed to form a circle. They are found in a range of organisms, spanning from Archaea to humans. In metazoans, they are predominantly formed through a process known as direct backsplicing, in which a donor site is spliced to an upstream acceptor site (in the reverse of the normal splicing orientation). Often, the circRNA consists of an exon that has been circularized. In this way the circRNA product and the linear mRNA product can be seen to compete with each other. The ratio of circular and linear products varies on a per gene basis; for some genes, the circRNA is the predominant RNA product. Signals that affect the circularization of a given exon appear to be encoded in the surrounding intron sequences. In humans, the presence of inverted repeats (such as Alu elements) has been shown to be associated with circularization; additionally, RNA binding proteins such as Quaking (QKI) are known to be involved in the regulation of circularization.

Recent studies have shown that circRNAs are highly expressed in multiple cell and tissue types. However, the function of the majority of circRNAs is unknown. There are a few exceptions, such as ciRS-7/Cdr1as and circMbl, which are well characterized as miRNA-7 and MBL protein sponges, respectively. Some recent studies have indicated that endogenous circRNA may have coding potential; however, the translation efficiency would be quite low at best, as other studies have failed to see association of circRNA with ribosomes at appreciable levels. Regardless, circRNAs can be engineered to contain IRES (internal ribosomal entry site) sequences that drive translation of an open reading frame contained in the circRNA. An interesting property of circRNAs is their enhanced stability compared to linear isoforms, which is due to their lack of free ends. Studies have shown that circRNAs have half-lives at least 2.5 fold longer than a linear counterpart. The present invention provides circRNAs that allow for expression of proteins from a stable, persistent RNA molecule. This property makes circRNAs useful in, for example, gene delivery applications, where long-term gene expression is a key concern.

SUMMARY OF THE INVENTION

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

In one aspect, the present invention provides a nucleic acid molecule encoding a circular RNA (circRNA) that is covalently closed, wherein the nucleic acid molecule comprises: a) a gene of interest which can be transcribed into noncoding RNA or a translatable mRNA; b) intronic elements that flank the gene of interest, wherein the intronic elements are backspliced by the cellular splicing machinery to yield a circular RNA that is covalently closed; c) an internal ribosome entry site (IRES) driving translation of the translatable mRNA transcribed from the gene of interest; d) a promoter region in the 5'untranslated region (UTR) and outside of the intronic elements that flank the gene of interest; and e) a translation regulating region in the 3' UTR and outside of the intronic elements that flank the gene of interest.

The present invention further provides a method of expressing a covalently closed circular RNA molecule in a cell, comprising introducing into the cell the nucleic acid molecule of this invention, the AAV genome of this invention, the AAV capsid or particle of this invention, and/or the composition of this invention, under conditions wherein the covalently closed circular RNA molecule is transcribed.

In another embodiment, the present invention provides a method of expressing a covalently closed circular RNA molecule in a tissue specific and/or cell specific manner, comprising contacting the tissue and/or the cell with the nucleic acid molecule of this invention, the AAV genome of this invention, the AAV capsid or particle of this invention, and/or the composition of this invention, under conditions wherein the covalently closed, circular RNA molecule is expressed.

BRIEF DESCRIPTION OF THE DRAWINGS

FIGS. 14A-14D: Sequences of the left and right intron sequences for (14A) HIPK3 (Left: SEQ ID NO:15; Right: SEQ ID NO:16), (14B) ZKSCAN1 (Left: SEQ ID NO:13; Right: SEQ ID NO:14), (14C) EPHB4 (Left: SEQ ID NO:29; Right: SEQ ID NO:30), and (14D) Laccase2 (Left: SEQ ID NO:31; Right: SEQ ID NO:32). Bolded regions show the repeat sequence with identified complementarity and underlined regions show deletions that can be tolerated resulting in synthetic intronic elements. ZKSCAN1: This gene encodes a member of the Kruppel C2H2-type zinc-finger family of proteins. This encoded protein may function as a transcription factor that regulates the expression of GABA type-A receptors in the brain. Transcripts from this gene have been shown to form stable and abundant circular RNAs. Elevated expression of this gene has been observed in gastric cancer and the encoded protein may stimulate migration and invasion of human gastric cancer cells. HIPK3: (Homeodomain Interacting Protein Kinase 3) is a protein coding gene. Among its related pathways are Cellular senescence (KEGG). Gene Ontology (GO) annotations related to this gene include transferase activity, transferring phosphorus-containing groups and protein tyrosine kinase activity. EPHB4: (EPH Receptor B4) is a protein coding gene. Diseases associated with EPHB4 include Hydrops Fetalis, Nonimmune, And/Or Atrial Septal Defect and Hydrops Fetalis. Among its related pathways are ERK Signaling and Akt Signaling. Gene Ontology (GO) annotations related to this gene include transferase activity, transferring phosphorus-containing groups and protein tyrosine kinase activity. LACCASE2: a protein coding gene. Among its functions are copper ion binding, ferroxidase activity, cuticle development and ion transport in *drosophila* (fruit fly).

DETAILED DESCRIPTION OF THE INVENTION

Figure 1A:
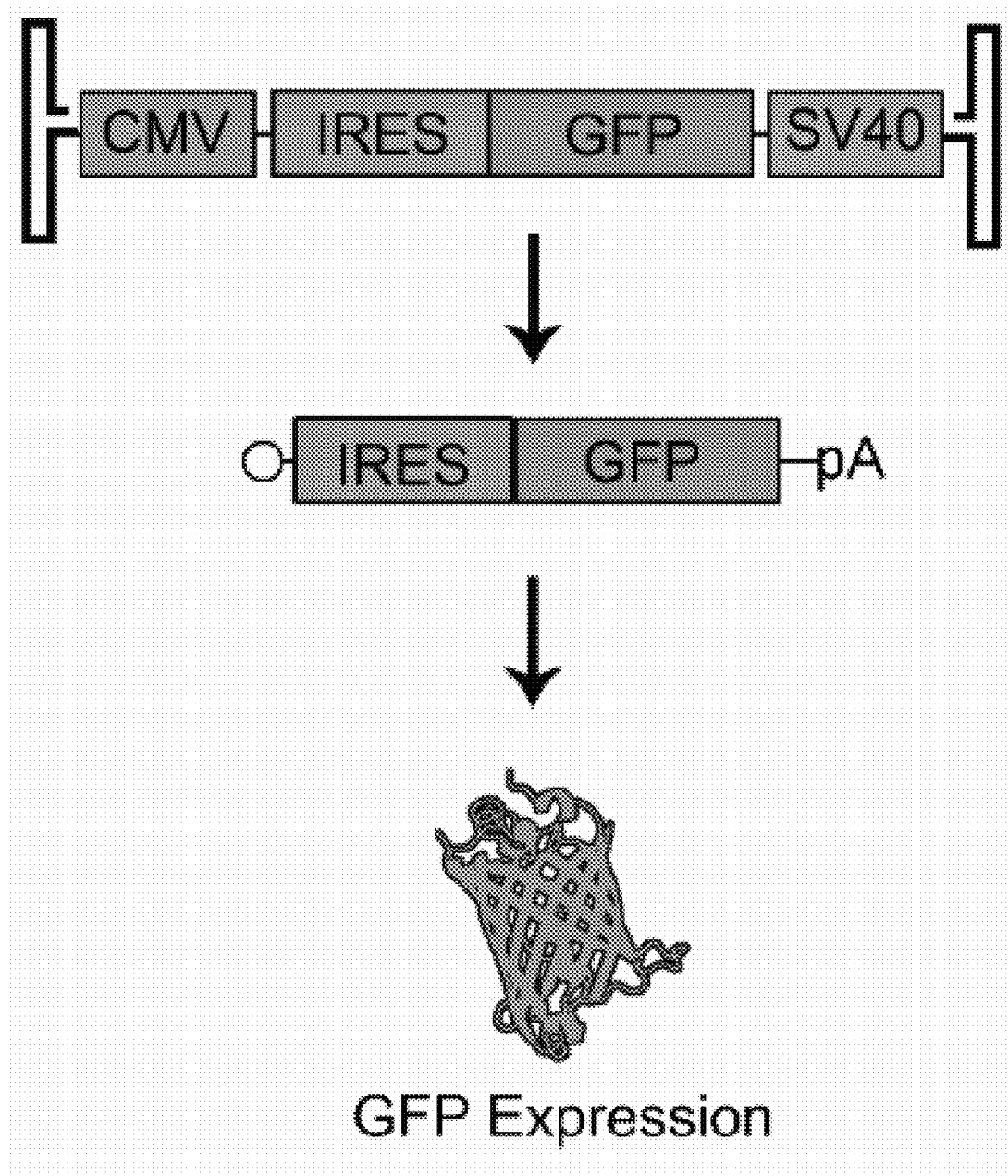
FIGS. 1A-1B: Schematic of splicing patterns and reporter outputs. The RNAs derived from the IRES-GFP (1A) and ZKSCAN1 split GFP or HIPK3 split GFP (1B) constructs are expressed from the CMV promoter and are capped and poly-adenylated in their linear isoforms. (1A) The control IRES-GFP transcript contains an EMCV IRES followed by GFP. (1B) The precursor split GFP transcript contains a split GFP cassette flanked by intron sequences derived from the human ZKSCAN1 or HIPK3 genes. Donor and acceptor splice sites are represented by grey triangles and the dotted lines indicate the backsplice pattern. The GFP fragments are separated by an EMCV IRES such that upon RNA circularization, full length GFP is expressed.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference herein in their entirety.

Definitions

The following terms can be used in the description herein and the appended claims: The singular forms "a," "an" and "the" can be intended to include the plural forms as well, unless the context clearly indicates otherwise. Furthermore, the term "about," as used herein when referring to a measurable value such as an amount of the length of a polynucleotide or polypeptide sequence, dose, time, temperature, and the like, can be meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms can mean a decrease of at least about 25%, 35%, 50%, 75%, 80%, 85%, 90%, 95%, 97% or more.

As used herein, the terms "enhance," "enhances," "enhancement" and similar terms can indicate an increase of at least about 5%, 10%, 20%, 25%, 50%, 75%, 100%, 150%, 200%, 300%, 400%, 500% or more.

The term "parvovirus" as used herein can encompass the family Parvoviridae, including autonomously replicating parvoviruses and dependoviruses. The autonomous parvoviruses can include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al, VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, avian AAV, bovine AAV, canine AAV, equine AAV, ovine AAV, and any other AAV now known or later discovered. See, e.g., BERNARD N. FIELDS et al, VIROLOGY, volume 2, chapter 69 (4th ed., Lippincott-Raven Publishers). A number of relatively new AAV serotypes and clades have been identified (see, e.g., Gao et al. (2004) *J Virology* 78:6381-6388; Moris et al. (2004) *Virology* 33-:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as the GenBank® Database. See, e.g., GenBank Accession Numbers NC_044927, NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al. (1983) *J Virology* 45:555; Chiorini et al. (1998) *J. Virology* 71:6823; Chiorini et al (1999) *J Virology* 73:1309; Bantel-Schaal et al. (1999) *J. Virology* 73:939; Xiao et al. (1999) *J. Virology* 73:3994; Muramatsu et al. (1996) *Virology* 221:208; Shade et al. (1986) *J Virol.* 58:921; Gao et al. (2002) *Proc. Nat. Acad. Sci. USA* 99: 1 1854; Moris et al. (2004) *Virology* 33:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al. (2002) Proc. Nat. Acad. Sci. 99: 10405-10), AAV4 (Padron et al. (2005) J Virol. 79: 5047-58), AAV5 (Walters et al. (2004) J Virol. 78: 3361-71) and CPV (Xie et al. (1996) J Mol. Biol. 6:497-520 and Tsao et al. (1991) Science 251: 1456-64).

The term "tropism" as used herein can refer to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest. Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form the virus may take within the cell.

As used herein, "systemic tropism" and "systemic transduction" (and equivalent terms) can indicate that the virus capsid or virus vector of the invention exhibits tropism for or transduces, respectively, tissues throughout the body (e.g., brain, eye, lung, skeletal muscle, heart, liver, kidney and/or pancreas). In embodiments of the invention, systemic transduction of muscle tissues (e.g., skeletal muscle, diaphragm and cardiac muscle) is observed. In other embodiments, systemic transduction of skeletal muscle tissues is achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector can be administered via a systemic route (e.g., systemic route such as intravenously, intra-articularly or intra-lymphatically).

Alternatively, in other embodiments, the capsid or virus vector is delivered locally (e.g., to the footpad, intramuscularly, intradermally, subcutaneously, topically). In further embodiments, the capsid or virus vector is delivered to the eye. In embodiments, the capsid or virus vector is administered via an intravitreal, subretinal, subconjunctival, retrobulbar, intracameral and/or suprachoroidal route.

Unless indicated otherwise, "efficient transduction" or "efficient tropism," or similar terms, can be determined by reference to a suitable control (e.g., at least about 50%, 60%, 70%, 80%, 85%, 90%, 95% or more of the transduction or tropism, respectively, of the control). In particular embodiments, the virus vector efficiently transduces or has efficient tropism for skeletal muscle, cardiac muscle, diaphragm muscle, pancreas (including (3-islet cells), spleen, the gastrointestinal tract (e.g., epithelium and/or smooth muscle), cells of the central nervous system, lung, joint cells, kidney and/or cell or cell layers of the eye. Suitable controls will depend on a variety of factors including the desired tropism profile.

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism) for liver, kidney, gonads and/or germ cells. In particular embodiments, undesirable transduction of tissue(s) (e.g., liver) is 20% or less, 10% or less, 5% or less, 1% or less, 0.1% or less as compared with the level of transduction of the desired target tissue(s) (e.g., skeletal muscle, diaphragm muscle, cardiac muscle and/or cells of the central nervous system).

As used herein, the term "polypeptide" can encompass both peptides and proteins, unless indicated otherwise.

A "polynucleotide" can be a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") can mean a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide can mean a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate" or "purify" (or grammatical equivalents) a virus vector, it can be meant that the virus vector is at least partially separated from at least some of the other components in the starting material. In representative embodiments an "isolated" or "purified" virus vector is enriched by at least about 10-fold, 100-fold, 1000-fold, 10,000-fold or more as compared with the starting material.

A "therapeutic protein" can be a protein that can alleviate, reduce, prevent, delay and/or stabilize symptoms that result from an absence or defect in a protein in a cell or subject and/or is a protein that otherwise confers a benefit to a subject.

A "therapeutic RNA molecule" or "functional RNA molecule" as used herein can be an antisense nucleic acid, a ribozyme (e.g., as described in U.S. Pat. No. 5,877,022), an RNA that effects spliceosome-mediated trans-splicing (see, Puttaraju et al. (1999) *Nature Biotech.* 17:246; U.S. Pat. Nos. 6,013,487; 6,083,702), an interfering RNA (RNAi) including siRNA, shRNA or miRNA, which mediate gene silencing (see, Sharp et al. (2000) *Science* 287:2431), and any other non-translated RNA, such as a "guide" RNA (Gorman et al. (1998) *Proc. Nat. Acad. Sci USA* 95:4929; U.S. Pat. No. 5,869,248 to Yuan et al.) and the like as are known in the art.

By the terms "treat," "treating" or "treatment of" (and grammatical variations thereof) it can be meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) can refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein can be an amount that is sufficient to provide some improvement or benefit to the subject. Alternatively stated, a "treatment effective" amount can be an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein can be an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid molecule" are used interchangeably herein and can refer to a nucleic acid sequence that is not naturally occurring in the virus. Generally, the heterologous nucleic acid comprises an open reading frame that encodes a protein or nontranslated RNA of interest (e.g., for delivery to a cell or subject).

As used herein, the terms "viral vector," "virus vector," "vector," "virus particle," "particle," "recombinant viral vector" or "gene delivery vector" refer to a virus (e.g., AAV) particle that can function as a nucleic acid delivery vehicle, and which comprises the vector genome (e.g., viral DNA [vDNA]) packaged within a virion.

Alternatively, in some contexts, the term "vector" may be used to refer to the vector genome/vDNA alone.

As used herein, the term "capsid" or "viral capsid" refers to a capsid structure made up of capsid proteins, wherein the capsid comprises a nucleic acid molecule, which can be a genome, such as a viral genome (e.g., AAV genome in an AAV capsid).

A "rAAV vector genome" or "rAAV genome" can be an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka (1992) *Curr. Topics Microbiol. Immunol.* 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention, the rAAV vector genome comprises at least one terminal repeat (TR) sequence (e.g., AAV TR sequence), optionally two TRs (e.g., two AAV TRs), which typically will be at the 5' and 3' ends of the vector genome and flank the heterologous nucleic acid sequence, but need not be contiguous thereto. The TRs can be the same or different from each other.

The term "terminal repeat" or "TR" can include any viral terminal repeat or synthetic sequence that forms a hairpin structure and functions as an inverted terminal repeat (i.e., mediates the desired functions such as replication, virus packaging, integration and/or pro virus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or pro virus rescue, and the like.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al. (2000) *Molecular Therapy* 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention. Further, the viral capsid or genomic elements can contain other modifications, including insertions, deletions and/or substitutions.

As used herein, the term "amino acid" can encompass any naturally occurring amino acid, modified forms thereof, and synthetic amino acids. Naturally occurring, levorotatory (L-) amino acids are shown in Table 2.

Alternatively, the amino acid can be a modified amino acid residue (nonlimiting examples are shown in Table 3) and/or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described by Wang et al. (2006) *Annu Rev Biophys Biomol Struct.* 35:225-49. These unnatural amino acids can advantageously be used to chemically link molecules of interest to the AAV capsid protein.

Nucleic Acid Molecules and Virus Capsids and Virus Vectors Comprising the Same

In one embodiment, the present invention provides a nucleic acid molecule encoding a circular RNA (circRNA) that is covalently closed, wherein the nucleic acid molecule comprises: a) a gene of interest which can be transcribed into noncoding RNA or a translatable mRNA; b) intronic elements that flank the gene of interest, wherein the intronic elements are backspliced by the cellular splicing machinery to yield a circular RNA that is covalently closed; c) an internal ribosome entry site (IRES) driving translation of the translatable mRNA transcribed from the gene of interest; d) a promoter region in the 5'untranslated region (UTR) and outside of the intronic elements that flank the gene of interest; and e) a translation regulating region in the 3' UTR and outside of the intronic elements that flank the gene of interest.

In some embodiments, the intronic elements of (b) are selected from the group consisting of any known intronic element(s), in any combination and in any multiples and/or ratios. Examples of intronic elements include those described in Rybak-Wolf et al. (2005) *Mol. Cell* 58(5):870-885 and those described in the circBase circular RNA database (Glazar et al. (2014) *RNA* 20:1666-1670; and www.circbase.org), all incorporated by reference herein in their entirety.

In some embodiments, the intronic elements of (b) can comprise consist essentially of or consist of the nucleotide sequence of any of SEQ ID NOs:13-24 or 29-32, in any combination thereof, and in any multiples and/or ratios.

In some embodiments, the IRES of (c) can be a viral IRES listed in Table 5, a cellular IRES listed in Table 6, singly or any combination thereof, and/or in any multiples and/or ratios.

In some embodiments, the translation regulating region of (e) can comprise, consist essentially of and/or consist of a polyadenylation (polyA) sequence and/or a structural element that stabilizes the circRNA, as would be well known in the art.

In one embodiment, the present invention provides an adeno-associated virus (AAV) genome comprising the nucleic acid molecule of the invention, flanked on either side or on both sides by AAV inverted terminal repeats (ITRs).

In one embodiment, the present invention provides an AAV capsid or particle comprising the AAV genome and/or the nucleic acid molecule of the invention. The AAV capsid or particle can be an AAV vector.

The present invention further provides a composition comprising the nucleic acid molecule of this invention, the AAV genome of this invention, and/or the AAV capsid or particle or vector of this invention, in a pharmaceutically acceptable carrier. As used herein, the term "pharmaceutically acceptable" means a carrier material that is not toxic or otherwise undesirable, i.e., the material may be administered to a subject without causing any undesirable biological effects.

The present invention further provides a method of expressing a covalently closed circular RNA molecule in a cell, comprising introducing into the cell the nucleic acid molecule of this invention, the AAV genome of this invention, the AAV capsid or particle of this invention, and/or the composition of this invention, under conditions wherein the covalently closed circular RNA molecule is transcribed.

In another embodiment, the present invention provides a method of expressing a covalently closed circular RNA molecule in a tissue specific and/or cell specific manner, comprising contacting the tissue and/or the cell with the nucleic acid molecule of this invention, the AAV genome of this invention, the AAV capsid or particle of this invention, and/or the composition of this invention, under conditions wherein the covalently closed, circular RNA molecule is expressed.

In some embodiments, the RNA molecule is a therapeutic mRNA molecule (e.g., a therapeutic RNA molecule encoding a protein), an RNA silencing molecule, a guide RNA molecule that can target a genomic element, a guide RNA molecule that can target an RNA transcript, a tRNA molecule, a long noncoding RNA molecule, an antisense RNA molecule, or any combination thereof.

In some embodiments, the cell and/or tissue is from a subject of this invention, which can be a mammal and in some embodiments, is a human.

In some embodiments of this invention, the nucleic acid molecule of this invention can be a linear nucleic acid molecule or a circular nucleic acid molecule. The nucleic acid molecule can be an RNA molecule or a DNA molecule, which can be single stranded or double stranded. The nucleic acid molecule can be introduced into a cell or tissue of a subject and/or into a subject as a naked nucleic acid molecule or the nucleic acid molecule can be part of a nucleic acid construct, plasmid, vector, viral vector, capsid or particle.

In some embodiments, the circRNA molecule of this invention can encode a therapeutic RNA and no IRES element is needed to drive translation of a nucleic acid sequence into an amino acid sequence.

In some embodiments, the circRNA molecule of this invention can encode a protein and an IRES element can be present in the circRNA molecule to drive translation of a nucleic acid sequence into an amino acid sequence.

One aspect of the present invention includes the administration of an AAV vector encoding a circRNA molecule of this invention into mammalian cells or animals, e.g., for therapy or bioproduction of useful proteins. The method is advantageous in providing the production of a desired circRNA coding a polypeptide inside eukaryotic cells with a longer half-life than linear RNA, due to resistance from ribonucleases and bases.

Another aspect of the present invention includes the administration of a circRNA molecule of this invention into mammalian cells or animals, e.g., for therapy or production of proteins or noncoding RNA. The circular RNA can be transfected as is, or can be transfected in DNA vector form and transcribed in the cell, as desired. Cellular transcription can use added polymerases or nucleic acids encoding same, or preferably can use endogenous polymerases. The preferred half-life of a circular RNA in a eukaryotic cell is at least 20 hrs, 30 hrs or even at least 40 hrs, as measured by either a hybridization or quantitative RT-PCR experiments. In some embodiments, the present invention provides a circular RNA with a half-life of at least 20 hrs in a eukaryotic cell or with a half-life of at least twice that of the same mRNA that is linear inside a eukaryotic cell.

In one embodiment, the present invention provides a covalently closed circular RNA molecule with an IRES, 5' UTR, coding sequence of interest, 3' UTR and polyadenylation sequence, in that order. Many different combinations of these RNA elements with translation enhancing properties and synergy can be created. Such combinations include but are not limited to IRES-ORF-3' UTR-polyA, IRES-ORF-3' UTR, IRES-5' UTR-ORF-3' UTR, and the like.

In some embodiments, a circular RNA molecule of this invention can comprise modified RNA nucleotides. Nonlimiting examples of modified ribonucleotide bases include 5-methylcytidine and pseudouridine. These nucleotides provide additional stability and resistance to immune activation.

Another embodiment of the invention includes in vitro transcription of a DNA template encoding the circular RNA molecule of this invention. Inverted intron self-splicing sequences at both ends of the RNA molecule facilitate the formation of circular RNA without any additional enzymes being needed.

An additional embodiment of the invention includes the production of circular RNA inside the cell, which can be transcribed off a DNA template in the cytoplasm by a bacteriophage RNA polymerase, or in the nucleus by host RNA polymerase II.

One embodiment of the invention consists of the administration of a circular RNA of this invention into an organism, such as a human or animal, such that a polypeptide encoded by the circular RNA molecule is expressed inside the organism. The polypeptide can either be present intracellularly or secreted.

In another embodiment of the invention, circular RNA can be transfected inside cells in tissue culture to express desired polypeptides of interest. In particular, circular RNA can express intracellular proteins and membrane proteins in the cells of interest.

In some embodiments of this invention, an RNA polymerase promoter and terminator can be from the T7 virus, T6 virus, SP6 virus, T3 virus, or T4 virus.

In some embodiments, a 3' UTR of this invention can be from human beta globin, human alpha globin *Xenopus* beta globin, *Xenopus* alpha globin, human prolactin, human GAP-43, human eEF1a1, human Tau, human TNF alpha, dengue virus, hantavirus small mRNA, bunyavirus small mRNA, turnip yellow mosaic virus, hepatitis C virus, rubella virus, tobacco mosaic virus, human IL-8, human actin, human GAPDH, human tubulin, hibiscus chlorotic rinsgpot virus, woodchuck hepatitis virus post translationally regulated element, sindbis virus, turnip crinkle virus, tobacco etch virus, or Venezuelan equine encephalitis virus.

In some embodiments, a 5' UTR of this invention can be from human beta globin, *Xenopus laevis* beta globin, human alpha globin, *Xenopus laevis* alpha globin, rubella virus, tobacco mosaic virus, mouse Gtx, dengue virus, heat shock protein 70 kDa protein 1A, tobacco alcohol dehydrogenase, tobacco etch virus, turnip crinkle virus, or the adenovirus tripartite leader.

In some embodiments, a polyA sequence of this invention is at least 30 nucleotides long or at least 60 nucleotides long.

Nonlimiting examples of an IRES of this invention include those listed in Table 5-6 here, as well as an IRES from Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, *Homalodisca coagulata* virus-1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n.myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, WO0155369, tobacco etch virus, turnip crinkle virus, or an aptamer to eIF4G.

In some embodiments an IRES of this invention can be combined with a second IRES or third IRES, facilitating additional initiation factor recruitment, ribosome subunit binding, ribosome shunting, ribosome basepairing, or ribosome translocation.

In some embodiments, the present invention provides a method of making circular RNA, said method comprising adding ribonucleotide triphosphates, inorganic pyrophosphatase, RNase inhibitor, and an RNA polymerase to a vector of this invention in an appropriate reaction buffer, transcribing RNA from said vector, and allowing self-circularization of said transcribed RNA to produce circular mRNA.

In some embodiments, ribonucleotides of this invention can include modified ribonucleotides m5C, m5U, m6A, s2U, .PSI., or 2'-O-methyl-U.

In some embodiments, the present invention provides a method of gene therapy, comprising introducing a circular RNA and/or vector of this invention into a subject in need thereof.

In some embodiments, the present invention provides a method of bioproducing a protein, comprising introducing a circular RNA and/or vector of this invention into a eukaryotic cell or a mammal for production of a protein encoded by an open reading frame (ORF).

In particular embodiments, the AAV capsid protein has the native AAV capsid protein sequence or has an amino acid sequence that is at least about 90%, 95%, 97%, 98% or 99% similar or identical to a native AAV capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, (1981) *Adv. Appl. Math.* 2, 482, by the sequence identity alignment algorithm of Needleman & Wunsch (1970) *J Mol. Biol.* 48, 443, by the search for similarity method of Pearson & Lipman, (1988) *Proc. Natl. Acad. Sci. USA* 85, 2444, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984) *Nucl. Acid Res.* 12, 387-395, or by inspection.

Another suitable algorithm is the BLAST algorithm, described in Altschul et al. (1990) *J Mol. Biol.* 215, 403-410, and Karlin et al. (1993) *Proc. Natl. Acad. Sci. USA* 90, 5873-5787. A particularly useful BLAST program is the WU-BLAST-2 program which was obtained from Altschul et al. (1996) *Methods in Enzymology,* 266, 460-480; blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity. Further, an additional useful algorithm is gapped BLAST as reported by Altschul et al. (1997) *Nucleic Acids Res.* 25, 3389-3402.

The invention also provides a virus capsid comprising, consisting essentially of, or consisting of the AAV genome of the invention. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11 or any other AAV shown in Table 1 or is derived from any of the foregoing by one or more insertions, substitutions and/or deletions.

The virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules can be defined as those that are not naturally found in an AAV infection, e.g., those not encoded by a wild-type AAV genome. Further, therapeutically useful molecules can be associated with the outside of the chimeric virus capsid for transfer of the molecules into host target cells. Such associated molecules can include DNA, RNA, small organic molecules, metals, carbohydrates, lipids and/or polypeptides. In one embodiment of the invention the therapeutically useful molecule is covalently linked (i.e., conjugated or chemically coupled) to the capsid proteins. Methods of covalently linking molecules are known by those skilled in the art.

The virus capsids of the invention can also find use in raising antibodies against the novel capsid structures. As a further alternative, an exogenous amino acid sequence may be inserted into the virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on particular cells and a delivery vector can be administered subsequently or concurrently, which may reduce transduction of the blocked cells, and enhance transduction of other targets (e.g., CNS progenitor cells and/or neuroblasts).

According to representative embodiments, virus capsids can be administered to a subject prior to and/or concurrently with a virus vector according to the present invention. Further, the invention provides compositions and pharmaceutical formulations comprising the inventive virus capsids; optionally, the composition also comprises a virus vector of the invention.

The invention also provides nucleic acid molecules (optionally, isolated nucleic acid molecules) encoding the virus capsids and capsid proteins of the invention. Further provided are vectors comprising the nucleic acid molecules and cells (in vivo or in culture) comprising the nucleic acid molecules and/or vectors of the invention. Suitable vectors include without limitation viral vectors (e.g., adenovirus, AAV, herpesvirus, vaccinia, poxviruses, baculoviruses, and the like), plasmids, phage, YACs, BACs, and the like. Such nucleic acid molecules, vectors and cells can be used, for example, as reagents (e.g., helper packaging constructs or packaging cells) for the production of virus capsids or virus vectors as described herein.

Virus capsids according to the invention can be produced using any method known in the art, e.g., by expression from a baculovirus (Brown et al. (1994) *Virology* 198:477-488).

The capsid proteins and capsids of the invention can comprise any modification, now known or later identified.

For example, the AAV capsid proteins and virus capsids of the invention can be chimeric in that they can comprise all or a portion of a capsid subunit from another virus, optionally another parvovirus or AAV, e.g., as described in international patent publication WO 00/28004.

The virus capsid can be a targeted virus capsid comprising a targeting sequence (e.g., substituted or inserted in the viral capsid) that directs the virus capsid to interact with cell-surface molecules present on a desired target tissue(s) (see, e.g., international patent publication WO 00/28004 and Hauck et al. (2003) *J Virology* 77:2768-2774); Shi et al. *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the PI peptide containing an RGD motif following amino acid positions 447, 534, 573 and 587 of the AAV2 capsid subunit]). Other positions within the AAV capsid subunit that tolerate insertions are known in the art (e.g., positions 449 and 588 described in Grifman et al. (2001) *Molecular Therapy* 3:964-975).

For example, some of the virus capsids of the invention have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another possibility one or more non-naturally occurring amino acids as described in Wang et al. ((2006) *Annu Rev Biophys Biomol Struct.* 35:225-49) can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques*, 1$^{st}$ edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV4, AAV5) to confer heparin binding to the resulting mutant.

B19 infects primary erythroid progenitor cells using globoside as its receptor (Brown et al. (1993) *Science* 262: 114). The structure of B19 has been determined to 8 Angstrom resolution (Agbandje-McKenna et al. (1994) *Virology* 203: 106). The region of the B19 capsid that binds to globoside has been mapped between amino acids 399-406 (Chapman et al. (1993) *Virology* 194:419), a looped out region between β-barrel structures E and F (Chipman et al. (1996) *Proc. Nat. Acad. Sci. USA* 93:7502). Accordingly, the globoside receptor binding domain of the B19 capsid may be substituted into the AAV capsid protein to target a virus capsid or virus vector comprising the same to erythroid cells.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, a-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as a-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves ((1997) *Current Biology* 7:R318) into the AAV capsid protein. Also encompassed are peptide motifs that direct uptake by specific cells, e.g., a FVFLP peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties, polysialic acid moieties, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

As yet a further alternative, the targeting sequence may be a peptide that can be used for chemical coupling (e.g., can comprise arginine and/or lysine residues that can be chemically coupled through their R groups) to another molecule that targets entry into a cell.

The foregoing embodiments of the invention can be used to deliver a heterologous nucleic acid to a cell or subject as described herein. Thus, in one embodiment, the present invention provides a method of introducing a nucleic acid molecule into a cell, comprising contacting the cell with a virus vector and/or composition of this invention.

Further provided herein is a method of delivering a nucleic acid molecule to a subject, comprising administering to the subject a virus vector of this invention and/or a composition of this invention. In some embodiments, the virus vector or composition is administered to the eye of the subject. In some embodiments, the administration is via an intravitreal, subretinal, subconjuctival, retrobulbar, intracameral and/or suprachoroidal route.

Additionally provided herein is a method of selectively transducing a cell having polysialic acid on the surface, comprising contacting the cell with a virus vector of this invention and/or a composition of this invention.

The present invention further provides a method of delivering a nucleic acid molecule of interest to an eye cell, comprising contacting the eye cell or layer with the viral vector of this invention, wherein the viral vector comprises the nucleic acid molecule of interest. In some embodiments of this method, the nucleic acid molecule of interest encodes a therapeutic protein or therapeutic RNA. In some embodiments, the therapeutic protein is a monoclonal antibody or a fusion protein.

In some embodiments of the methods described above, the eye cell or layer can be in a subject and in some embodiments, the subject can be a human subject.

The present invention further provides a method of treating an ophthalmic disorder or defect in a subject, comprising administering to the subject a viral vector of this invention, wherein the viral vector comprises a nucleic acid molecule that encodes a therapeutic protein or therapeutic RNA effective in treating the ophthalmic disorder or defect. In some embodiments of this method, the viral vector is administered via an intravitreal, subretinal, subconjuctival, retrobulbar, intracameral, and/or suprachoroidal route. In some embodiments the ophthalmic disorder or defect is retinitis pigmentosa, macular degeneration, or Leber's congenital amaurosis, achromatopsia, X-linked retinoschisis, optic neuritis, choroideremia, optic atrophy, retinal cone dystrophy, retinopathy, retinoblastoma, glaucoma, Bardet-Biedl syndrome, or color blindness.

Also provided herein is a method of delivering a nucleic acid molecule of interest (NOI) to a central nervous system progenitor cell and/or neuroblast, comprising contacting the progenitor cell and/or neuroblast with a virus vector comprising an adeno-associated virus (AAV) serotype 4 (AAV4) capsid protein, wherein the capsid protein comprises a mutation at K492, K503 and N585, and wherein the virus vector comprises the nucleic acid molecule of interest. In some embodiments of this method, the nucleic acid molecule of interest can encode a therapeutic protein or therapeutic RNA and in some embodiments, the central nervous system progenitor cell and/or neuroblast can be in a subject.

In additional embodiments of this invention, a method is provided of treating a neurological disorder or defect in a subject, comprising administering to the subject a virus vector of this invention and/or a composition of this invention, and wherein the virus vector comprises a nucleic acid molecule that encodes a therapeutic protein or therapeutic RNA effective in treating the neurological disorder or defect. In some embodiments of this method, the virus vector is administered via an intracerebroventrical, intracisternal, intraparenchymal, intracranial and/or intrathecal route. In some embodiments of this method, the subject is a human subject.

The invention also encompasses virus vectors comprising the nucleic acid molecule of the invention. In particular embodiments, the virus vector is a parvovirus vector (e.g., comprising a parvovirus capsid and/or vector genome), for example, an AAV vector (e.g., comprising an AAV capsid and/or vector genome).

For example, in representative embodiments, the virus vector comprises: (a) a virus capsid (e.g., a AAV capsid); and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid molecule encoding a protein or functional RNA of interest. Recombinant virus vectors are described in more detail below.

Methods of Producing Virus Vectors

The present invention further provides methods of producing the inventive virus vectors. In one representative embodiment, the present invention provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other Ela trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the Ela or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski (1992) *Curr. Top. Microbiol. Immun.* 158:67).

As a further alternative, the rep/cap sequences may be stably incorporated into a cell. Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the Ela or E3 regions of a deleted adenovirus). As another illustration, Palombo et al. (1998) *J Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a noninfectious adenovirus miniplasmid that carries all of the helper genes that promote efficient AAV production as described by Ferrari et al. (1997) *Nature Med.* 3: 1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the Ela or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids.

As described above, the adenovirus helper sequences and the AAV rep/cap sequences are generally not flanked by TRs so that these sequences are not packaged into the AAV virions.

Zhang et al. ((2001) *Gene Ther.* 18:704-12) describes a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al. (1999) *Gene Therapy* 6:986 and WO 00/17377.

As a further alternative, the virus vectors of the invention can be produced in insect cells using baculovirus vectors to deliver the rep/cap genes and rAAV template as described, for example, by Urabe et al. (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors

The virus vectors, capsids and particles of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors, capsids and/or particles of the present invention. Nucleic acids of interest include nucleic acids encoding polypeptides, including therapeutic (e.g., for medical or veterinary uses) or immunogenic (e.g., for vaccines) proteins and/or functional or therapeutic RNA molecules.

Therapeutic polypeptides include, but are not limited to, cystic fibrosis transmembrane regulator protein (CFTR), dystrophin (including mini- and micro-dystrophins, see, e.g., Vincent et al. (1993) *Nature Genetics* 5: 130; U.S. Patent Publication No. 2003/017131; International publication WO/2008/088895, Wang et al. (2000) *Proc. Natl. Acad. Sci. USA* 97:13714-13719; and Gregorevic et al. (2008) *Mol. Ther.* 16:657-64), myostatin propeptide, follistatin, activin type II soluble receptor, IGF-1, anti-inflammatory polypeptides such as the Ikappa B dominant mutant, sarcospan, utrophin (Tinsley et al. (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, a-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor-α soluble receptor), S100A1, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myo statin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al. (2005) *Nature Biotechnology* 23:584-590). AAV vectors may also be used to provide one or more components of a CRISPR/Cas complex or components for use in other gene editing systems. Additionally, AAV vectors may be used to provide secreted therapeutics such as fusion proteins (e.g., etanercept). If used to provide a secreted therapeutic, widespread expression of the virus is not required, as long as the secreted therapeutic can reach the target tissue of interest.

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al. (1999) Nature Biotech. 17:246; U.S. Pat. Nos. 6,013,487; 6,083,702), interfering RNAs (RNAi) including siRNA, shRNA or miRNA that mediate gene silencing (see, Sharp et al. (2000) Science 287:2431), and other non-translated RNAs, such as "guide" RNAs (Gorman et al. (1998) Proc. Nat. Acad. Sci. USA 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al. (2008) J Gene Med. 10: 132-142 and Li et al. (2005) Acta Pharmacol Sin. 26:51-55); phospholamban inhibitory or dominant-negative molecules such as phospholamban S16E (e.g., to treat cardiovascular disease, see, e.g., Hoshijima et al. (2002) Nat. Med. 8:864-871), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al. (1994) Proc. Nat. Acad. Sci USA 91:8507; U.S. Pat. No. 5,916,563 to Young et al.; U.S. Pat. No. 5,905,040 to Mazzara et al.; U.S. Pat. Nos. 5,882,652; 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg ((1991) Immunity 10:281). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al. (1994) Proc. Natl. Acad. Sci. USA 91:3515; Kawakami et al. (1994) J Exp. Med., 180:347; Kawakami et al. (1994) Cancer Res. 54:3124), MART-1, gp100 MAGE-1, MAGE-2, MAGE-3, CEA, TRP-1, TRP-2, P-15, tyrosinase (Brichard et al. (1993) J. Exp. Med. 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine (1993) Ann. Rev. Biochem. 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors, capsids and particles according to the present invention provide a means for delivering heterologous nucleic acids into a broad range of cells, including dividing and non-dividing cells. In some embodiments, the virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide and the polypeptide can be administered to the subject via gene therapy protocols. Further, the method can be practiced because the production of the polypeptide or functional RNA in the subject may impart some beneficial effect.

The virus vectors, capsid and particles of this invention can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors, capsids and particles of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease α-galactosidase] and Pompe disease [lysosomal acid α-glucosidase]) and other metabolic disorders, congenital emphysema (α1-antitrypsin), Lesch-Nyhan Syndrome (hypoxanthine guanine phosphoribosyl transferase), Niemann-Pick disease (sphingomyelinase), Tay Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, P2-adrenergic receptor, p2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like.

Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent epilepsy, stroke, traumatic brain injury, cognitive disorders, behavioral disorders, psychiatric disorders, Huntington's disease, Alzheimer's disease, amyotrophic lateral sclerosis (ALS), as well as any other neurodegenerative condition that might benefit from or require axonal/neuronal regeneration or repair.

In particular embodiments, the present invention can be practiced to promote axonal regeneration and neuronal repair, restore circuits and/or replenish lost neurons as a corrective therapy, e.g., by targeted regulation or overexpression of stem cell differentiation and reprogramming factors such as FoxJ1, Fox2, NeuroD2, NG2 or 0lig2 and/or microRNAs such as miR-137, MiR124, as well as any other factors or miRNAs implicated in neuronal development and differentiation.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors, capsids and particles according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors, capsids and particles according to the instant invention find use in diagnostic and screening methods, whereby a nucleic acid of interest is transiently or stably expressed in a cell culture system, or alternatively, a transgenic animal model.

The virus vectors, capsids and particles of the present invention can also be used for various non-therapeutic purposes, including but not limited to use in protocols to assess gene targeting, clearance, transcription, translation, etc., as would be apparent to one skilled in the art. The virus vectors, capsids and particles can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors, capsids and particles of the present invention may be used to produce an immune response in a subject. According to this embodiment, a virus vector, capsid or particle comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector, capsid or particle may be administered to a cell ex vivo and the altered cell is administered to the subject. The virus vector, capsid or particle comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, Immunophysiology: Cell Function and Cellular Interactions in Antibody Formation, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector, capsid, particle or cell comprising the heterologous nucleic acid can be administered in an immunogenically effective amount, as described herein.

The virus vectors, capsids and particles of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein.

Alternatively, the cancer antigen can be expressed as part of the virus capsid or be otherwise associated with the virus capsid (e.g., as described herein).

As another alternative, any other therapeutic nucleic acid (e.g., RNAi) or polypeptide (e.g., cytokine) known in the art can be administered to treat and/or prevent cancer.

As used herein, the term "cancer" can encompass tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors, capsids and particles according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the invention.

In particular embodiments, the present invention provides a pharmaceutical composition comprising a virus vector and/or capsid and/or particle of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector, capsid or particle may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about 10 infectious units, optionally at least about $10^5$ infectious units are introduced to the cell.

The cell(s) into which the virus vector, capsid or particle is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector, capsid or particle can be introduced into cells in vitro for the purpose of administering the modified cell to a subject. In particular embodiments, the cells have been removed from a subject, the virus vector, capsid or particle is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the virus vector, capsid or particle can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector and/or virus capsid to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units (i.e., vector genome copies), optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, intraventricular and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to the eye (e.g., administration via an intravitreal, subretinal, subconjunctival, retrobulbar, intracameral and/or suprachoroidal route.) Administration can also be to a tumor (e.g., in or near a tumor or a lymph node). The most suitable route in any given case will depend on the nature and severity of the condition being treated and/or prevented and on the nature of the particular vector that is being used.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present invention is administered to skeletal muscle, diaphragm muscle and/or cardiac muscle (e.g., to treat and/or prevent muscular dystrophy, heart disease [for example, PAD or congestive heart failure]).

The invention can also be practiced to produce antisense RNA, RNAi or other functional RNA (e.g., a ribozyme) for systemic delivery.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and virus capsids can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors.

Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis (ALS), progressive muscular atrophy, Pick's disease, muscular dystrophy, multiple sclerosis, myasthenia gravis, Binswanger's disease, trauma due to spinal cord and/or head injury (e.g., traumatic brain injury), Tay Sachs disease, Lesch-Nyan disease, epilepsy, stroke, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, any neurodegenerative condition that might benefit from or require axonal/neuronal regeneration and/or repair, cognitive disorders, behavioral disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., intravitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., intravitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01 166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain, (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve. The virus and/or capsid may be administered by an intravitreal, subretinal, subconjunctival, retrobulbar, intracameral or suprachoroidal route.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intracerebroventricular, intracisternal, intraparenchymal, intracranial, intrathecal, intraocular, intracerebral, intraventricular, intravenous (e.g., in the presence of a sugar such as mannitol), intranasal, intraaural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

The present subject matter will now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

EXAMPLES

The following EXAMPLES provide illustrative embodiments. Certain aspects of the following EXAMPLES are disclosed in terms of techniques and procedures found or contemplated by the present inventors to work well in the practice of the embodiments. In light of the present disclosure and the general level of skill in the art, those of skill will appreciate that the following EXAMPLES are intended to be exemplary only and that numerous changes, modifications, and alterations can be employed without departing from the scope of the presently claimed subject matter.

Example 1

Plasmids. Plasmids containing a portion of the human ZKSCAN1 and HIPK3 genes were used in the experiments described herein. Cloning vectors were constructed by amplifying the intron sequences and cloning into a plasmid backbone, separated by a multiple cloning site. A cassette containing the EMCV IRES and GFP (either linear or split) was cloned between these intron sequences. The split GFP cassette used was derived from the circGFP plasmid. In addition, an IRES-linear GFP cassette was also cloned into a plasmid backbone as a control. All plasmids were constructed in a backbone containing a CMV promoter, SV40 polyadenylation signal, and inverted terminal repeats derived from the AAV2 genome.

Recombinant AAV vector production. An updated triple plasmid transfection protocol was used to generate recombinant AAV vectors. Briefly, the transfection mixture contained (i) the pXR helper plasmid; (ii) the adenoviral helper plasmid pXX6-80; and (iii) the indicated transgene, driven by a CMV promoter, flanked by inverted terminal repeats derived from the AAV2 genome. Vector purification was carried out using iodixanol gradient ultracentrifugation protocol, desalted using Zeba Spin Esalting columns (40K MWCO, Thermo Scientific). Vg titers were obtained by quantitative PCR (Lightcycler 480, Roche Applied Sciences, Pleasanton, Calif.) using primers designed to selectively bind AAV2 inverted terminal repeats (forward, 5'-AAC ATG CTA CGC AGA GAG GGA GTG G-3', SEQ ID NO:1, reverse, 5'-CAT GAG ACA AGG AAC CCC TAG TGA TGG AG-3', SEQ ID NO:2).

Cell culture. HEK 293 cells were cultured in Dulbecco's Modified Eagle's Medium (GIBCO/Life technologies) supplemented with 10% FBS (Millipore-Sigma) and 1% gentamycin/kanamycin. Huh7 and U87 cells were cultured in Dulbecco's Modified Eagle's Medium (GIBCO/Life technologies) supplemented with 5% FBS (Millipore-Sigma) and 1% gentamycin/kanamycin. Neuro2A cells were cultured in MEM (GIbco/Life technologies) supplemented with 10% FBS (Millipore-Sigma) and 1% penicillin/streptomycin. All cells were maintained at 37° C. and 5% $CO_2$.

Fluorescence microscopy. Cells were seeded at ~70% confluency followed by transduction with the indicated rAAV vectors. Cells were imaged at 6, 4, 4, or 13 days post transduction (For HEK 293, Huh7, U87, and Neuro2A cells, respectively). Cells were imaged using an EVOS FL epifluorescence cell imaging system (AMC/Life Technologies) with the GFP light cube (excitation 470 nm, emission 510 nm).

RNA extraction. RNA was extracted from frozen tissue stored in RNALater or from adherent cells using Trizol reagent following the manufacturer's protocol. For tissue samples, the tissues were first homogenized in Trizol using a Tissue Lyser II (Qiagen).

Western blotting. Lysates were recovered using 1× Passive Lysis Buffer (Promega, Madison, Wis.) and store at −80° C. Samples were heated to 100° C. before separation on a 10% Tris-glycine gel and transfer to a nitrocellulose membrane. Membranes were blocked overnight at 4° C. in 5% non-fat milk in TBST. Membranes were blotted with primary antibody against either GFP (1:1000 Santa Cruz, SC9996) or Actin (1:10000, GeneTex GT5512). Stabilized peroxidase-conjugated sheep anti-mouse antibody was used as secondary antibody (1:3000, GE Healthcare NA931V). Blots were developed using SuperSignal West Femto substrate (Thermo Scientific/Life Technologies) and visualized by autoradiography or by the Chemiluminescence High Sensitivity protocol on a ChemiDoc XRS+(BioRad) for quantification purposes.

Northern blotting. 10 µg of RNA were resuspended in denaturing buffer (67% deionized formamide, 6.7% formaldehyde, 1×MOPS running buffer) incubated at 60° C. for 10 min and cooled on ice. Samples were separated on a 1.2% denaturing agarose gel and subsequently transferred to Hybond N+ membrane (GE Healthcare). Radiolabeled probe was generated using the Prime-It II Random Primer Labeling Kit (Agilent Technologies) according to manufacturer's instructions. DNA templates for probe labeling were generated by PCR with the following primers amplifying GFP (5'-GCATGCTCTTCTCAGGAGCGCAC-CATCTTCTTCAAGGACGACGG-3', SEQ ID NO:3, 5'-GCATGCTCTTCTTACCTGGACGTAGCCTTCGGG-CATGGC-3', SEQ ID NO:4). Radiolabeled probe was purified using illustra MicroSpin G-50 columns (GE Healthcare) following the manufacturer's protocol. Probe was then hybridized to the membrane in Rapid-Hyb buffer (GE Healthcare). Blots were visualized by exposure to film and radiolabel signal was quantified by exposure to a PhosphorImager screen.

Intravenous administration. Animal experiments reported in this study were conducted with C57/Bl6 mice bred and maintained in accordance to NIH guidelines as approved by the UNC Institutional Animal Care and Use Committee (IACUC). Animals were injected intravenously through the tail vein with $5.5 \times 10^{11}$ vg/animal. At 4 weeks post injection, mice were overdosed with tribromoethanol (avertin) (0.2 ml/10 g of 1.25% solution) via the intraperitoneal route. This was followed by transcardial perfusions of phosphate-buffered saline. Portions of the harvested organs were cut and stored in RNAlater solution (Invitrogen); the remainder was postfixed in 4% paraformaldehyde.

ICV administration. Animal experiments reported in this study were conducted with C57/Bl6 mice bred and maintained in accordance to NIH guidelines as approved by the UNC Institutional Animal Care and Use Committee (IACUC). Pups at postnatal day 1-2 were rapidly anesthetized on ice for 2 minutes followed by stereotaxic ICV injections. Specifically, vectors packaging different transgenes were injected into the left lateral ventricle (total volume <3 µl) using a Hamilton 700 series syringe with a 26s gauge needle (Sigma-Aldrich, St. Louis, Mo.), attached to a KOPF-900 small animal stereotaxic instrument (KOPF instruments, Tujunga, Calif.). All neonatal injections were performed 0.5 mm relative to the sagittal sinus, 2 mm rostral to transverse sinus and 1.5 mm deep. Following vector administration, mice were revived under a heat lamp and rubbed in the bedding before being placed back with the dam. At 6 weeks post injection, mice were overdosed with tribromoethanol (avertin) (0.2 ml/10 g of 1.25% solution) via the intraperitoneal route. This was followed by transcardial perfusions of 4% paraformaldehyde in phosphate-buffered saline. The brain was harvested and postfixed in 4% paraformaldehyde for 24 hours.

Tissue processing and immunohistochemistry. Using fixed tissues, 50 µm thick sections were obtained using a Leica VT 1,200S vibrating blade microtome (Leica Biosystems, Buffalo Grove, Ill.). The immunohistochemical analyses of GFP expression was conducted using Vectastain ABC-HRP kit (Rabbit IgG PK-4001 kit, Vector biolabs, Burlingame, Calif.) according to the manufacturer's protocol. Zeiss CLSM 700 confocal laser scanning microscope was used for imaging sections of different organs after immunostaining (Microscopy Services Laboratory, UNC). Quantification was performed in ImageJ. Sections were converted to 16-bit images and inverted, followed by background removal by the rolling ball method. The integrated density and area of each section was measured, as well as for a no staining control section. Density was normalized to area, and background values (from the no stain control) subtracted.

Vector genome quantification. Genomic DNA was extracted from sections of fixed tissue using the QiaAmp DNA FFPE Tissue Kit (Qiagen). To calculate viral genome copy numbers, quantitative PCR was performed with primers specific to the CMV promoter (5'-CAAGTACGCCCCC-TATTGAC-3', SEQ ID NO:5, and 5'-AAGTCCCGTTGAT-TTTGGTG-3', SEQ ID NO:6). The vector genome copy numbers were normalized to the mouse lamin B2 locus as the housekeeping gene (primers 5'-GGACCCAAGGAC-TACCTCAAGGG-3', SEQ ID NO:7, and 5'-AGGGCACCTCCATCTCGGAAAC-3', SEQ ID NO:8).

Intravitreal administration. Animal experiments reported in this study were conducted with C57/Bl6 mice bred and maintained in accordance to NIH guidelines as approved by the UNC Institutional Animal Care and Use Committee (IACUC). Prior to injection, eyes were dilated with 1% atropine and 2.5% phenylephrine HCl (Akorn Inc, Lake Forest, Ill.) ophthalmic solution. Mice were anesthesized using 200 mg/kg tribromoethanol (avertin). A small hole was made at the limbus of the eye with a 30G needle, and then 1 µL virus was slowly delivered with a 34G needle on a Hamilton gastight syringe. Four weeks post-injection, mice were sacrificed via $CO_2$ inhalation. Limbi were marked at the top of each eye to facilitate orientation. Following this, eyes were enucleated in 4% paraformaldehyde and incubated at 4° C. overnight. Cornea was dissected away from the eyecup, then eyecup immersed in 30% sucrose for 3 hours, cryoprotected in Optimal Cutting Temperature compound (Sakura Finetek, Torrance, Calif.), and stored at −20° C. Where noted, the eyecup was stored in RNAlater (Invitrogen) for later RNA extraction.

Tissue immunofluorescence. 12 µM retinal sections were cut on a Leica CM3050 cryostat (Leica Biosystems Inc., Buffalo Grove, Ill.). Slides were then rinsed with 1×PBS (Gibco, Gaithersburg, Md.) three times. Retinal sections on the slides were covered with 0.5% Triton X-100 and 1% BSA (Fisher Scientific, Waltham, Mass.), each for 1 hour. Rabbit anti-GFP (Invitrogen, G10362) was diluted 1:750 in 1% BSA+0.3% Triton X-100 and incubated with the sections at 4° C. overnight. Slides were rinsed with 1×PBS and incubated with Alexa Fluor goat anti-rabbit 488 (1:500, Invitrogen A-11008) at room temperature. Following rinsing, ProLong Gold DAPI containing mounting media (Life Technologies, Waltham, Mass.) was applied and slides coverslipped. Fluorescence was quantified in ImageJ by the corrected total fluorescence method.

RT-PCR. 5 ug of RNA was DNase treated using the Turbo DNA-free kit (Ambion/Life Technologies). Equal nanogram amounts of DNase treated RNA was converted to cDNA using the High Capacity RNA-to-cDNA kit (Applied Biosystems/Life Technologies). Products of this reverse transcription reaction were utilized as template for PCR (or quantitative PCR) using gene-specific primers for GFP (5'-ctgcttgtcggccatgatatagacgttgtggc-3', SEQ ID NO:9, 5'-caagctgaccctgaagttcatctgcaccacc-3', SEQ ID NO:10) and glyceraldehyde 3-phosphate dehydrogenase (GAPDH) (5'-CCACTCCTCCACCTTTGAC-3', SEQ ID NO:11, 5'-ACCCTGTTGCTGTAGCC-3', SEQ. ID NO:12). Non-quantitative PCR products were visualized on an agarose gel. For RNAse R experiments, 5 micrograms of RNA were treated with 5 units of RNaseR (Epicentre) at 37° C. for 10 minutes. Enzyme was inactivated at 95° C. for 5 minutes. The resulting RNA was used for RT-PCR as described above.

Figure 1B:
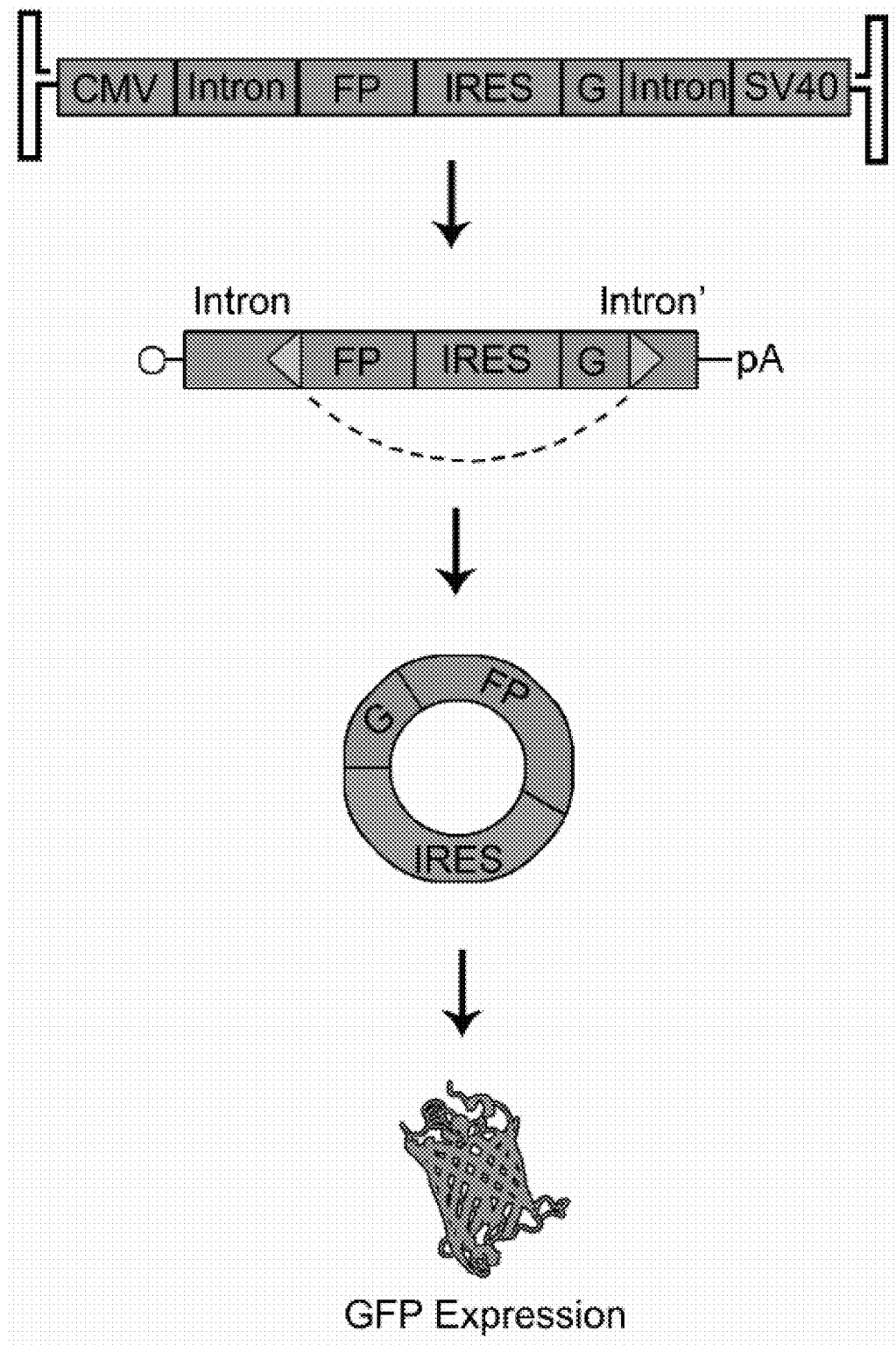

Here we show that adeno-associated virus (AAV) can be used to deliver transgene cassettes that will express circular RNAs in vivo. The reporter design was based on intron sequences from the human ZKSCAN1 and HIPK3 genes. Exons 2 and 3 of the ZKSCAN1 mRNA and exon 2 of the HIPK3 mRNA are naturally backspliced to form circRNAs. To create reporter constructs, a portion of the intron sequences that flank the endogenously circularized exon was placed into a vector. Between the intron sequences, a split GFP open reading frame was placed, such that it would be reconstituted only in the circular RNA. The EMCV IRES was also placed before GFP to drive translation in the circular context. This was done with both intron sequences, creating the ZKSCAN1 split GFP and HIPK3 split GFP constructs. As a control for IRES-dependent translation, a cassette consisting of the EMCV IRES and GFP was cloned into a vector lacking intron sequences to facilitate backsplicing (FIGS. 1A-1B).

Figure 2A:
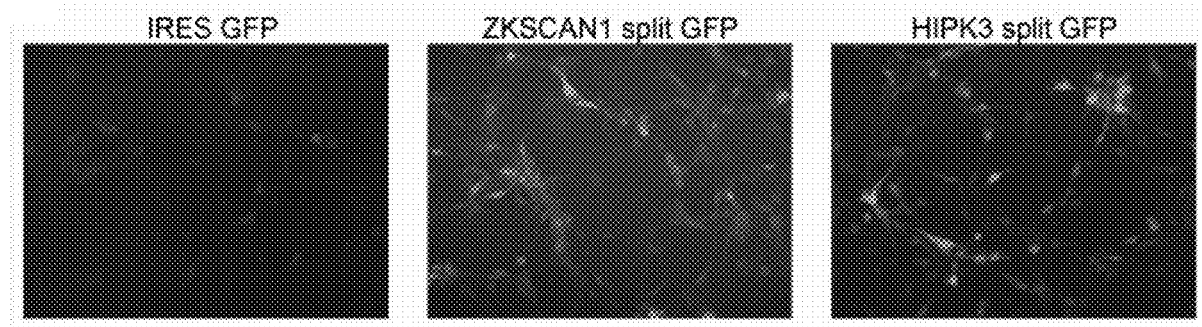
FIGS. 2A-2E: circRNAs are expressed in a tissue culture model of glioblastoma. (2A) Representative images of GFP fluorescence from U87 cells expressing IRES GFP (left), ZKSCAN1 split GFP (middle), or HIPK3 split GFP(right) 4 days post transduction with 100,000 vector genomes per cell of recombinant AAV2 vector. (2B) Western blot detecting GFP or loading control Actin for lysates of U87 cells transduced as indicated above, quantified in (2C). (2D) Northern blotting of total cellular RNA probed against GFP, to characterize various RNA species expressed from the IRES GFP, ZKSCAN1 split GFP, or HIPK3 split GFP constructs. The position of 18S rRNA is noted as a marker of size. Schematics of expected RNA species are depicted. The circRNA band is quantitated on the right, shown relative to the level of IRES GFP RNA, quantified in (2E).
Figure 2B:
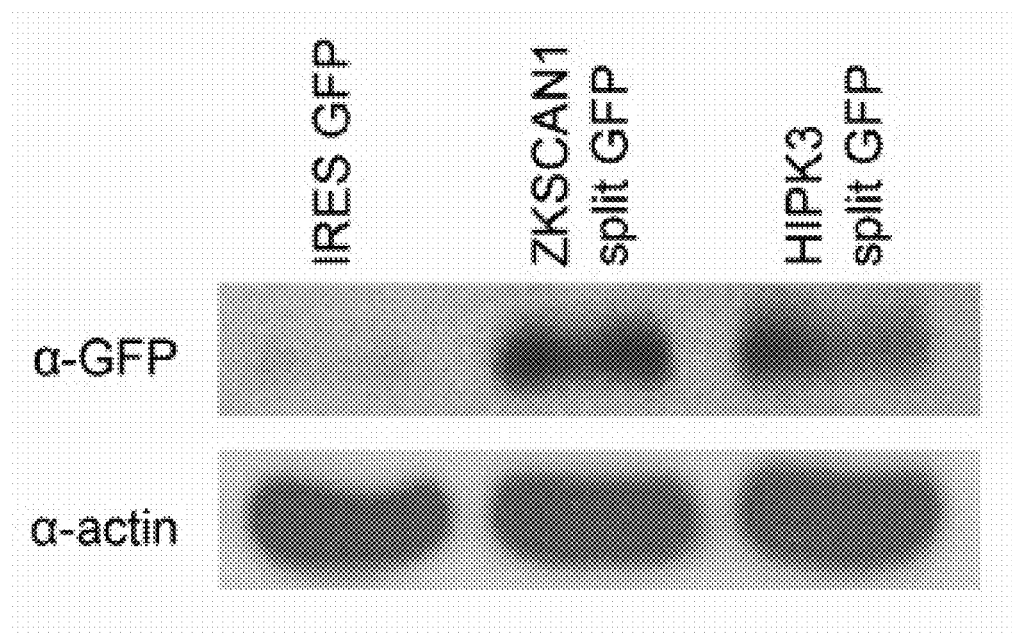
Figure 2C:
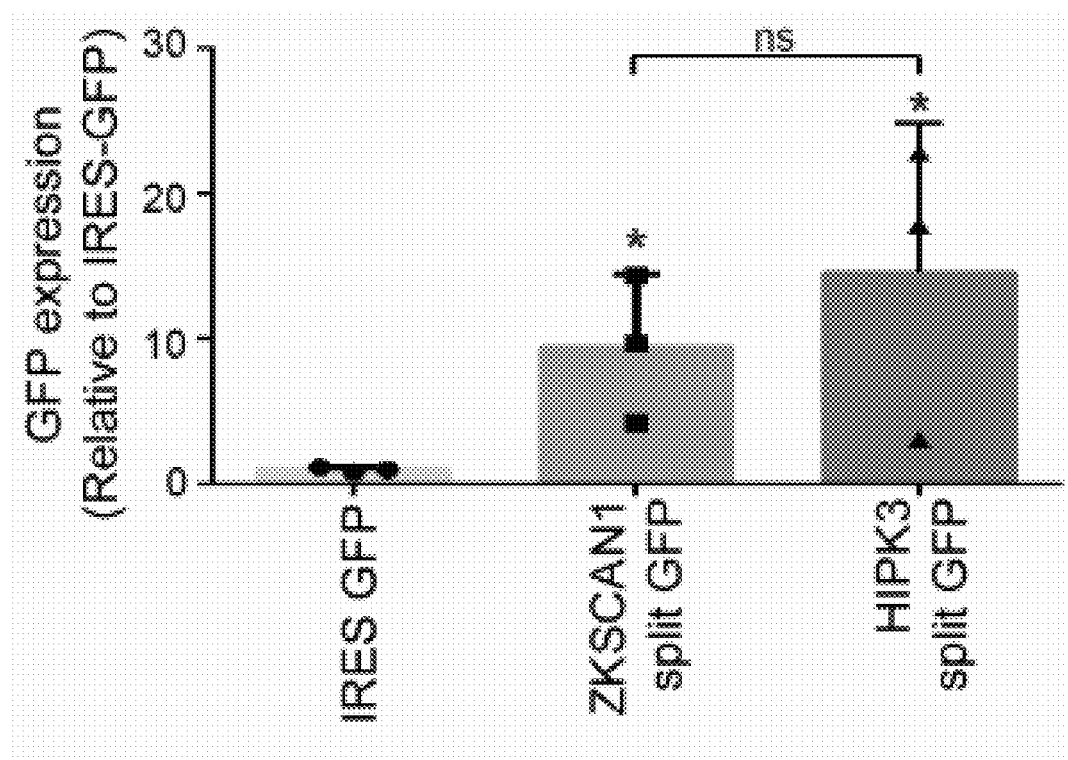
Figure 2D:
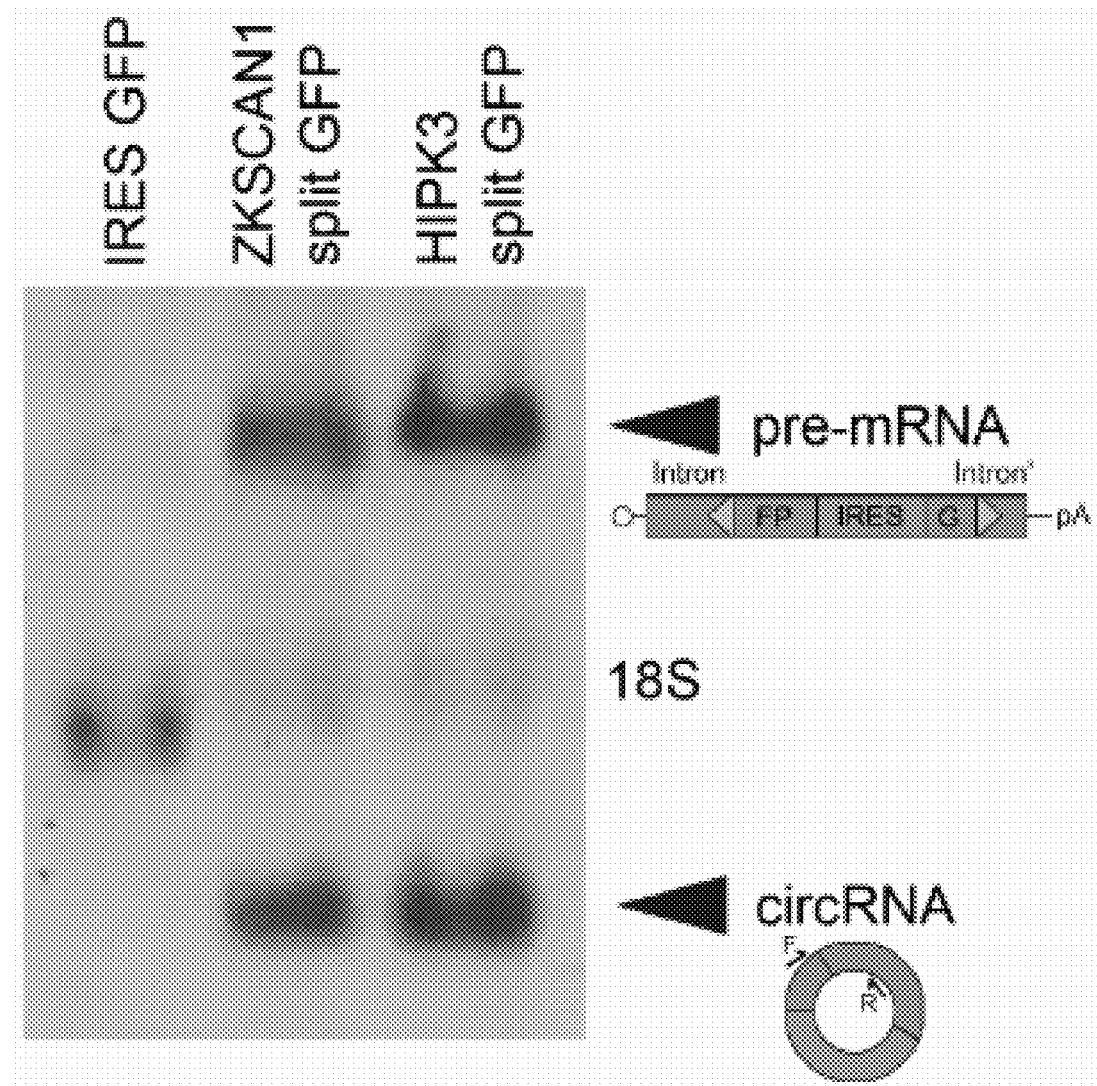
Figure 2E:
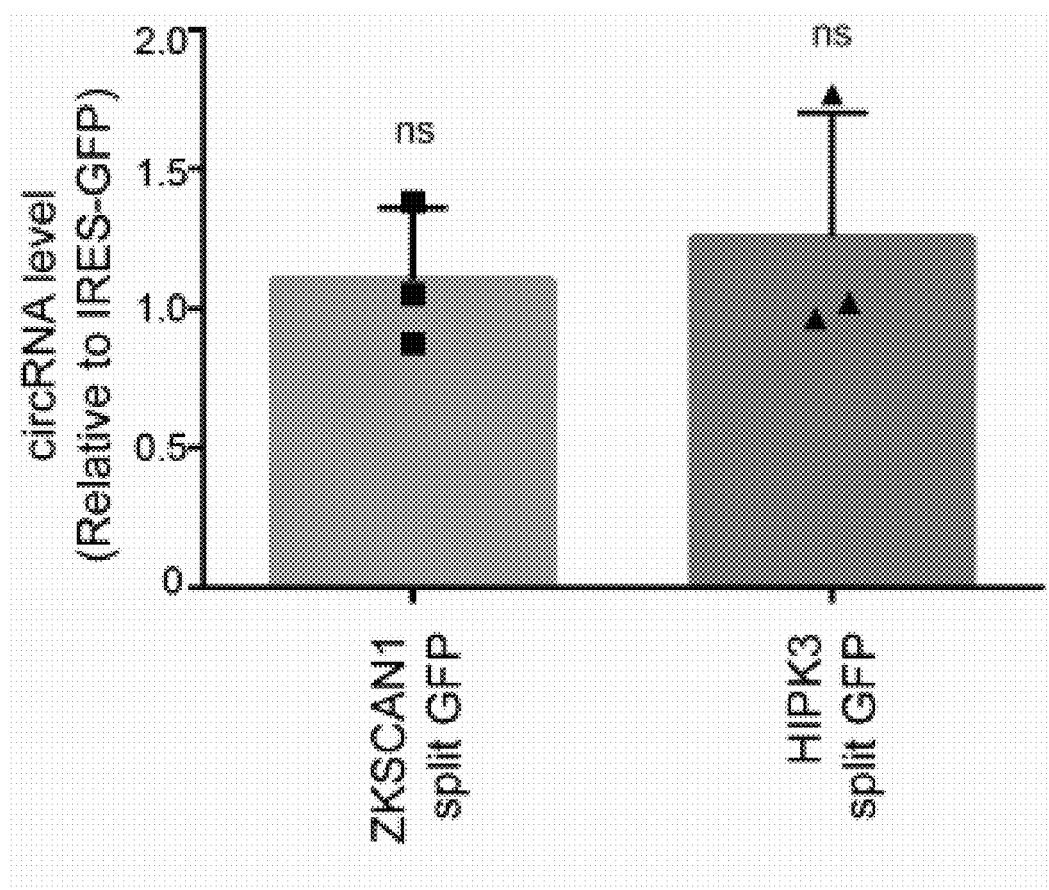
Figure 3A:
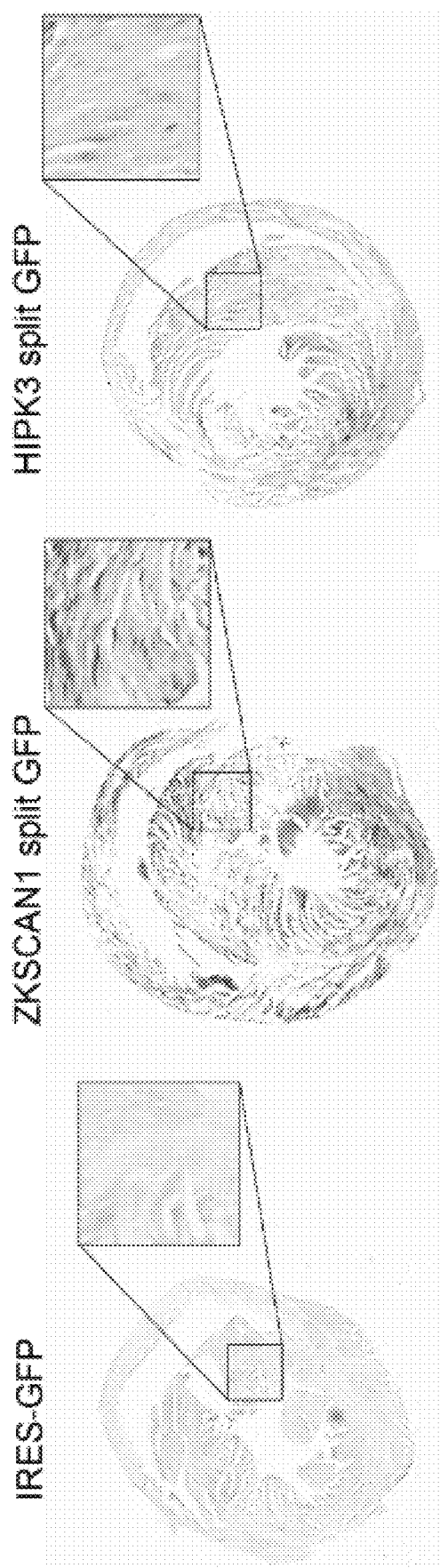
FIGS. 3A-3F: circRNAs are expressed in murine cardiac tissue. The indicated constructs were packaged in to recombinant AAV9 vectors and injected intravenously into C57/BL6 mice at a dose of 5.5e11 vector genomes per animal, and then harvested four weeks post injection. (3A) Cardiac tissue was sectioned, followed by immunohistochemical staining to visualize GFP expression. (3B) The level of GFP expression in stained cardiac sections was quantified by mean pixel intensity. (3C) Quantification of the viral genome copy number in each cohort by qPCR with primers specific to the CMV promoter, normalized to the mouse lamin B2 locus. (3D) RNA was extracted from cardiac tissue and RT-PCR performed with primers amplifying across the back-splice junction (see schematic); these primers also amplify the full-length GFP produced in IRES GFP. (3E) Quantitative RT-PCR was performed with the same samples and primer set as in (3D). (3F) RNA was treated with RNAse R and then RT-PCR was performed as in (3D).
Figure 3B:
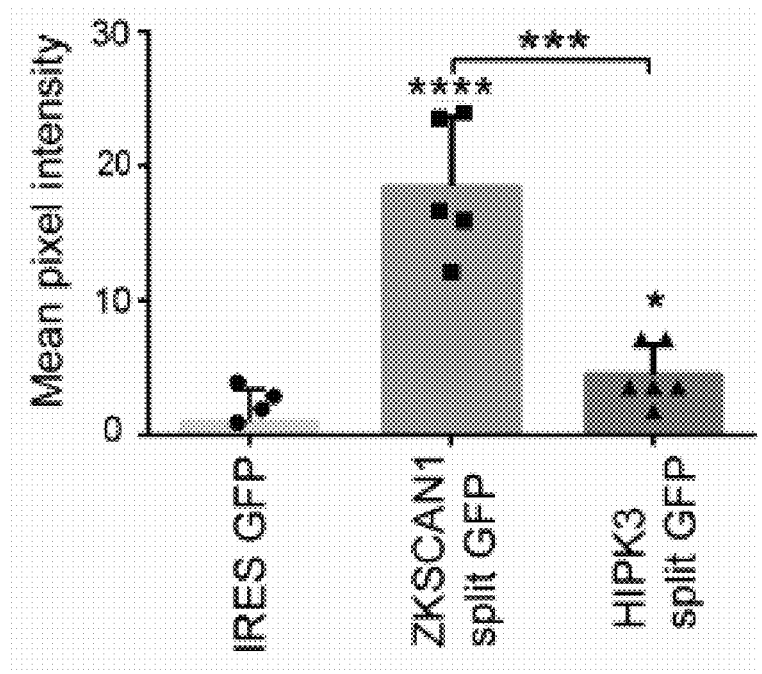
Figure 3C:
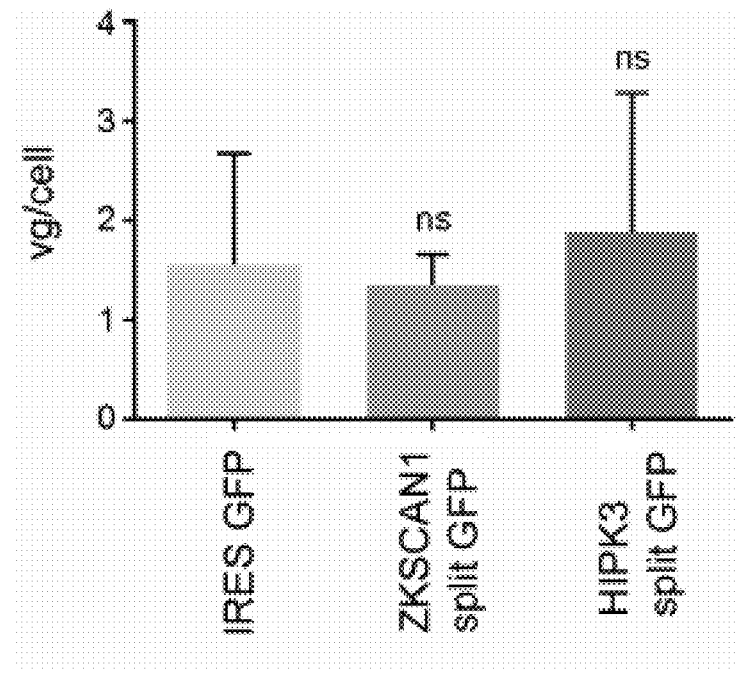
Figure 5:
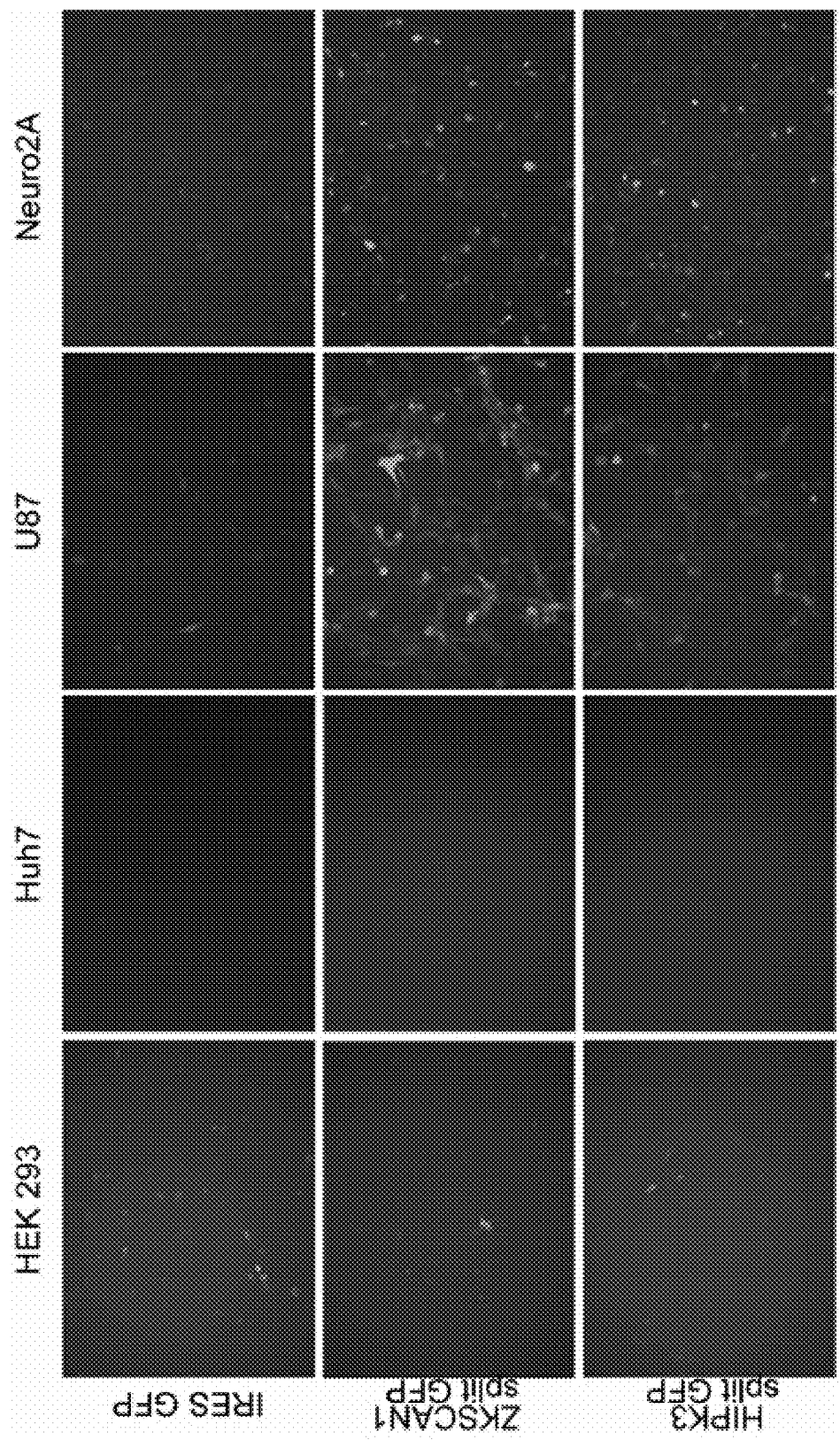
FIG. 5: circRNA expression in tissue culture models. Representative images of GFP fluorescence from HEK 293 (far left), Huh7 (middle left), U87 (middle right), or Neuro2A (far left) cells expressing IRES GFP (top), ZKSCAN1 split GFP (middle), or HIPK3 split GFP(bottom) after transduction with 100,000 vector genomes per cell of recombinant AAV2 vector.

In vitro characterization of circRNA expressing vectors. In order to verify the different cassettes, constructs were packaged into recombinant AAV2 vectors, a serotype which transduces most cells in culture. The viral vectors were used to transduce a variety of cell types (FIG. 5). Of these, the U87 human glioblastoma cell line showed the most robust expression and was selected for further analysis. In fluorescent images, the linear control showed the lowest expression, while the two circular cassettes showed roughly equal expression (FIG. 2A). This was verified by Western blot analysis of GFP expression (FIG. 2B, quantified in FIG. 2C). To characterize the constructs further, RNA was extracted from cells and used to run a northern blot. When probed for GFP-containing sequences, the IRES GFP constructs showed one band at the expected size for the mRNA transcribed from this construct. In contrast, the two split GFP vectors contained two bands—one at a size corresponding to the unspliced pre-mRNA, and one at a size corresponding to the spliced circRNA (FIG. 2D). Quantification of the blot showed that the levels of circRNA produced from ZKSCAN1 split GFP and HIPK3 split GFP were not significantly different from each other, confirming the protein level results (FIG. 2E). Interestingly, the level of circRNA was not significantly different from the IRES GFP RNA. This suggests that the linear IRES-containing RNA was translated at a lower efficiency than the circular RNA, perhaps due to interference between cap-dependent and IRES-mediated translation. These cell culture experiments validated that our vectors could be successfully packaged into AAV for delivery and expression of translatable circular RNAs.

circRNA expression after intravenous delivery. It is known that effects seen in cell culture do not always recapitulate events in vivo. Therefore, we next tested our constructs in mice. Constructs were packaged into recombinant AAV9 vectors, a serotype known to transduce well in vivo. As a first test, mice were injected intravenously with the viral vectors, and cardiac tissue was harvested for analysis. Immunohistochemical staining against GFP was performed to determine the relative level and localization of GFP expression. The control, linear IRES-GFP construct showed no GFP positive cells in cardiac tissue, which was a surprising result. However, the two circRNA vectors showed expression in cardiomyocytes throughout the heart. ZKSCAN1 split GFP showed robust expression, with a large amount of GFP-positive muscle cells. HIPK3 split GFP tissue also had GFP-positive cells, although fewer than seen with the ZKSCAN1 introns (FIG. 3A). This was confirmed by mean pixel intensity analysis of stained sections (FIG. 3B). We further verified that differences in expression were not due to dosing, as all animals received equivalent numbers of vector genomes (FIG. 3C).

Figure 3D:
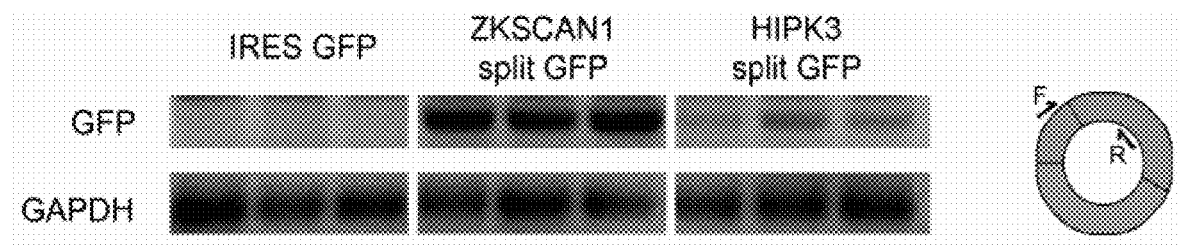
Figure 3E:
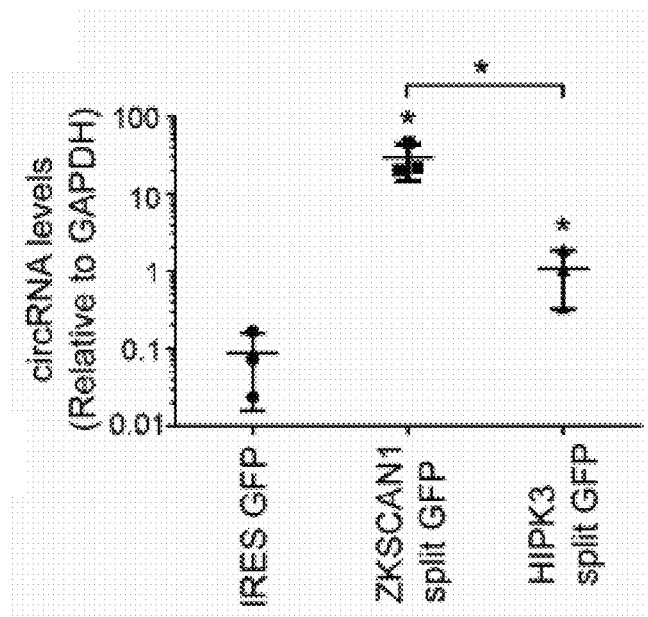
Figure 3F:
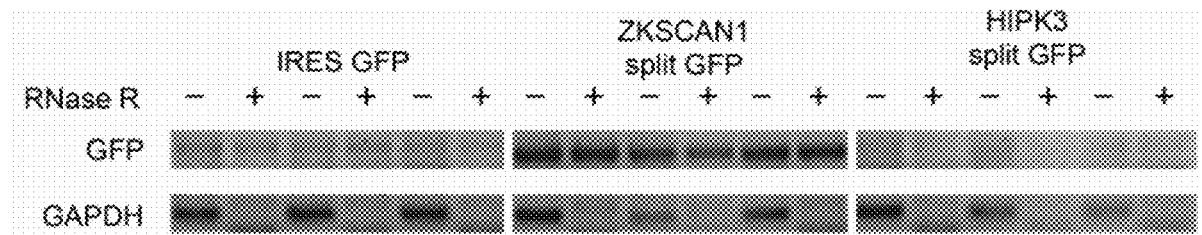

To assess expression at the RNA level, RT-PCR was performed with primers amplifying across the circRNA splice junction (note that these also amplify the IRES GFP RNA). By this analysis, no band was detected for the IRES GFP RNA, although both split GFP constructs showed expression of the circRNA (FIG. 3D). To examine the expression with greater sensitivity, quantitative RT-PCR was performed on the same samples. By this analysis, IRES GFP RNA expression was detectable, although at extremely low levels. In contrast, ZKSCAN1 split GFP and HIPK3 split GFP showed robust expression at levels comparable or higher to GAPDH in cardiac tissue. There was 27-fold higher expression from the ZKSCAN1-driven construct than the HIPK3-driven construct (FIG. 3E). As both vectors should be transcribed and translated with equal efficiencies, this suggests that the ZKSCAN1 intron sequences drive circularization with higher efficiency than the HIPK3 introns in cardiac tissue. Finally, an RNAse R assay was performed, and the RT-PCR bands for both split GFP vectors were resistant to its cleavage, evidence of their circularity (FIG. 3F).

Figure 6:
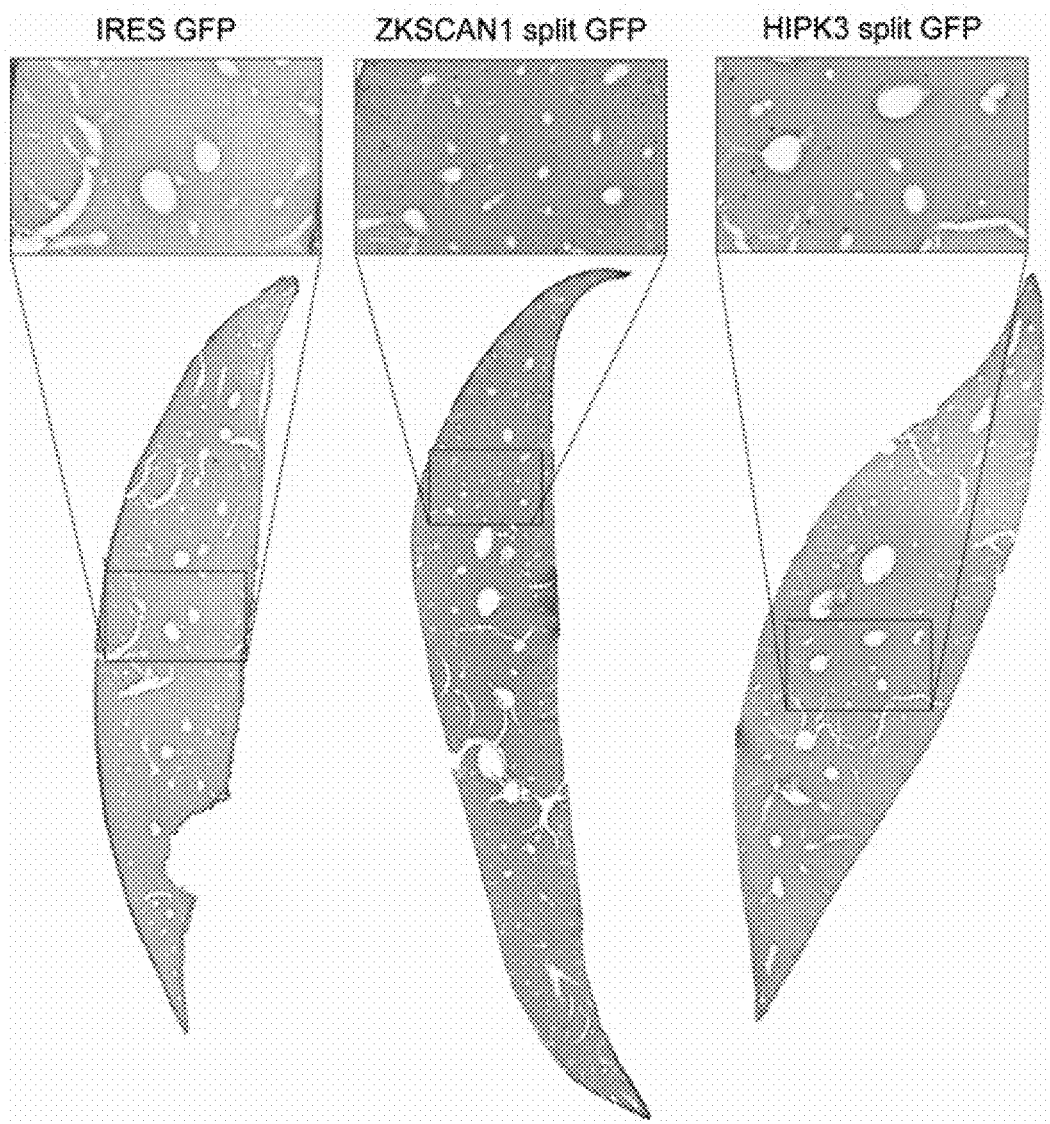
FIG. 6: circRNA expression in murine liver. The indicated constructs were packaged in to recombinant AAV9 vectors and injected intravenously into C57/BL6 mice at a dose of 5.5e11 vector genomes per animal, and then harvested four weeks post injection. Liver tissue was sectioned, followed by immunohistochemical staining to visualize GFP expression.

We next wanted to see if these circRNA expression vectors would show expression in other tissue types. From the same injections as above, liver tissue was harvested and processed. Immunohistochemical staining for GFP was performed, revealing that all constructs displayed extremely low expression levels in the liver. Of the three, ZKSCAN1 split GFP showed the most expression, followed HIPK3 split GFP, and then IRES GFP. However, the differences were not large as all three were near background (FIG. 6). Since AAV9 is vector known to transduce liver well, this effect is not due to vector tropism. Therefore, it also matched our cell culture data (FIG. 5, Huh7 cells). This is a somewhat surprising result, as previous work has shown that the endogenous ZKSCAN1 circRNA is expressed in liver. There are two possible explanations: first, the vectors may not circularize well in liver, perhaps due to using only a small portion of the intron for circularization. Second, the EMCV IRES may not be driving translation at high levels, as previous work has shown it has low liver expression compared to other IRESes.

Figure 4A:
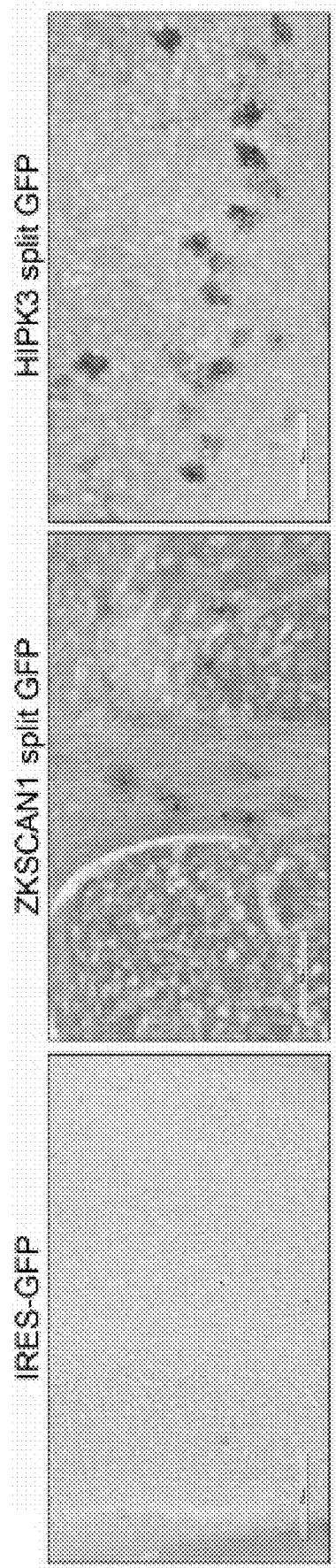
FIGS. 4A-4E: circRNAs are expressed in tissues of the central nervous system. (4A) The indicated constructs were packaged into recombinant AAV9 vectors and injected into the left cerebral ventricle of C57/BL6 mice at a dose of 3.989e10 vector genomes per animal, and then harvested six weeks post injection. GFP expression was visualized by staining brain sections immunohistochemically. Representative images of the cortex are shown. (4B) Quantitation of the GFP-positive cells in the samples shown in (4A). (4C) The indicated constructs were packaged into recombinant AAV9 vectors and injected intravitreously into C57/BL6 mice at a dose of 1e10 vector genomes per animal, and then harvested four weeks post injection. Representative images of the sectioned retina are shown. Green: immunofluorescent staining for GFP. Blue: DAPI staining of cell nuclei. (4D) Quantification of GFP expression by mean corrected fluorescence. (4E) RNA was extracted from injected retinas, and quantitative RT-PCR was performed with a primer set amplifying across the backsplice junction.
Figure 4B:
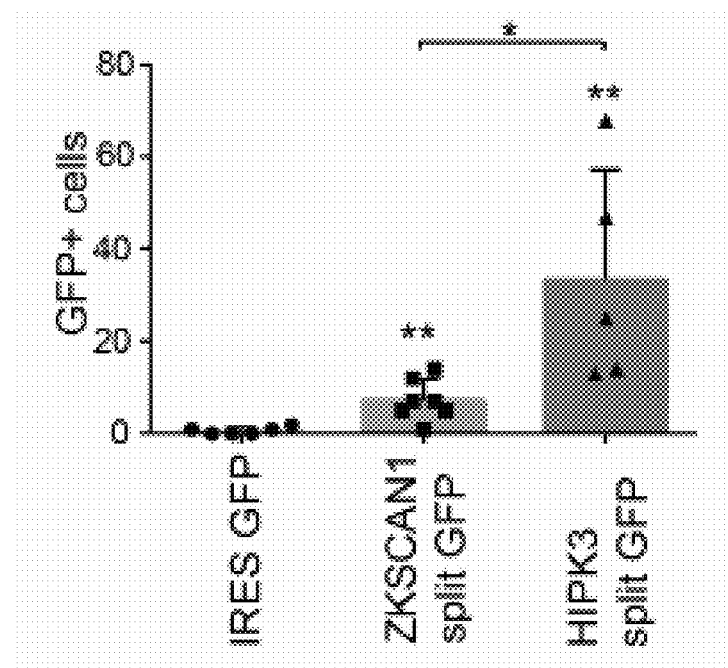
Figure 7A:
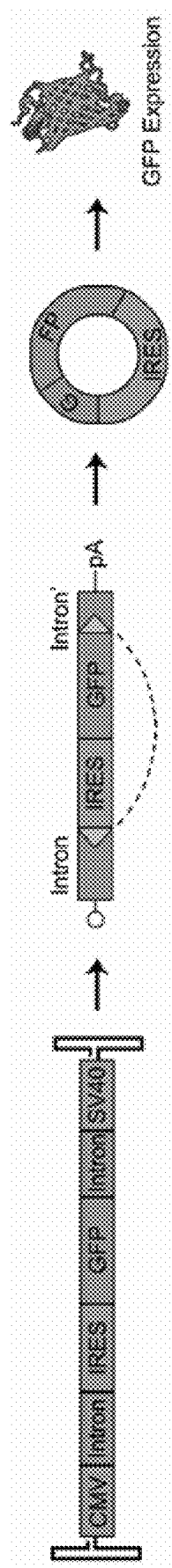
FIGS. 7A-7F: Comparison of split and unsplit circRNA expression vectors. (7A) The precursor split GFP transcript contains a split GFP cassette flanked by intron sequences derived from the human ZKSCAN1 or HIPK3 genes. Donor and acceptor splice sites are represented by grey triangles and the dotted lines indicate the backsplice pattern. (7B) Representative images of GFP fluorescence from U87 cells expressing ZKSCAN1 GFP (top), or ZKSCAN1 split GFP (bottom) 4 days post transduction with 100,000 vector genomes per cell of recombinant AAV2 vector. (7C) Western blot detecting GFP or loading control Actin for lysates of U87 cells transduced as indicated above, quantified in (7D). (7E) RNA was extracted and quantitative RT-PCR performed with primers amplifying across the back-splice junction. (7F) The indicated constructs were packaged into recombinant AAV9 vectors and injected intravenously into C57/BL6 mice at a dose of 5.5e11 vector genomes per animal, and then harvested four weeks post injection. Cardiac tissue was sectioned, followed by immunohistochemical staining to visualize GFP expression.
Figure 7B:
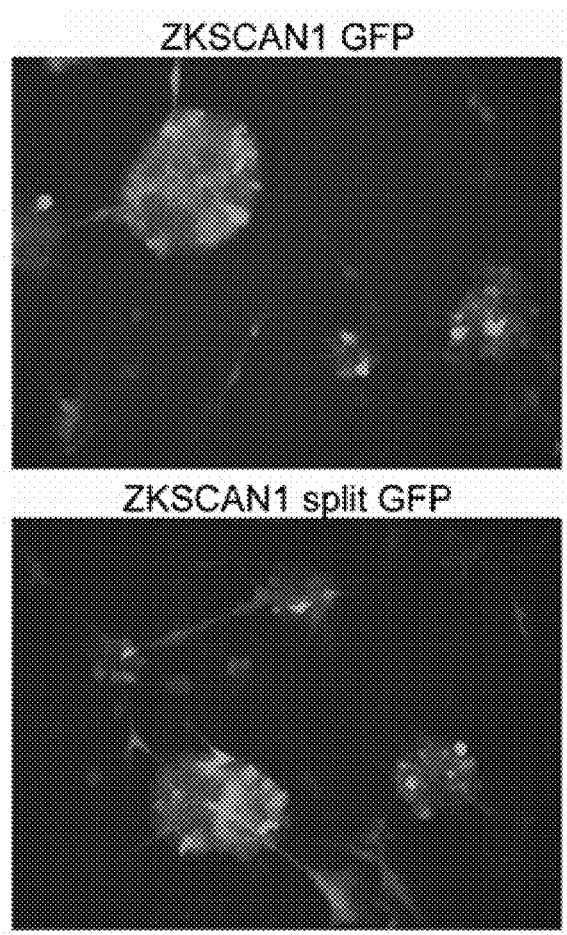
Figure 7C:
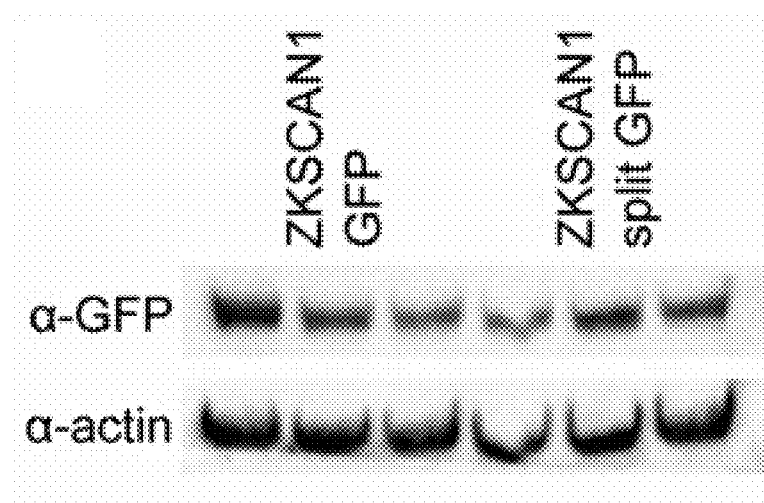
Figure 7D:
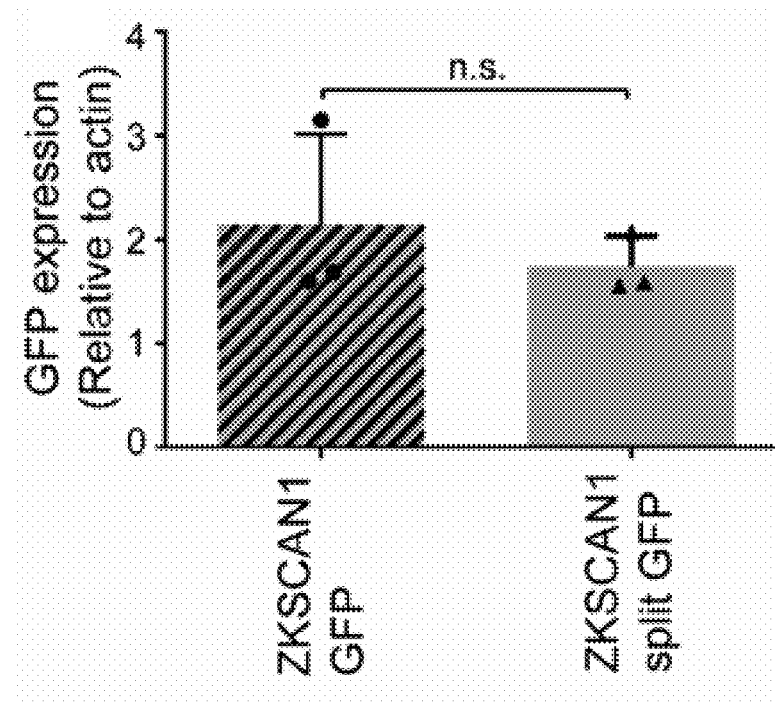
Figure 7E:
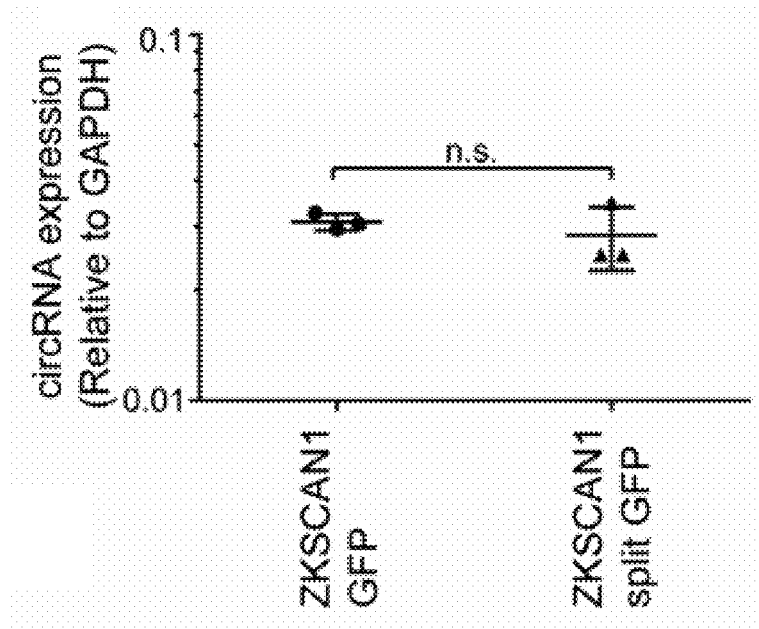
Figure 7F:
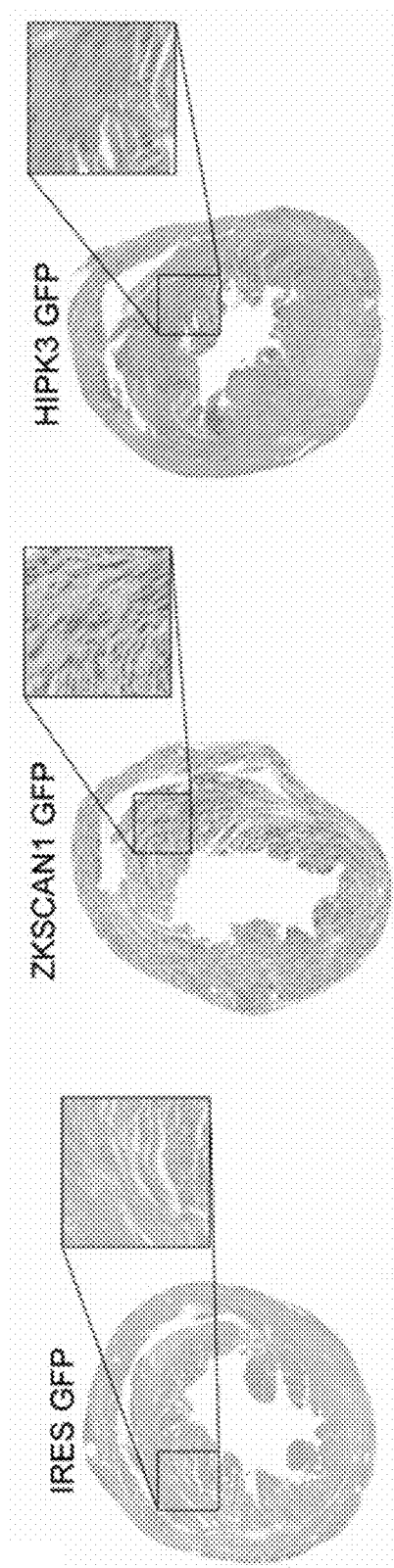

Split GFP vectors are an accurate representation. Although these expression vectors create circular products, the unspliced pre-mRNA is still found at appreciable levels, at least in cell culture (FIG. 2C). In addition, although we have used a split reporter thus far to show only circle-specific protein expression, to extend this system to other proteins of interest, it would be advantageous to use an unsplit ORF. In this case, it is possible that protein could be expressed from the linear unspliced RNA as well. To test this, we created another version of the ZKSCAN1 reporter in which the GFP open reading frame was not split. This reporter contains the IRES-GFP cassette flanked by the intron sequences (FIG. 7A). This vector, termed ZKSCAN1 GFP, was packaged into a rAAV2 vector for initial cell culture tests. In U87 cells, the GFP fluorescence from ZKSCAN1 GFP and ZKSCAN1 split GFP did not appear significantly different (FIG. 7B); this was confirmed by western blot analysis (FIG. 7C, quantified in FIG. 7D). We also confirmed that the RNA levels from both vectors were not significantly different (FIG. 7E). Since the levels of circRNA and protein were equal between the two vectors, this implies that there is no significant translational contribution from the pre-mRNA. We then created an unsplit version of HIPK3 GFP as well. Both constructs were used to create recombinant AAV9 vectors and injected intravenously to determine cardiac tissue expression. Results with the split GFP constructs recapitulated those with the linear GFP constructs. Both ZKSCAN1 GFP and HIPK3 GFP showed robust expression in the heart, with ZKSCAN1 GFP having a higher level of expression (FIG. 7F). The level and extent of expression in these constructs was not appreciably different from the split versions, indicating that our split GFP reporter vectors show representative expression.

circRNA expression in the nervous system. From both our cell culture experiments and published data on circRNA expression, tissues of the nervous system appear to have high circRNA expression. Therefore, we injected the viral vectors into the left cerebral ventricle of mouse pups. Brains were harvested, and again immunohistochemical staining performed to visualize GFP expression. The control IRES GFP cassette showed no expression in the brain (FIG. 4A). Both split GFP vectors showed expression in the brain, although limited to the cerebral cortex. This region-specific expression is likely circRNA specific (due to either circularization or IRES-mediated translation), as AAV9 vectors are known to express pan-regionally in the brain. In addition, GFP expression was predominantly astrocytic, with little neuronal expression detected. In contrast to the previous experiments, HIPK3 split GFP expressing tissue had more GFP positive cells than ZKSCAN1 split GFP expression tissue in the brain (FIG. 4B). This is evidence for tissue-specific differences in the ability of intron sequences to drive circularization.

Figure 4C:
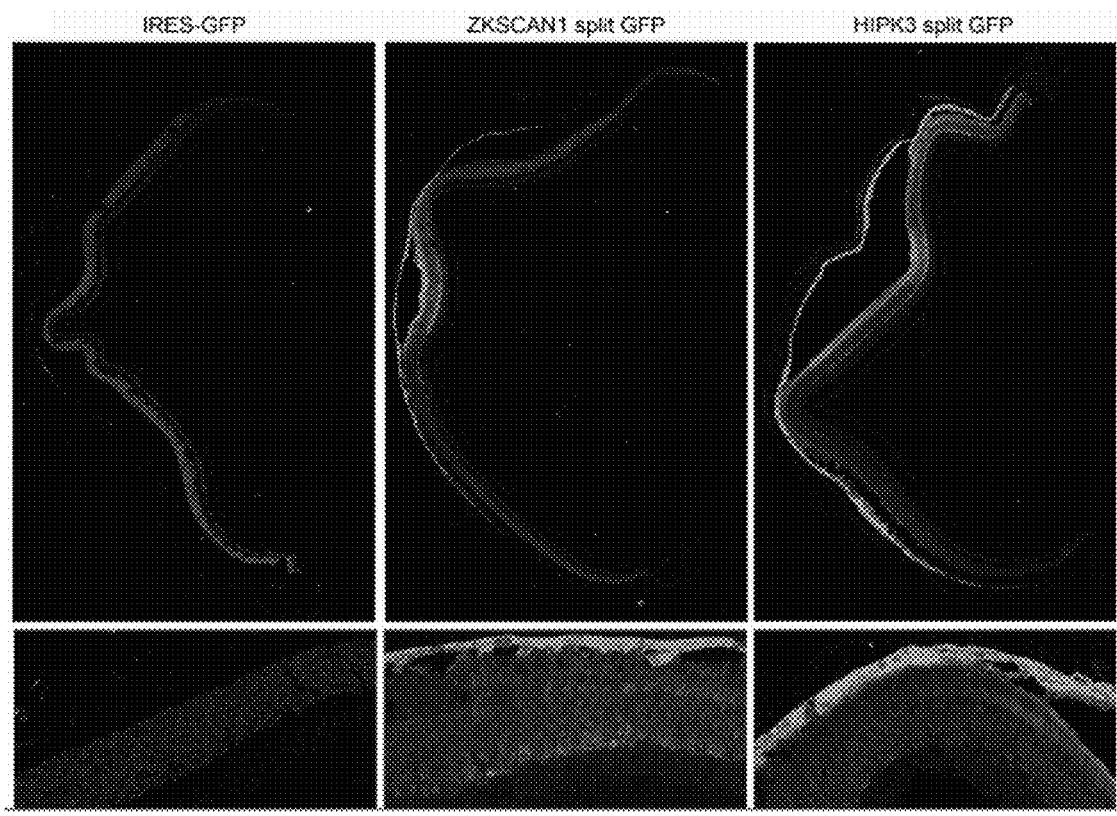
Figure 4D:
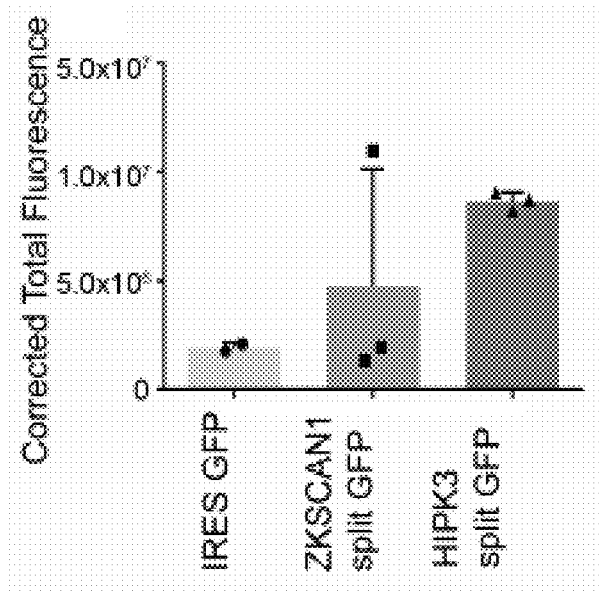
Figure 4E:
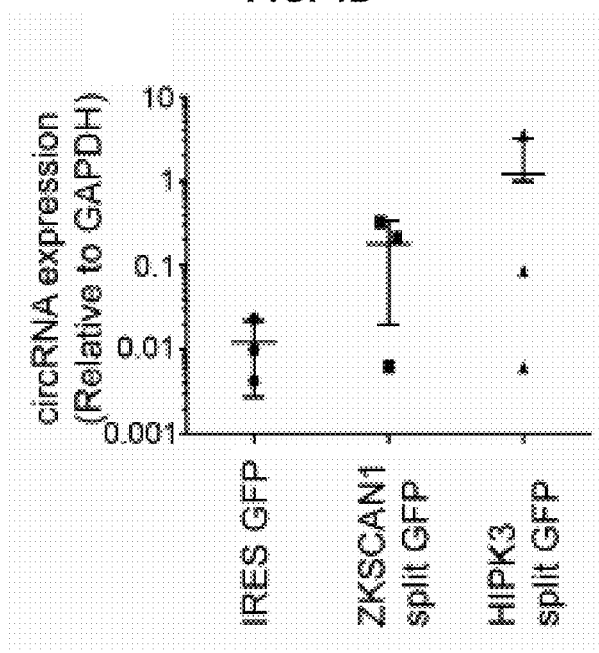

The final tissue we tested for expression was the retina of the eye. The same rAAV9 vectors were injected into the vitreous of the mouse eye. The eyecups were removed and the retinas sectioned, followed by immunofluorescence to visualize the expression. Again, the IRES GFP construct showed no detectable GFP expression, consistent with all other mouse tissues tested. However, both ZKSCAN1 split GFP and HIPK3 split GFP showed extensive GFP signal throughout the length of the retina (FIG. 4C, quantified in FIG. 4D). In this case, HIPK3-split GFP expression showed greater spread. In this context, GFP expression was found predominantly in the photoreceptor cells and the retinoid pigment epithelium, and not present in other cell types (see inset). RNA was extracted from a second cohort of injections for quantitative RT-PCR analysis (FIG. 4E). Although above background, the signal for IRES GFP RNA was extremely low, corroborating the protein-level data. Both ZKSCAN1 split GFP and HIPK3 split GFP showed a trend toward increased expression compared to IRES GFP, although not significant due to a possible outlier in each condition.

From these studies, we have shown that circRNAs can be used to express transgenes in a variety of tissue types. Although circRNAs have been predominantly shown to be expressed in tissues of the nervous system, our cassettes were also able to drive expression in cardiac tissue. However, little expression was seen in the liver, which is notable as AAV vectors are known to be targeted to the liver. Even within a tissue which showed circRNA expression, there were cell-type specificities. For example, in the brain, our vectors showed expression only in astrocytes, not neurons. This was surprising, as a number of studies have shown neuronal circRNA expression, and many circRNAs are thought to function in neuronal processes. Therefore, the cell types which circRNAs can express may be broader than what was previously known. In addition, expression in the eye was also targeted to certain cell types—specifically, the photoreceptors and retinoid pigment epithelium. The recombinant AAV vectors used in these studies were of a serotype that expresses throughout most tissues of the animal; however, many vectors have been generated with different tropism. Therefore, it would be of interest to test these circRNA expression constructs in different vectors as a two-factor system for specificity. Although the constructs used in this study showed tissue-specific differences in the level of expression compared to each other, we only tested two different intron pairs in the current work. Given the large numbers of known circRNAs identified in variety of studies, there are many more intron pairs that could be tested for their expression level and tissue specificity. Accordingly, it may be possible to create a toolkit of intron pairs with targeted expression for the desired tissue and cell type.

One of the distinguishing features of circRNAs is their increased stability compared to most linear mRNAs. In the current study, tissues were harvested at only a single time point for expression. However, with increased RNA stability, it is possible that the level of expression would increase over time in comparison to a linear message. Therefore, a time-course study would be of interest for future study. Additionally, the increased RNA stability may decrease the doses needed for robust expression. This is especially important as the high doses rAAV vectors often required for expression can induce inflammatory responses that lead to ablation of transgene expression. Therefore, in addition to a time-course study, a dose-comparative study is necessary to characterize the utility of circRNA expression vectors.

For the purposes of the current study, GFP expression was utilized as a proxy of circRNA expression. However, the viral IRES used may also restrict expression in certain cell types. Therefore, the extent of circRNA expression may be larger than seen here. It would be of interest to further study the effect of varying IRES sequences on protein-level expression. Aside from protein expression, there is scope for the use of circRNA vectors for the expression of functional RNAs. A variety of known noncoding RNAs could conceivably be expressed by our system, including lncRNAs. In addition, circRNAs have potential as a platform to express designer RNAs. These could include designer miRNA sponges (especially as endogenous circRNAs have been well characterized as miRNA sponges). In addition, RNAs could be designed with binding sites for RNA binding proteins in a variety of applications. Taken together, circRNAs represent a novel way to express both coding and noncoding RNAs in a variety of tissues and cell types.

Example 2

Figure 8:
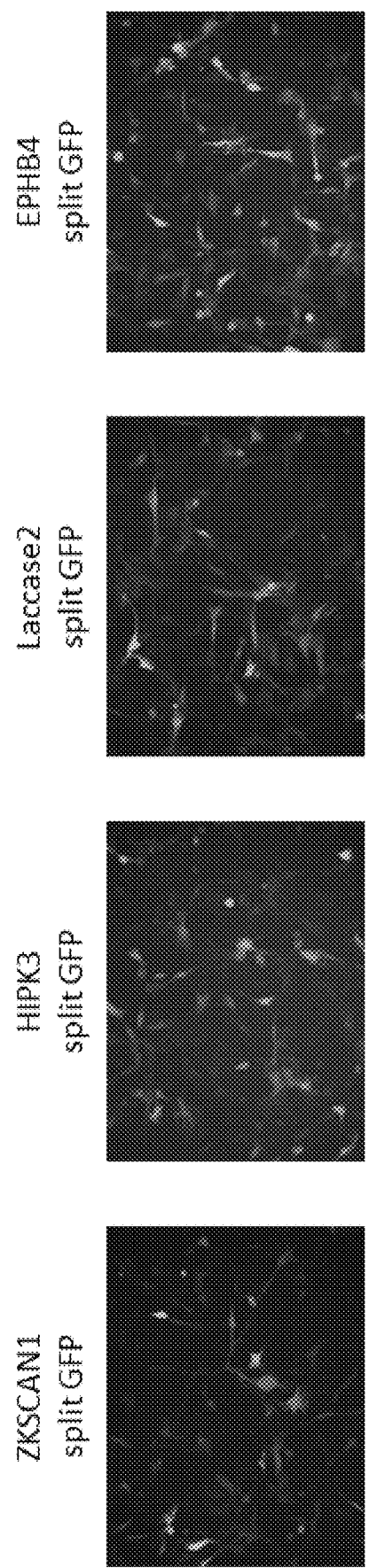
FIG. 8: Data showcasing the ability of different intronic elements to support circular RNA formation and translation. These data enable and corroborate modular design of circular RNA encoding constructs. CircRNA-producing cassettes were created with introns derived from the ZKSCAN1, HIPK3, Laccase2, and EPHB4 genes. These constructs were packaged into rAAV2 and used to transduce U87 cells at an MOI of 100,000 vg/cell. Images were taken on day 4.
Figure 9A:
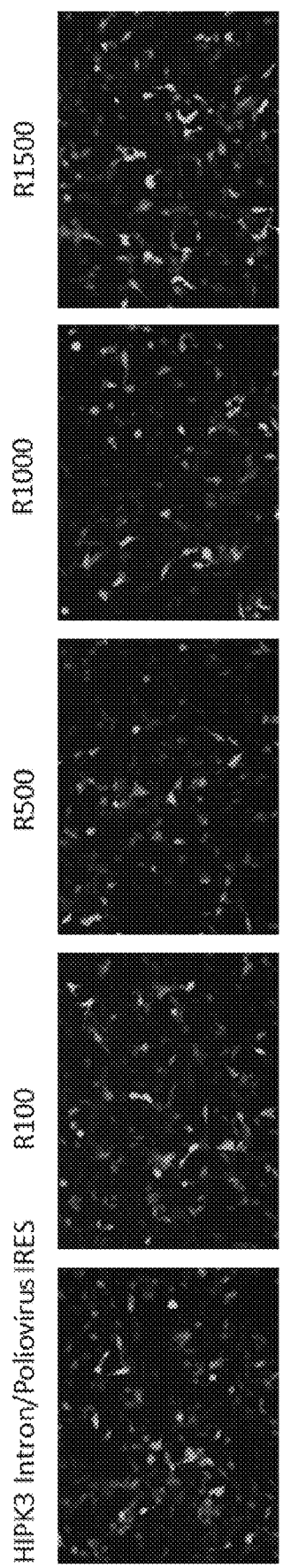
FIGS. 9A-9F: 3' (Right) Intron sequence tolerates insertions. Inserting sequence into the right intron of a circRNA-producing cassette does not reduce the amount of circRNA made. (9A) Representative fluorescence images. (9B) Western blot for GFP translated from circular RNA and control actin, data is normalized and quantified in (9C). (9D) Northern blot probed against GFP. Indicated is the circRNA band. (9E) quantification of northerns/circular RNA expression (9F) Schematic of RNA precursor encoded by AAV vector genome with insertions in the right (3') intron. Insertions of 100-1000 bases in length do not affect circular RNA levels or translation of GFP from circular RNA. Insertion of 1500 bases improves circular RNA translation but not expression of circular RNA by 2 fold.
Figure 9B:
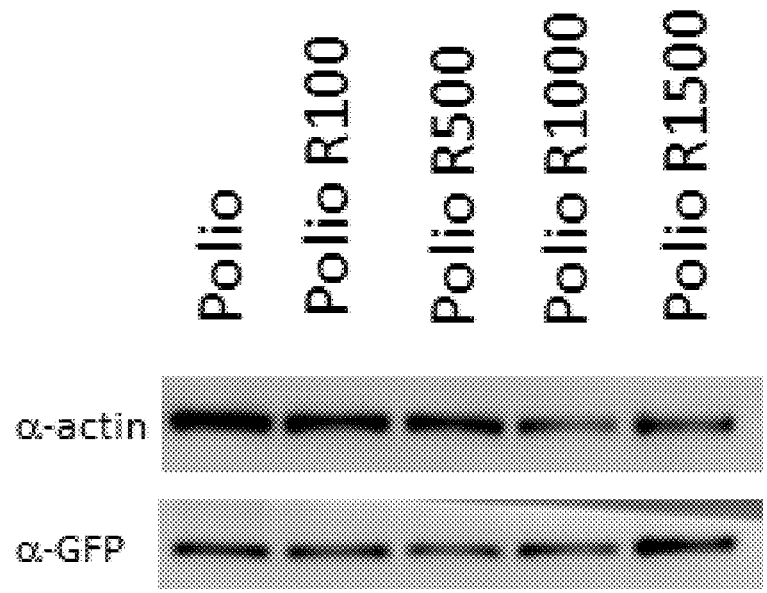
Figure 9C:
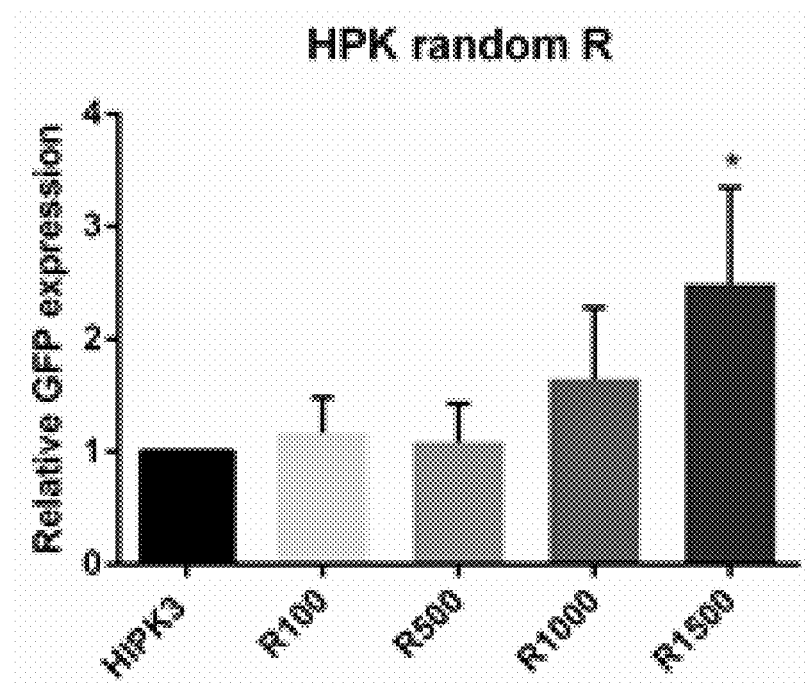
Figure 9D:
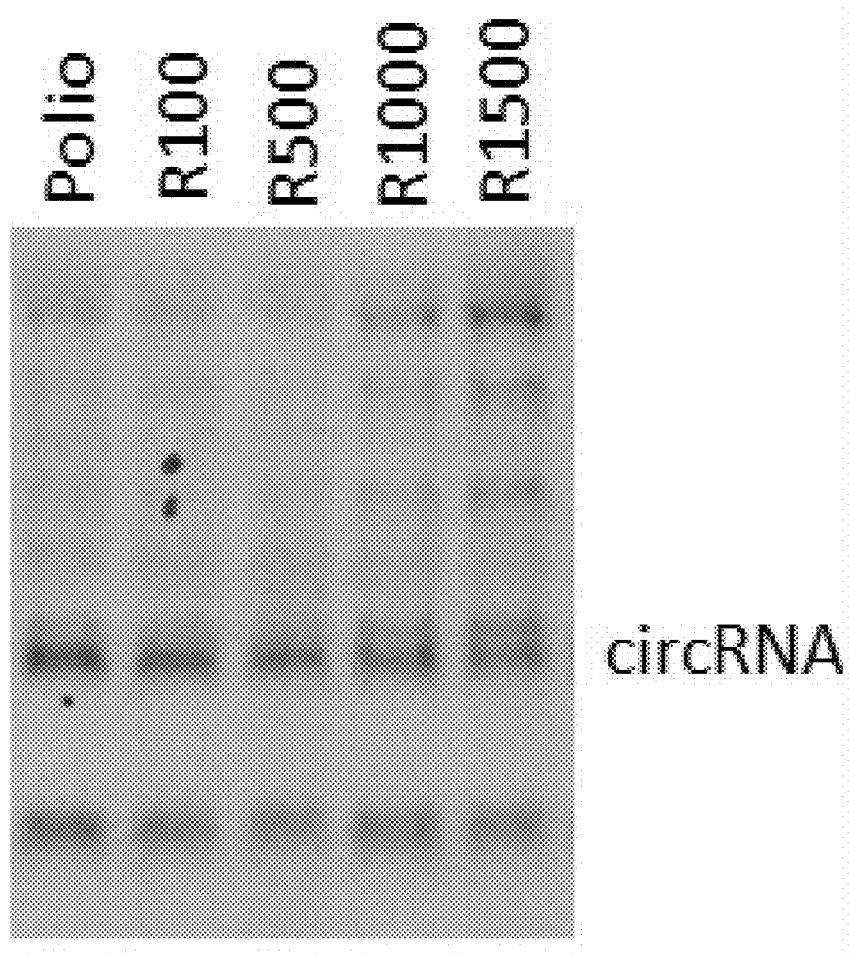
Figure 9E:
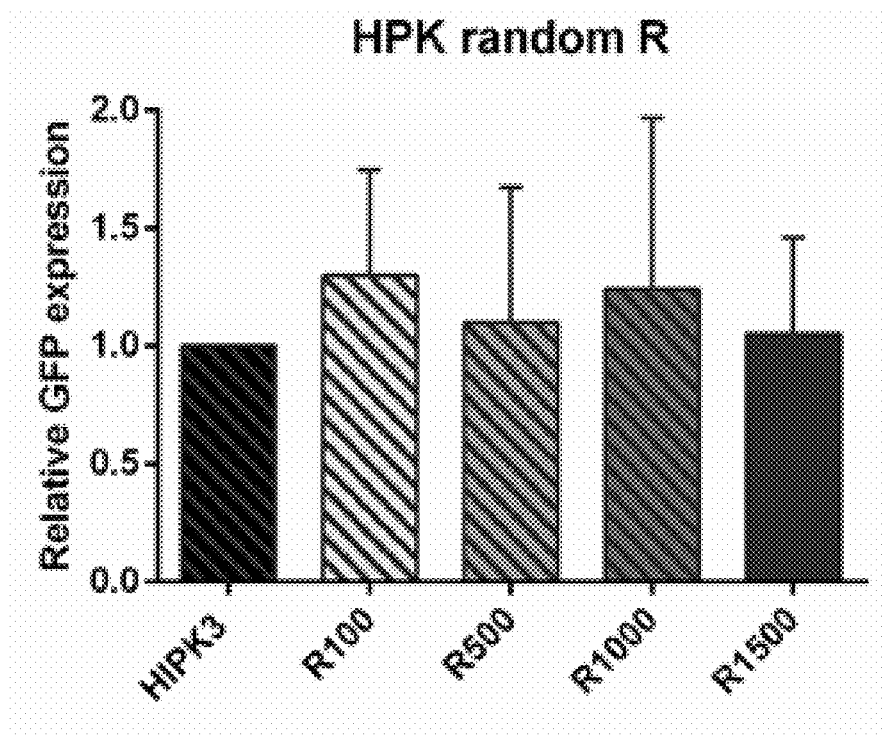
Figure 9F:
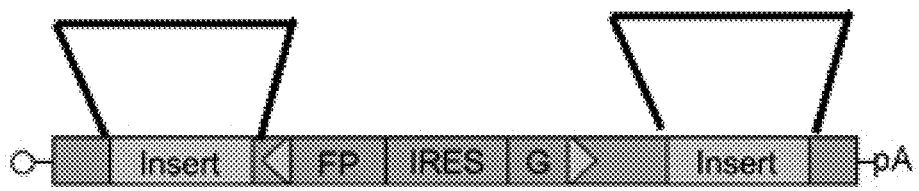
Figure 10A:
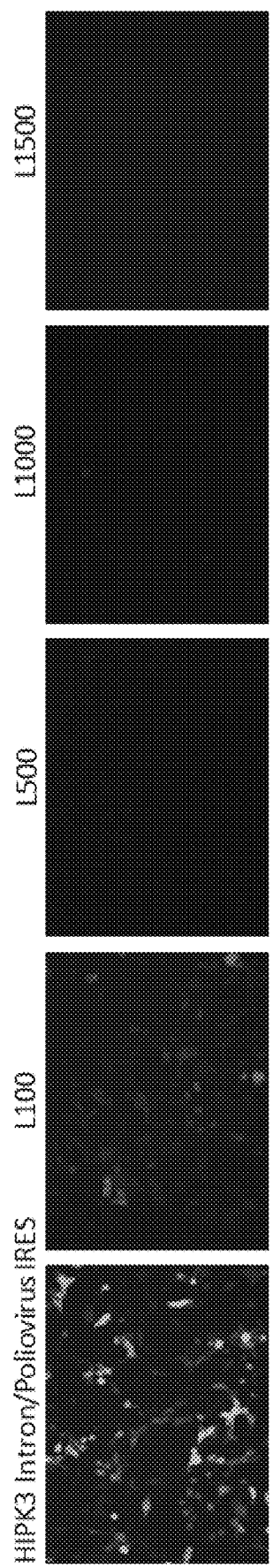
FIGS. 10A-10F: 5' (Left) Intron sequence does not tolerate insertions. Inserting sequence into the left intron of a circRNA-producing cassette reduces the amount of circRNA produced. (10A) Representative fluorescence images. (10B) Western blot for GFP and actin, quantified in (10C). (10D) Northern blot probed against GFP. Indicated is the circRNA band. (10E) quantification of Northern blots. (10F) Schematic of RNA precursor encoded by AAV vector genome with insertions in the left (5') intron. Insertions of 100-1500 bases in length markedly reduce circular RNA levels or translation of GFP from circular RNA.
Figure 10B:
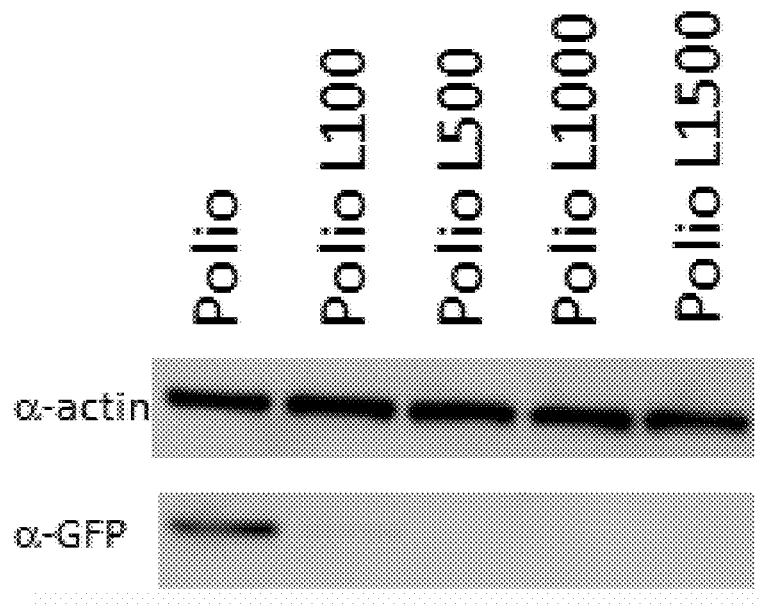
Figure 10C:
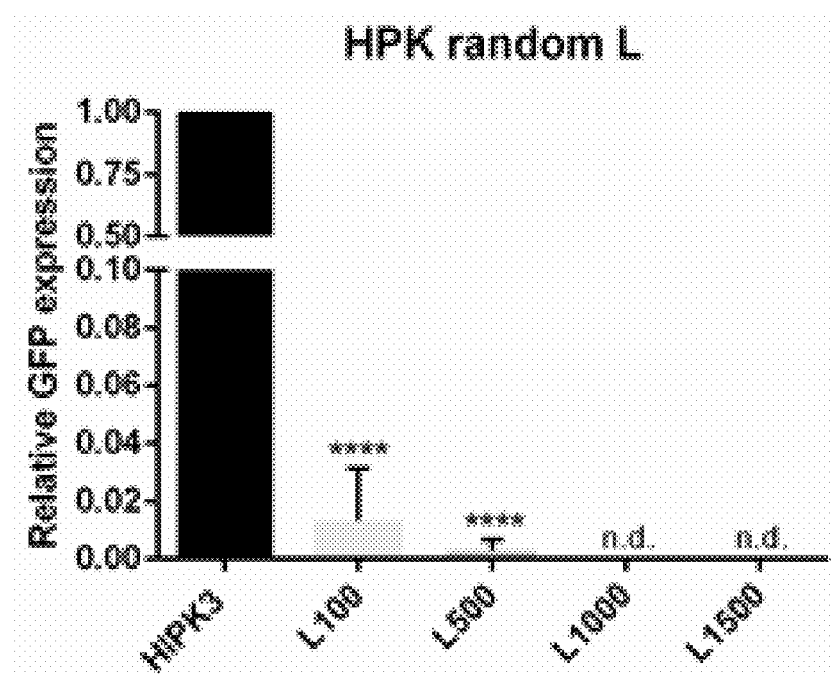
Figure 10D:
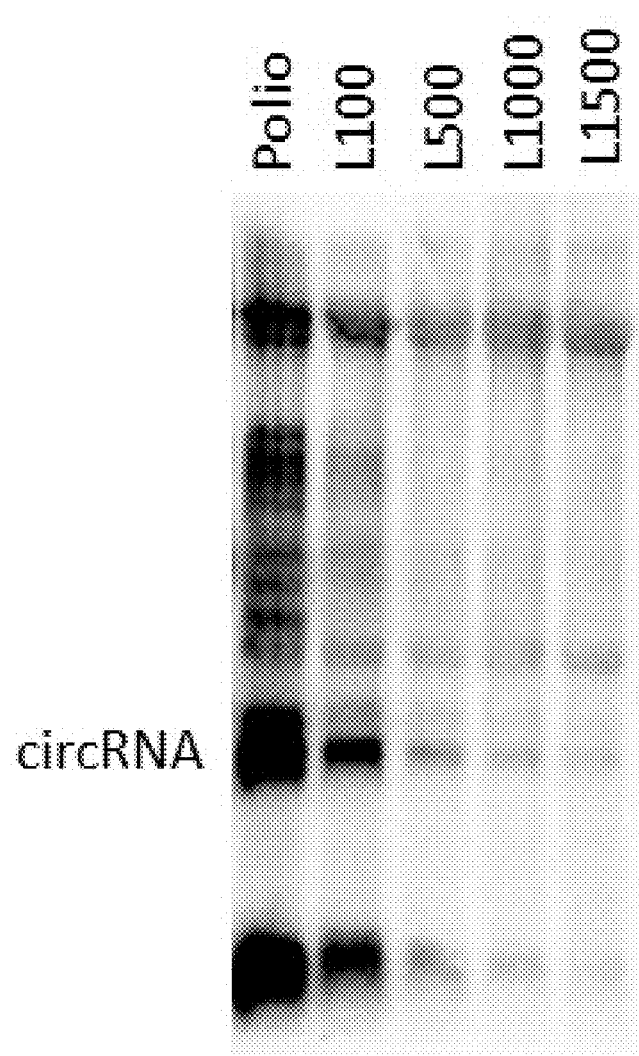
Figure 10E:
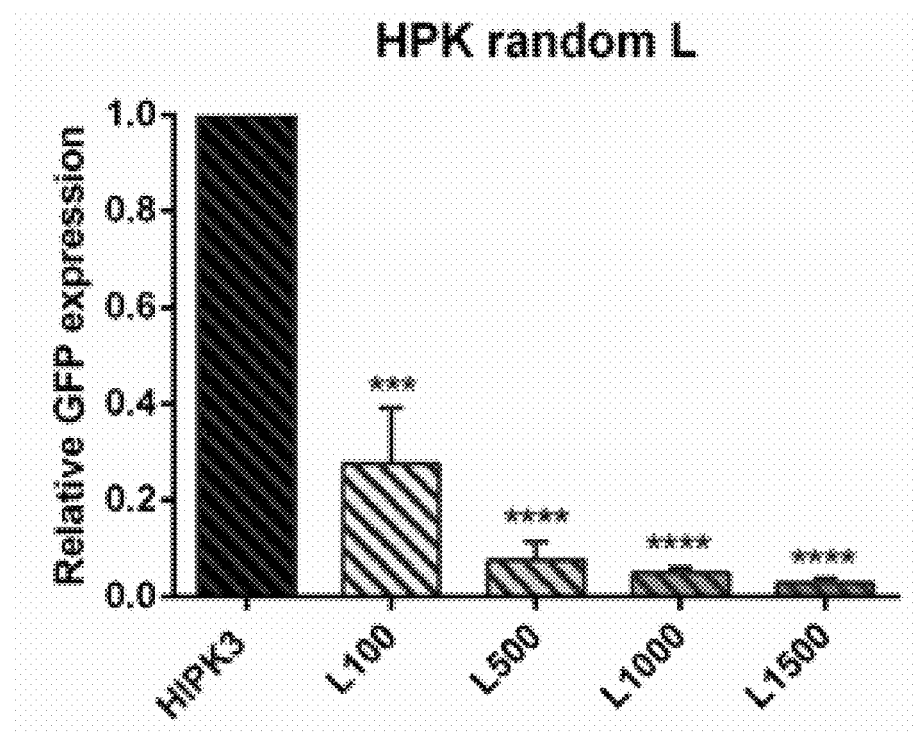
Figure 10F:
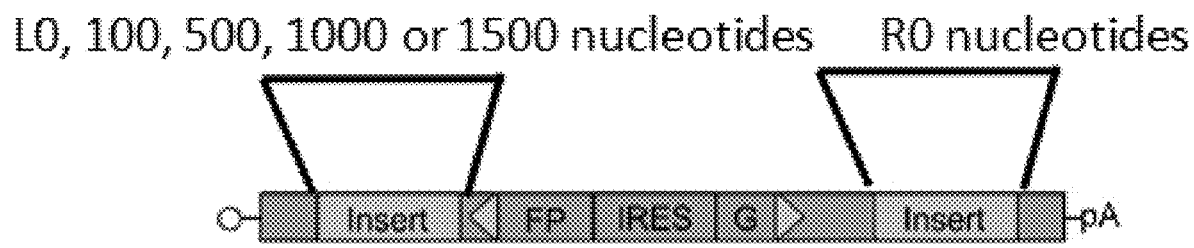
Figure 11A:
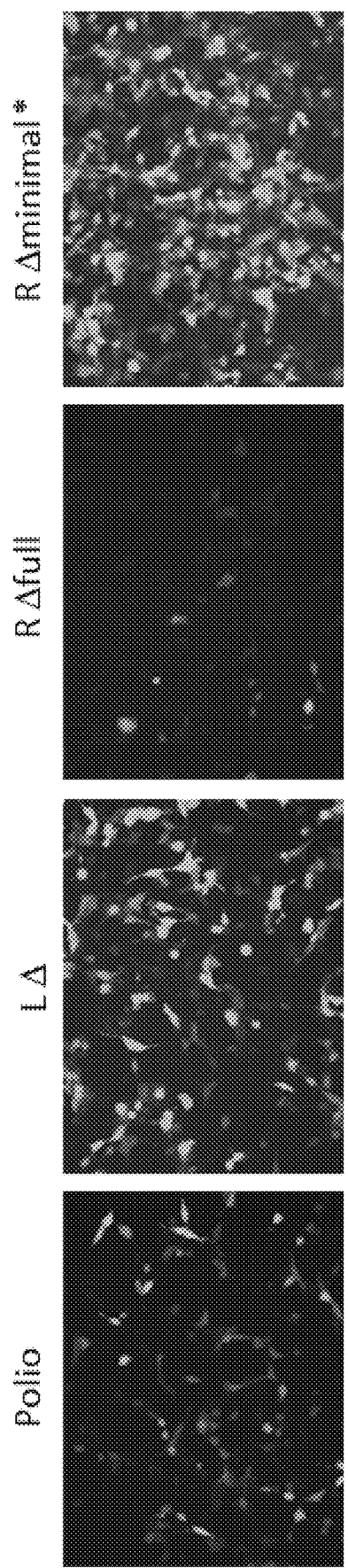
FIGS. 11A-11F: Deletion of intron sequences (preserving the Alu repeat element and splice acceptor/donor site) in the left intron leads to an increase in circRNA production. Full deletion of these sequences in the right intron ablates circRNA formation, but a smaller deletion is tolerated. (11A) Representative fluorescence images. (11B) Western blot for GFP and actin, quantified in (11C). (11D) Northern blot probed against GFP. Indicated is the circRNA band. (11E) Quantification of Northern blots. (11F) Schematic.
Figure 11B:
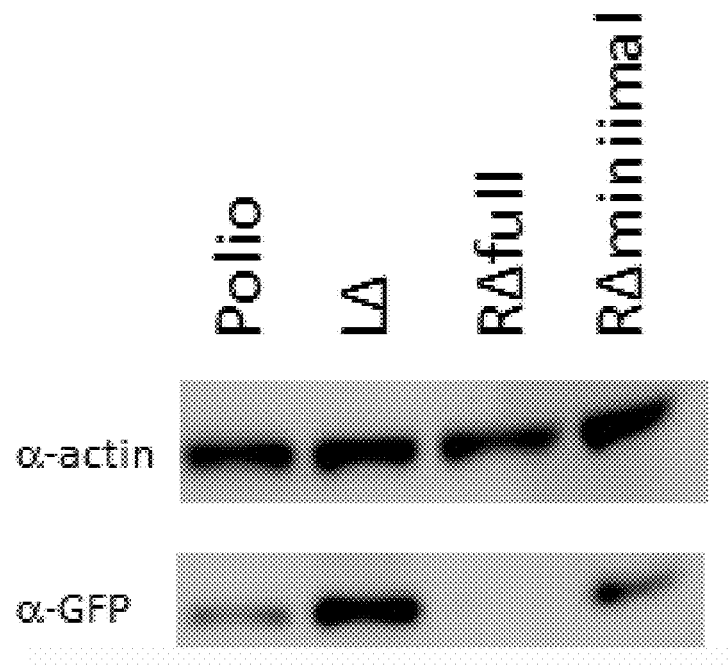
Figure 11C:
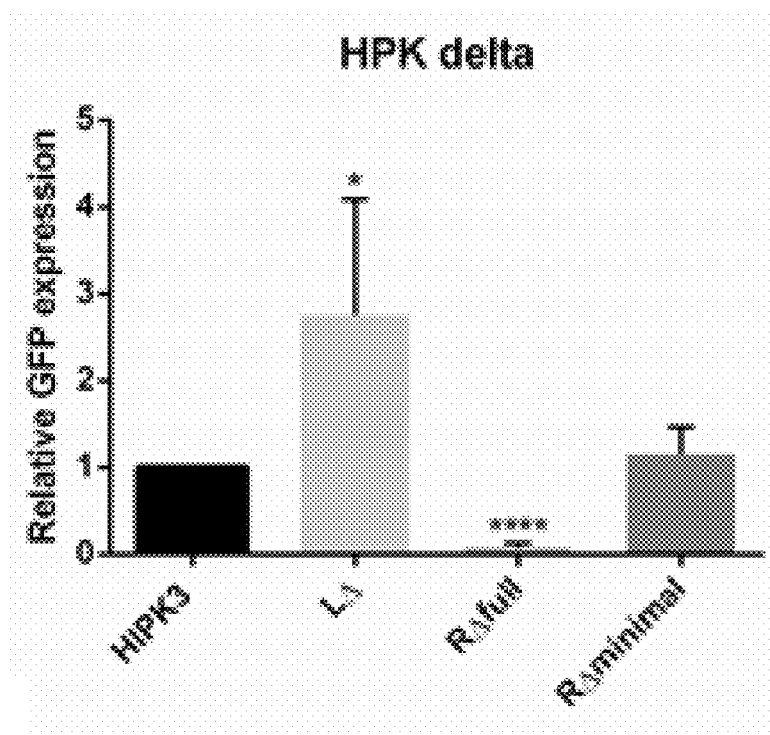
Figure 11D:
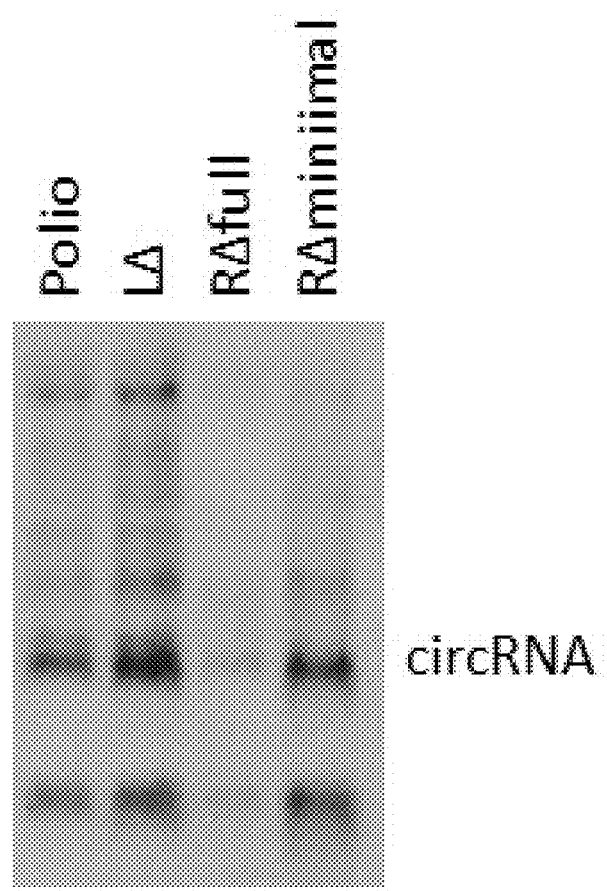
Figure 11E:
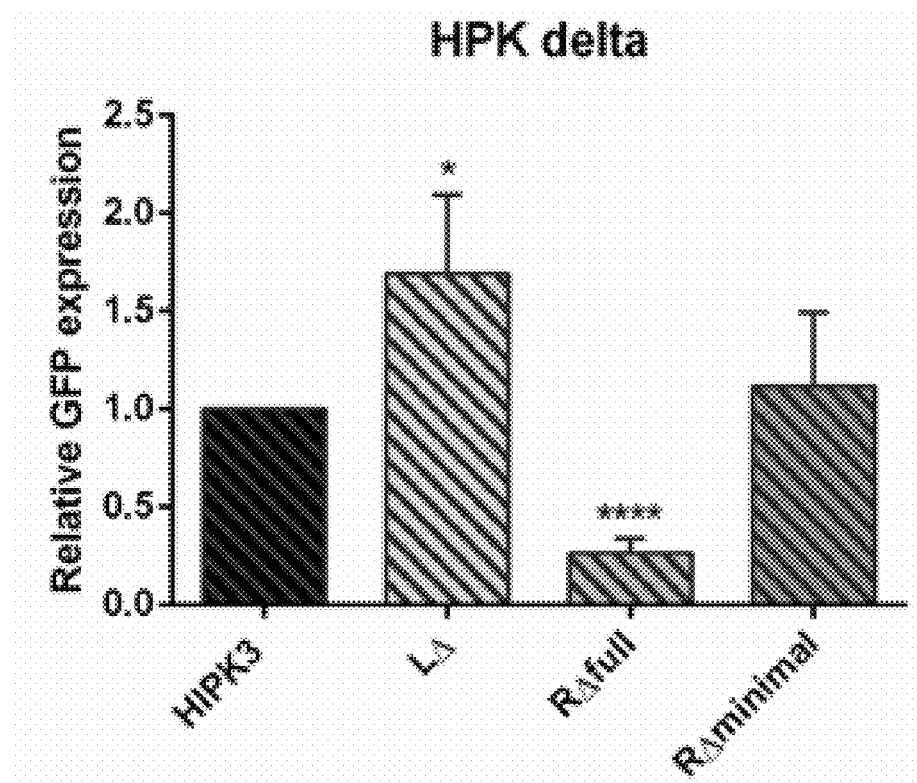
Figure 11F:
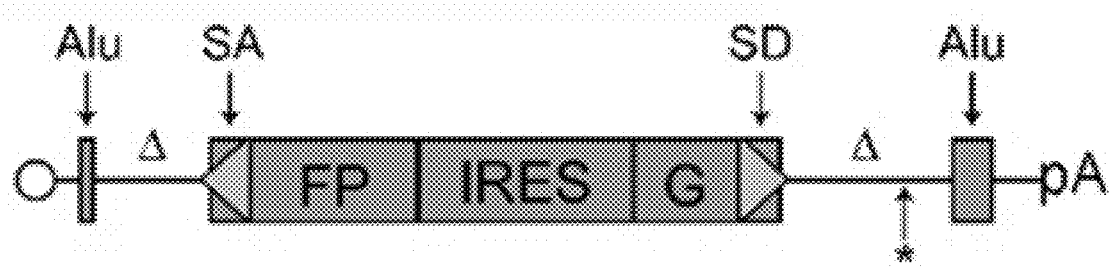
Figure 12A:
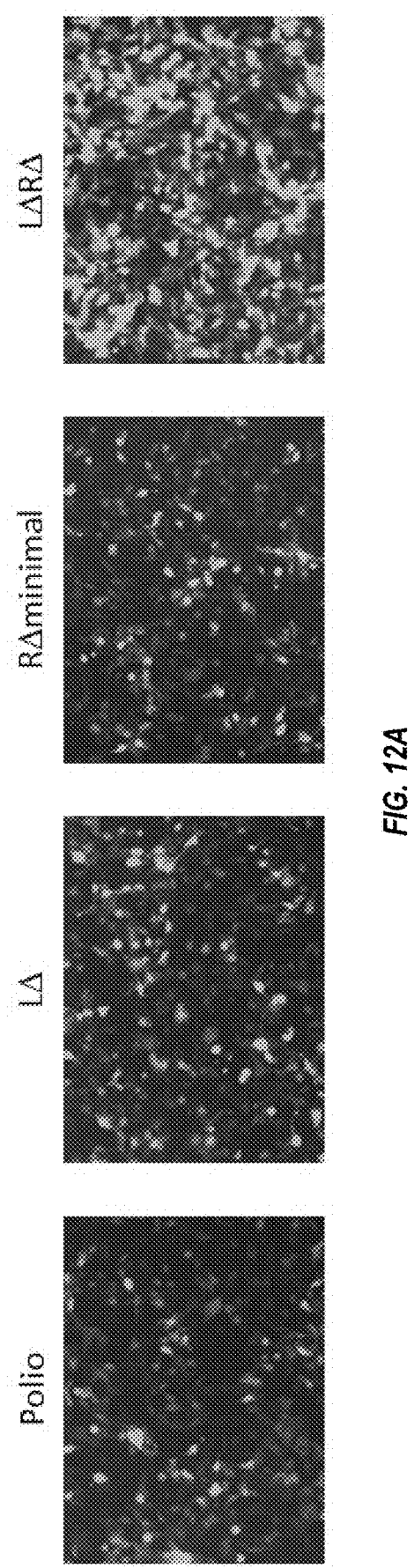
FIGS. 12A-12F: Combination of deletions in the left and right introns gives a construct with >5-fold increased circRNA production. (12A) Representative fluorescence images. (12B) Western blot for GFP and actin, quantified in (12C). (12D) Northern blot probed against GFP. Indicated is the circRNA band. (12E) Quantification of northern blots. (12F) Schematic.
Figure 12B:
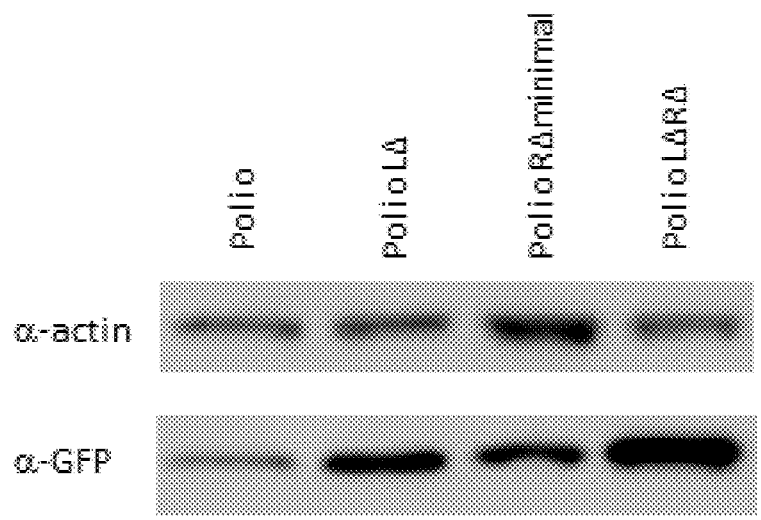
Figure 12C:
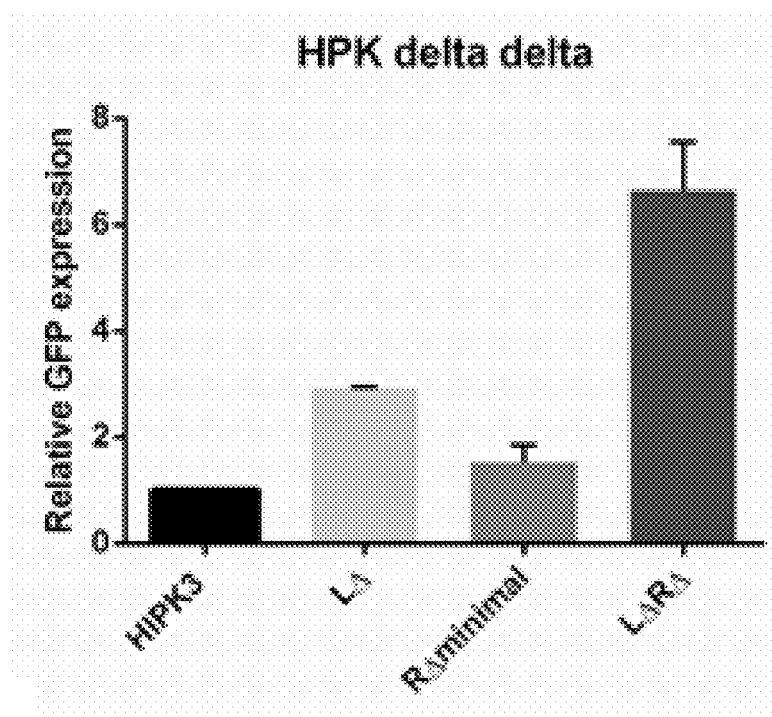
Figure 12D:
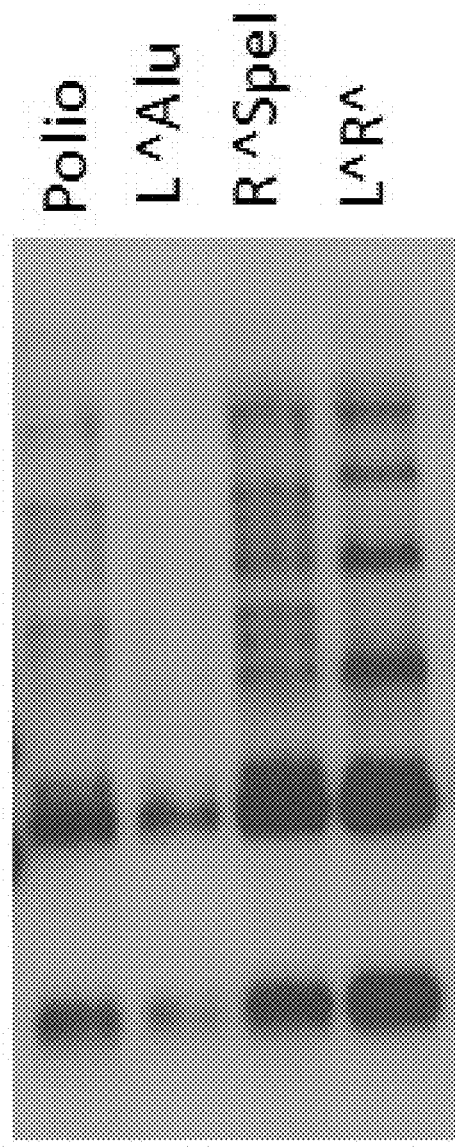
Figure 12E:
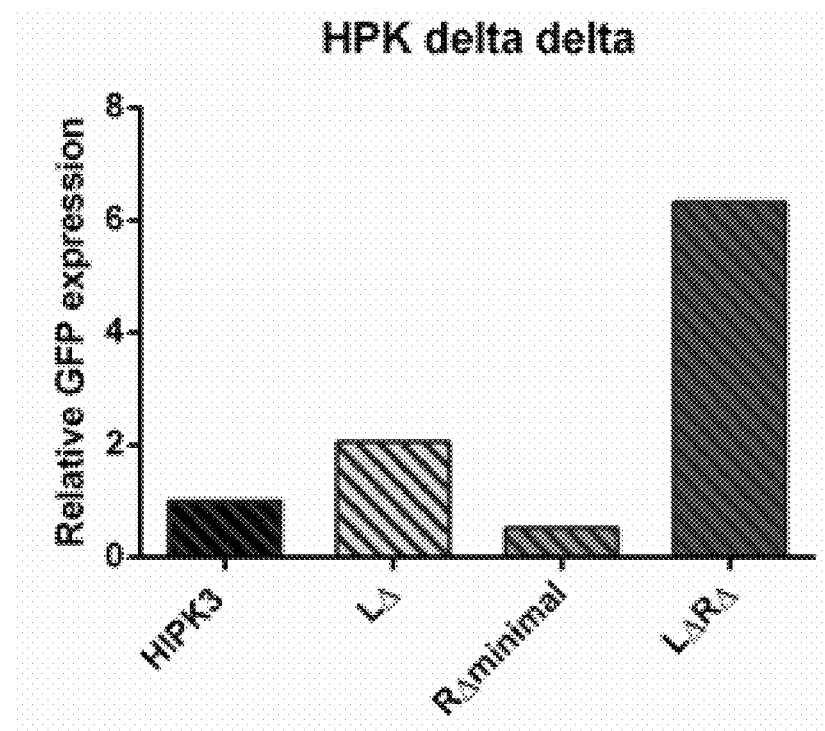
Figure 12F:
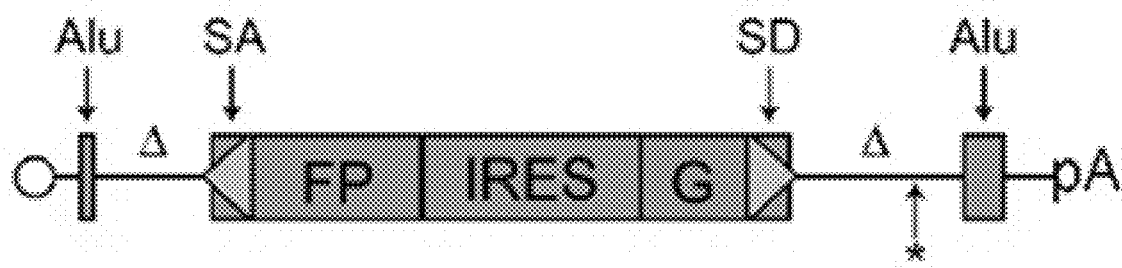
Figure 13A:
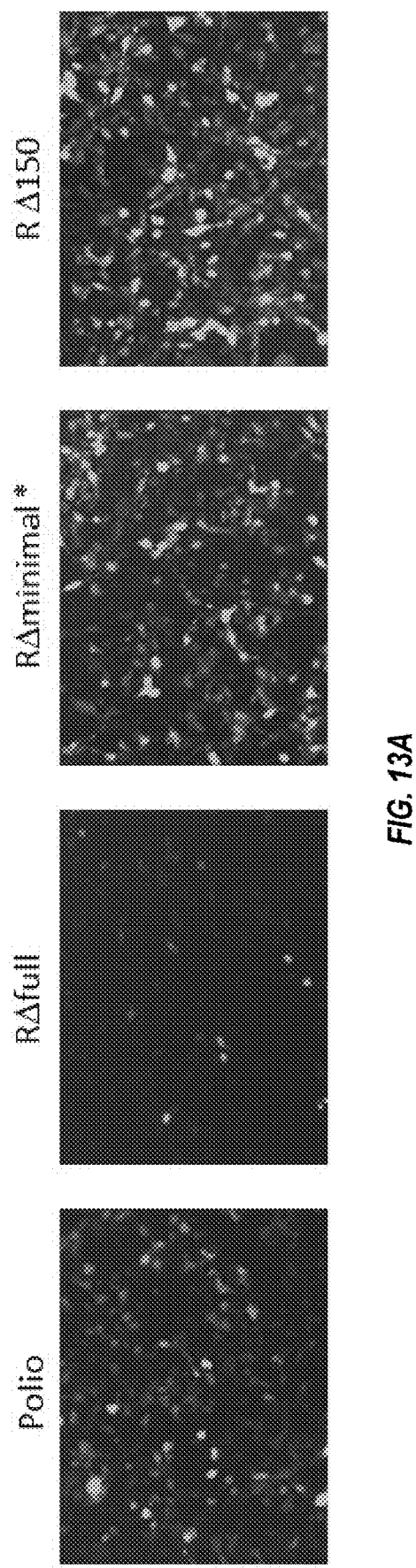
FIGS. 13A-13D: The difference between RΔfull and RΔminimal is not sequence-specific. A deletion with the same total length but different sequence remaining (RΔ150) is also tolerated. (13A) Representative fluorescence images. (13B) Western blot for GFP and actin, quantified in (13C). (13D) Schematic.
Figure 13B:
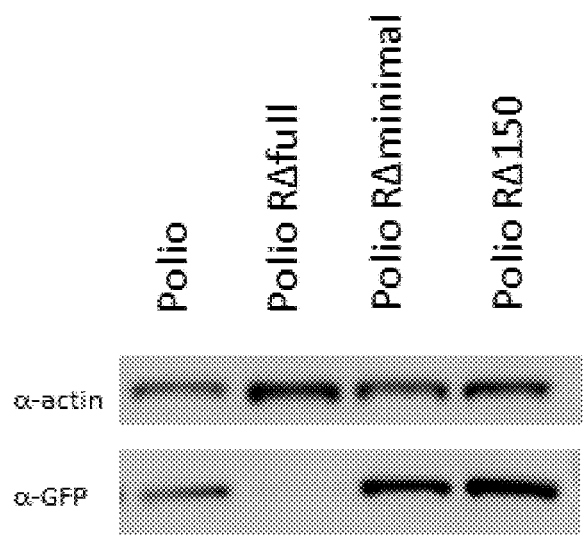
Figure 13C:
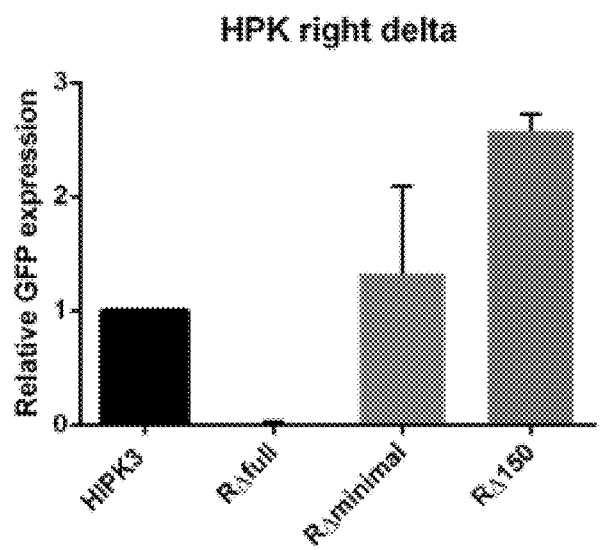
Figure 13D:
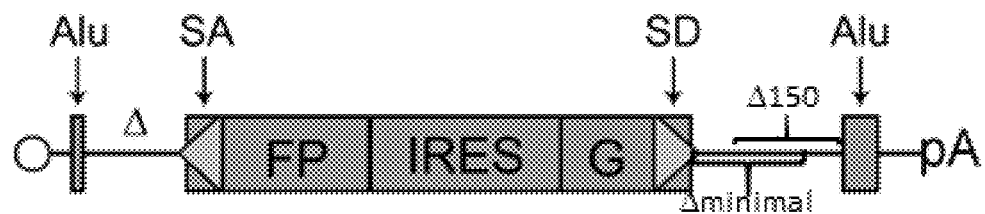

In order to investigate the intron requirements for back-splicing, we created a series of constructs varying the distance between the Alu element and the splice site on both introns (left and right). We first inserted sequence into the left intron; this was composed of randomized sequence with little base-pairing potential with a GC content matching that of the endogenous HIPK3 intron. A range of sizes from 100 bp to 1.5 kbp was inserted at a point 100 nt away from the splice site. These insertions had a large effect; the insertion of even 100 nucleotides dramatically reduced circle formation and GFP expression, whereas greater lengths abolished expression completely (FIG. 8).

We then created a second set of insertions into the left intron which were located 325 nts away from the poly-pyrimidine tract. These constructs showed the same effect (FIGS. 9A-9F), indicating that increased distance between the Alu element and the splice site in the left intron is detrimental for circular RNA formation. Importantly, we inserted randomized sequence into the right intron of the HIPK3 construct (FIGS. 10A-10F). The effect on the right intron was completely different than in the left intron. All insertions up to the maximal 1.5 kb were tolerated with no effect on circular RNA levels or GFP expression. Therefore, desired sequences could be inserted into the right intron without affecting circRNA formation. It is important to note that this allows multiplexing of different elements such as microRNA, other non-coding RNA within the right intron of the circular RNA constructs.

We next wanted to investigate shortening the distance between the Alu element and splice site. Therefore, we created deletions in both the left and right introns wherein all of the sequence between the Alu and splice site was deleted. On the left intron, we left all of the poly-pyrimidine tract. On the right intron, we deleted everything up to the consensus splice donor site. We also made a minimal deletion leaving another ~100 nt (about the same amount left for the poly-pyrimidine tract in the left intron). The left intron deletion was tolerated well; in fact, there was a 2-3 fold increase in circRNA levels and GFP expression. This agreed with the results that increased distance was detrimental (FIGS. 8, 9A-9F). However, the full deletion in the right intron ablated circRNA formation while the minimal deletion in the right intron gave circRNA and GFP levels equal to no deletion. Therefore, for the right intron a certain minimal distance is required (FIGS. 11A-11F).

We also tested whether the sequence in the right intron was important; i.e., whether the minimal construct worked because of the increased distance or because of the actual sequences contained. Therefore, we created another deletion in the right intron which preserved the same distance between Alu and splice site as the minimal deletion but contained different sequence (from a different portion of the intron). This construct behaved identically to the original right minimal deletion, with GFP and circRNA levels equal to the no deletion construct (FIGS. 13A-13D). Since the left deletion and minimal right deletion were both tolerated, we decided to rationally combine these two deletions to make a double deletion construct. IMPORTANTLY, this double deletion construct was better than either single deletion, with about 5-6 times greater circRNA and GFP expression than the original construct (FIGS. 12A-12F). These findings provide the foundation for designing synthetic introns that can support circRNA formation.

With the double deletion construct we were able to delete a total of 723 nucleotides from the HIPK3 introns, broken into 226 nt in the left intron and 497 nt in the right intron. Based on these results, we hypothesized that we could make similar deletions in other introns used for circRNA formation. Theoretical designs of synthetic introns with deletions in the EPHB4, ZKSCAN1, and Laccase2 intron pairs (FIGS. 14A-14D) are shown. It is also important to note that these synthetic introns provide more space for incorporation of other genomic elements within the AAV vector.

In summary, these foundational studies demonstrate that small, synthetic backsplicing introns can be generated to efficiently generate circRNA. Further, different permutation combinations of synthetic intronic elements with insertions or deletions can be generated to achieve multiplexed expression of different genomic elements using AAV vectors.

The foregoing is illustrative of the present invention and is not to be construed as limiting thereof. The invention is defined by the following claims, with equivalents of the claims to be included therein.

```
REPRESENTATIVE INTRONIC ELEMENTS
Sequence 1: ZKSCAN1
Left
                                                          (SEQ ID NO: 13)
agtgacagtggagattgtacagttttttcctcgatttgtcaggattttttttttttgacggagtttaacttcttgtctcccagg taggaagtgcagtggcgtaatctcggctcactacaacctccacctcctgggttcaagcgtttctcctgcctcagctttccgagta gctgggattacaggcgcctgccaccatgccctgctgacttttgtattttagtagagacggggtttcaccatgttggccaggctg gtcttgaactcctgaccgcaggcgattggcctgcctcggcctcccaaagtgctgagattacaggcgtgagccaccaccccggcc tcaggagcgttctgatagtgcctcgatgtgctgcctcctataaagtgttagcagcacagatcacttttttgtaaaggtacgtacta atgacttttttttttatacttcag Right
                                                          (SEQ ID NO: 14)
gtaagaagcaaggtttcatttaggggaagggaaatgattcaggacgagagtctttgtgctgctgagtgcctgtgatgaagaagca tgttagtcctgggcaacgtagcgagacccatctctacaaaaaatagaaaaattagccaggtatagtggcgcacacctgtgattc cagctacgcaggaggctgaggtggggaggattgcttgagcccaggaggttgaggctgcagtgagctgtaatcatgccactactcca acctgggcaacacagcaaggaccctgtctcaaaagctacttacagaaaagaattaggctcggcacggtagctcacacctgtaatc ccagcactttgggaggctgaggcgggcagatcacttgaggtcaggagtttgagaccagcctggccaacatggtgaaaccttgtct ctactaaaaatatgaaaattagccaggcatggtggcacattcctgtaatcccagctactcgggaggctgaggcaggagaatcact tgaacccaggaggtggaggttgcagtaagccgagatcgtaccactgtgctctagccttggtgacagagcgagactgtcttaaaaa aaaaaaaaaaaaaaagaattaattaaaaatttaaaaaaaaatgaaaaaaagctgcatgcttgtttttttgttttttagttattct
```

-continued acattgttgtcattattaccaaatattggggaaaatacaacttacagaccaatctcaggagttaaatgttactacgaaggcaaat gaactatgcgtaatgaacctggtaggcatta Sequence 2: HIPK3
Left (SEQ ID NO: 15)

gcctcagcctctcaaagtgctaggattacagggatctatacttttcttttgagggaaaatgttggcaccgtttctagggcatatt ggccatttcagcttctcagtaaatatttgttaagtaattaaatgcacttgattctttattcttagccttttaacgcaatactcag aatagctgaagcaccaattaactgaaatggagatattataaagatagttatcttctccaagggaaaaaatcatcttcatggaaat taattactttttttacaaattgtgaatttgacccttaagagttttcttcctgatatttaaaattgaaaaaaaaattgttgacatta atatttcttctttcctttttttctttccttttttttttttttttttgcag Right (SEQ ID NO: 16)

gtaggtaacaactccatacttttttggttgtttattaatgtgaaatttctgctaaatgaaatacttttgtgtgtgtttgtggtaga agagaccacttcagttaaataaggaaatcaagagaggatcaatttaggttcgttttaaagagattaaaaaaaatcaagacataaa atctacccaagcaggatagaaatctccactgcaaagttccatgccaaagacatctggttattttattttttaatggaagacttga aggaatgataggtgattaataatgatcaaacagaagtctttaaatgttggaaagtatttacattaatctttgtatatatcattgg gcattttagcacttgagagaaatagttattaaagatataatcaatcatatgtaactgaacatttagaaaaattatatacaggtt tgagtagcccttatctgaaacttttggggccagaagtgttttggattccagattttccggattttggaatatttgcactgccaa ctagttaagcaccccccaaatttgaaaattcgtttcctttgagtgtcatgtcaatgcccaaaaagtttcagatatttggatttgag atgctcaacctgtataaggattcagaaagttattctgattaatgattttaagattcagatatacaataatcccagcaacttggga ggctgaggcaggagaatcacttgaacccaggagatggaggttgcagtgagccgagatcatgccattgcactcca SEQUENCES OF SYNTHETIC INTRONS WITH DELETIONS
>HIPK3 delta L (SEQ ID NO: 17)

gcctcagcctctcaaagtgctaggattacagggatctatactacaaattgtgaatttgacccttaagagttttcttcctgatatt taaaattgaaaaaaaaattgttgacattaatatttcttctttcctttttttctttccttttttttttttttttttgcag >HIPK3 delta R (SEQ ID NO: 18)

gtaggtaacccaactagttaagcaccccccaaatttgaaaattcgtttcctttgagtgtcatgtcaatgcccaaaaagtttcagat atttggatttgagatgctcaacctgtataaggattcagaaagttattctgattaatgattttaagattcagatatacaataatcc cagcaacttgggaggctgaggcaggagaatcacttgaacccaggagatggaggttgcagtgagccgagatcatgccattgcactc ca >ZKSCAN1 delta L (SEQ ID NO: 19)

agtgacagtggagattgtacagttttttcctcgatttgtcaggatttttttttttttgacggagtttaacttcttgtctcccagg taggaagtgcagtggcgtaatctcggctcactacaacctccacctcctgggttcaagcgtttctcctgcctcagctttccgagta gctgggattacaggcgcctgccaccatgcccgctgacttttgtattttagtagagacggggtttcaccatgttggccaggctg gtcttgaactcctgaccgcaggcgattggcctgcctcggcctcccaaagtgctgagattacaggcgtgagccaccaccccggcc tcaggagcgttctgatagtgcctcgaacagatcacttttgtaaaggtacgtactaatgactttttttttatacttcag >ZKSCAN1 delta R (SEQ ID NO: 20)

gtaagaagcaggaggctgaggtggggaggattgcttgagcccaggaggttgaggctgcagtgagctgtaatcatgccactactcca acctgggcaacacagcaaggaccctgtctcaaaagctacttacagaaaagaattaggctcggcacggtagctcacacctgtaatc ccagcactttgggaggctgaggcgggcagatcacttgaggtcaggagtttgagaccagcctggccaacatggtgaaaccttgtct ctactaaaaatatgaaaattagccaggcatggtggcacattcctgtaatcccagctactcgggaggctgaggcaggagaatcact tgaacccaggaggtggaggttgcagtaagccgagatcgtaccactgtgctctagccttggtgacagagcgagactgtcttaaaaa aaaaaaaaaaaaaaagaattaattaaaaatttaaaaaaaaaatgaaaaaaagctgcatgcttgtttttttgttttttagttattct -continued acattgttgtcattattaccaaatattggggaaaatacaacttacagaccaatctcaggagttaaatgttactacgaaggcaaat
gaactatgcgtaatgaacctggtaggcatta >Laccase2 delta L (SEQ ID NO: 21)
tcattgagaaatgactgagttccggtgctctcaagtcattgatctttgtcgacttttatttggtctctgtaataacgacttcaaa
aacattaaattctgttgcgaagccagtaagctacaaaaagaaaaaacaagagagaatgctatagtcgtatagtatagtttcccga
ctatctgatacccattacttatctaggggggaatgcgaacccaaaattttatcagttttctcggatatcgatagatattggggaat
aaatttaaataaataaattttgggcgggtttagggcgtggcaaaaagttttttggcaaatcgctagaaatttacaagacttataa
aattatgaaaaaatacaacaaaattttaaacacgtgggcgtgacagttttggacggttttagtataataataagctaaatcgaga
ctaagttttattgttatatatattttttttattttatgcag >Laccase2 delta R (SEQ ID NO: 22)
gtaagtattcaaaagcatttccgaccatgtaaagtatatatattcttaataaggatcaatagccgagtcgatctcgccatgtccg
tctgtcttattattttattaccgccgagacatcaggaactataaaagctagaaggatgagttttagcatacagattctagagaca
aggacgcagagcaagtttgttgatccatgctgccacgctttaactttctcaaattgcccaaaactgccatgcccacattttgaa
ctattttcgaaattttttcataattgtattactcgtgtaaatttccatcaatttgccaaaaaacttttttgtcacgcgttaacgcc
ctaaagccgccaatttggtcacgcccacactattgaacaattatcaaatttttttctcattttattccccaatatctatcgatatc
cccgattatgaaattattaaatttcgcgttcgcattcacactagctgagtaacgagtatctgatagttggggaaatcgacttatt
ttttatatacaatgaaaatgaatttaatcatatgaatatcgattatagcttttattttaatatgaatatttatttgggcttaagg
tgtaaccctcctcgacataagactcacatggcgcaggcacattgaagacaaaaatactcattgtcgggtctcgcaccctccagcag
cacctaaaattatgtcttcaattattgccaacattggagacacaattagtctgtggcacctcag >EPHB4 delta L (SEQ ID NO: 23)
ccagctactcaggaggctgaggcagaagaatcattttaacccgggaggcggagattgcagtgagccaagatcgcgccactgcgct
ccaggcctgggtgacaccacggagttaattcccagctgacggggccctgcctgatttctcag >EPHB4 delta R (SEQ ID NO: 24)
gtgagcaccgttcccacttacacccagaggccacttgggttaagaagccaggacagacagtgggtcccaggtcacctcctccagc
cttttcctcttgggctaagccctggtcctctgccttttcttttttttaagacagagcctcgctctgtcgcccaggctggagtgca
gtggcgcgatctcggctcattgctgtctccacctccagggttcaagcgattctcctgcctcagtctcccaagtagctggtactat
aggcatgcaccaccatgctgactaattttgtattttagtagacacaggtttcaccatgtaggccaggctggtatcaaactcc
tgacctcaagtgatctccccacctcagcctcccaaagtgctggtattacaggtgtgaggcaccacgcctggccagccctctgcct
ttaatttcctctgggaaaggctgggctcctgggaccttcctttcccactgccccatacagctgaaggttgtc REPRESENTATIVE IRES ELEMENTS
Sequence 1: Encephalomyocarditis virus IRES (SEQ ID NO: 25)
gatccgcccctctcctcccccccccctaacgttactggccgaagccgcttggaataaggccggtgtgcgtttgtctatatgtta
ttttccaccatattgccgtcttttggcaatgtgagggcccggaaacctggccctgtcttcttgacgagcattcctaggggtcttt
cccctctcgccaaaggaatgcaaggtctgttgaalgtcgtgaaggaagcagttcctctggaagcttcttgaagacaaacaacgtc
tgtagcgaccctttgcaggcagcggaaccccccacctggcgacaggtgcctctgcggccaaaagccacgtgtataagatacacct
gcaaaggcggcacaaccccagtgccacgttgtgagttggatagttgtggaaagagtcaaatggctctcctcaagcgtattcaaca
aggggctgaaggatgcccagaaggtacccccattgtatgggatctgatctggggcctcggtacacatgctttacatgtgtttagtc
gaggttaaaaaaacgtctaggccccccgaaccacggggacgtggttttcctttgaaaaacacgatgataatatggccaca
Sequence 2: Poliovirus IRES (SEQ ID NO: 26)
ttaaaacagctctggggttgttcccacccagagggcccacgtggcggccagtacactggtattgcggtacctttgtacgcctgtt
ttatactcccttcccccgtaacttagaagcacaatgtccaagttcaataggaggggggtacaaaccagtaccaccacgaacaagca -continued

```
cttctgttccccggtgaggctgtataggctgtttccacggctaaaagcggctgatccgttatccgctcatgtacttcgagaagc ctagtatcaccttggaatcttcgatgcgttgcgctcaacactcaaccccagagtgtagcttaggtcgatgagtctggacgttcct caccggcgacggtggtccaggctgcgttggcggcctacctgtggcccaaagccacaggacgctagttgtgaacaaggtgtgaaga gcctattgagctacctgagagtcctccggcccctgaatgcggctaatcctaaccacggagcaggcagtggcaatccagcgaccag cctgtcgtaacgcgcaagttcgtggcggaaccgactactttgggtgtccgtgtttccttttattttttacaatggctgcttatggt gacaatcattgattgttatcataaagcaaattggattggccatccggtgagaatttgattattaaattactctcttgttgggatt gctcctttgaaatcttgtgcactcacacctattggaattacctcattgttaagatat
```

REPRESENTATIVE PROMOTER ELEMENTS
CMV promoter
(SEQ ID NO: 27)

```
atagtaatcaattacggggtcattagttcatagcccatatatggagttccgcgttacataacttacggtaaatggcccgcctggc tgaccgcccaacgacccccgcccattgacgtcaataatgacgtatgttcccatagtaacgccaatagggactttccattgacgtc aatgggtggagtatttacggtaaactgcccacttggcagtacatcaagtgtatcatatgccaagtacgccccctattgacgtcaa tgacggtaaatggcccgcctggcattatgcccagtacatgaccttatgggactttcctacttggcagtacatctacgtattagtc atcgctattaccatggtgatgcggttttggcagtacatcaatgggcgtggatagcggtttgactcacggggatttccaagtctcc accccattgacgtcaatgggagtttgttttggcaccaaaatcaacgggactttccaaaatgtcgtaacaactccgccccattgac gcaaatgggcggtaggcgtgtacggtgggaggtctatataagcagagctggtttagtgaaccgtcagatc
```

REPRESENTATIVE POLY-A SEQUENCE ELEMENTS
SV40 poly-A
(SEQ ID NO: 28)

```
tgatcataatcagccataccacatttgtagaggttttacttgctttaaaaaacctcccacacctcccctgaacctgaaacataa aatgaatgcaattgttgttgttaacttgtttattgcagcttataatggttacaaataaagcaatagcatcacaaatttcacaaat aaagcatttttttcactgcattctagttgtggtttgtccaaactcatcaatgtatctta
```

The foregoing is illustrative of the present invention and is not to be construed as limiting thereof. The invention is defined by the following claims, with equivalents of the claims to be included therein.

TABLE 1

| Exemplary AAV sequences | | | | | |
|---|---|---|---|---|---|
| | GenBank Accession Number | | GenBank Accession Number | | GenBank Accession Number |
| Complete Genomes | | Hu S17 | AY695376 | Hu66 | AY530626 |
| Adeno-associated virus 1 | NC_002077, AF063497 | Hu T88 | AY695375 | Hu42 | AY530605 |
| Adeno-associated virus 2 | NC 001401 | Hu T71 | AY695374 | Hu67 | AY530627 |
| Adeno-associated virus 3 | NC 001729 | Hu T70 | AY695373 | Hu40 | AY530603 |
| Adeno-associated virus 3B | NC 001863 | Hu T40 | AY695372 | Hu41 | AY530604 |
| Adeno-associated virus 4 | NC 001829 | Hu T32 | AY695371 | Hu37 | AY530600 |
| Adeno-associated virus 5 | Y18065, AF085716 | Hu T17 | AY695370 | Rh40 | AY530559 |
| Adeno-associated virus 6 | NC 001862 | Hu LG15 | AY695377 | Rh2 | AY243007 |
| Avian AAV ATCC VR-865 | AY186198, AY629583, NC_004828 | Clade C | | Bb1 | AY243023 |
| Avian AAV strain DA-1 | NC_006263, AY629583 | Hu9 | AY530629 | Bb2 | AY243022 |
| Bovine AAV | NC_005889, AY388617, AAR26465 | Hu11 | AY530576 | | |

TABLE 1-continued

Exemplary AAV sequences

| | GenBank Accession Number | | GenBank Accession Number | | GenBank Accession Number |
|---|---|---|---|---|---|
| AAV11 | AAT46339, AY631966 | Hu11 | AY530577 | Rh10 | AY243015 |
| AAV12 | AB116639, DQ813647 | | | Hu17 | AY530582 |
| Clade A | | Hu53 | AY530615 | Hu6 | AY530621 |
| AAV1 | NC_002077, AF063497 | Hu55 | AY530617 | Rh25 | AY530557 |
| AAV6 | NC 001862 | Hu54 | AY530616 | Pi2 | AY530554 |
| Hu48 | AY530611 | Hu7 | AY530628 | Pi1 | AY530553 |
| Hu43 | AY530606 | Hu18 | AY530583 | Pi3 | AY530555 |
| Hu44 | AY530607 | Hu15 | AY530580 | Rh57 | AY530569 |
| Flu46 | AY530609 | Hu16 | AY530581 | Rh50 | AY530563 |
| Clade B | | Hu25 | AY530591 | Rh49 | AY530562 |
| Hu19 | AY530584 | Hu60 | AY530622 | Hu39 | AY530601 |
| Hu20 | AY530586 | Ch5 | AY243021 | Rh58 | AY530570 |
| Hu23 | AY530589 | Hu3 | AY530595 | Rh61 | AY530572 |
| Hu22 | AY530588 | Hu1 | AY530575 | Rh52 | AY530565 |
| Hu24 | AY530590 | Hu4 | AY530602 | Rh53 | AY530566 |
| Hu21 | AY530587 | Hu2 | AY530585 | Rh51 | AY530564 |
| Hu27 | AY530592 | Hu61 | AY530623 | Rh64 | AY530574 |
| Hu28 | AY530593 | Clade D | | Rh43 | AY530560 |
| Hu 29 | AY530594 | Rh62 | AY530573 | AAV8 | AF513852 |
| Hu63 | AY530624 | Rh48 | AY530561 | Rh8 | AY242997 |
| Hu64 | AY530625 | Rh54 | AY530567 | Rh1 | AY530556 |
| Hu13 | AY530578 | Rh55 | AY530568 | Clade F | |
| Hu56 | AY530618 | Cy2 | AY243020 | Hu14 (AAV9) | AY530579 |
| Hu57 | AY530619 | AAV7 | AF513851 | Hu31 | AY530596 |
| Hu49 | AY530612 | Rh35 | AY243000 | Hu32 | AY530597 |
| Hu58 | AY530620 | Rh37 | AY242998 | Clonal Isolate | |
| Hu34 | AY530598 | Rh36 | AY242999 | AAV5 | Y18065, AF085716 |
| Hu35 | AY530599 | Cy6 | AY243016 | AAV 3 | NC_001729 |
| AAV2 | NC_001401 | Cy4 | AY243018 | AAV 3B | NC 001863 |
| Hu45 | AY530608 | Cy3 | AY243019 | AAV4 | NC_001829 |
| Hu47 | AY530610 | Cy5 | AY243017 | Rh34 | AY243001 |
| Hu51 | AY530613 | Rh13 | AY243013 | Rh33 | AY243002 |
| Hu52 | AY530614 | Clade E | | Rh32 | AY243003 |
| HuT41 | AY695378 | Rh38 | AY530558 | | |

TABLE 2

Naturally occurring, levorotatory (L-) amino acids

| | Abbreviation | |
|---|---|---|
| Amino Acid Residue | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 3

Modified amino acid residues for use herein

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |

TABLE 3-continued

Modified amino acid residues for use herein

| Modified Amino Acid Residue | Abbreviation |
| --- | --- |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,21-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methyl isoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

TABLE 4

Representative example of amino acid residues corresponding to S257 in AAV4

| Serotype | Position 1 | Position 2 |
| --- | --- | --- |
| AAV1 | A263X | T265X |
| AAV2 | Q263X | -265X |
| AAV3a | Q263X | -265X |
| AAV3b | Q263X | -265X |
| AAV4 | S257X | -259X |
| AAV5 | G253X | V255X |
| AAV6 | A263X | T265X |
| AAV7 | E264X | A266X |
| AAV8 | G264X | S266X |
| AAV9 | S263X | S265X |

Where, (X) → mutation to any amino acid
(-) → insertion of any amino acid
Note:
Position 2 inserts are indicated by the site of insertion

TABLE 5

Exemplary viral IRESs

| IRES name | virus name | IRES found in | IRES size [nt] |
| --- | --- | --- | --- |
| ABPV_IGRpred | ABPV | Acute bee paralysis virus | 199 |
| AEV | AEV | Avian encephalomyelitis virus | 494 |
| ALPV_IGRpred | ALPV | Aphid lethal paralysis virus | 184 |
| BQCV_IGRpred | BQCV | Black queen cell virus | 190 |
| BVDV1_1-385 | BVDV1 | Bovine viral diarrhea virus 1 | 385 |
| BVDV1_29-391 | | | 363 |
| CrPV_5NCR | CrPV | Cricket paralysis virus | 708 |
| CrPV_IGR | | | 192 |
| crTMV_IREScp | crTMV | Crucifer *tobamovirus* | 146 |
| crTMV_IRESmp75 | | | 75 |
| crTMV_IRESmp228 | | | 228 |
| crTMV_IREScp | crTMV | Crucifer *tobamovirus* | 148 |
| crTMV_IREScp | crTMV | Crucifer *tobamovirus* | 148 |
| CSFV | CSFV | Classical swine fever virus | 373 |
| CVB3 | CVB3 | Human coxsackievirus B3 | 750 |
| DCV_IGR | DCV | *Drosophila* C virus | 189 |
| EMCV-R | EMCV-R | Encephalomyocarditis virus | 576 |
| EoPV_5NTR | EoPV | *Ectropis obliqua* picorna-like virus | 390 |
| ERAV_245-961 | ERAV | Equine rhinitis A virus 1 | 712 |
| ERBV_162-920 | ERBV | Equine rhinitis B virus | 759 |
| EV71_1-748 | EV71 | Human enterovirus 71 | 748 |
| FeLV-Notch2 | FeLV-Notch2 | *Felis silvestris* | 238 |
| FMDV_type_C | FMDV | Foot-and-mouth disease virus | 461 |

TABLE 5-continued

Exemplary viral IRESs

| IRES name | virus name | IRES found in | IRES size [nt] |
|---|---|---|---|
| GBV-A | GBV-A | Hepatitis GB virus A | 693 |
| GBV-B | GBV-B | Hepatitis GB virus B | 416 |
| GBV-C | GBV-C | Hepatitis GB virus C | 630 |
| gypsy_env | Gypsy | Drosophila melanogaster | 330 |
| gypsyD5 | | | 261 |
| gypsyD2 | | | 517 |
| HAV_BM175 | HAV | Human hepatitis A virus | 584 |
| HCV_type_1a | HCV_type_1a | Hepatitis C virus | 383 |
| HiPV_IGRpred | HiPV | Himetobi P virus | 188 |
| HIV-1 | HIV-1 | Human Immunodeficiency Virus type 1 | 233 |
| HoCV1_IGRpred | HoCV-1 | Homalodiscacoagulata virus-1 | 188 |
| BRV-2 | IIRV2 | Human rhinovirus 2 | 604 |
| IAPV_IGRpred | IAPV | Israel acute paralysis virus of bees | 199 |
| idefix | Idefix | Drosophila melanogaster | 521 |
| KBV_IGRpred | KBV | Kashmir bee virus | 202 |
| LINE-1_ORF1_-101_to_-1 | LINE-1 | Mus musculus | 101 |
| LINE-1_ORF1_-302_to_-202 | | | 101 |
| LINE-1_ORF2_-138 to_-86 | | | 53 |
| LINE-1_ORF1_-44_to_-1 | | | 47 |
| PSIV_IGR | PSIV | Plautia stali intestine virus | 145 |
| PV_type1_Mahoney | PV | Human poliovirus 1 | 312 |
| PV_type3_Leon | PV | Human poliovirus 1 | 742 |
| REV-A | REV-A | Reticuloendotheliosis virus | 577 |
| RhPV_5NCR | RhPV | Rhopalosiphum padi virus | 579 |
| RhPV_IGR | RhPV | | 232 |
| SINV1_IGRpred | SINV-1 | Solenopsis invicta virus 1 | 200 |
| SV40_661-830 | SV40 | Simian virus 40 | 170 |
| TMEV | TMEV | Theiler's encephalomyelitis virus | 1040 |
| TMV_UI_IRESmp228 | TMV_type1 | Tobacco mosaic virus | 231 |
| TRV_5NTR | TrV | Triatoma virus | 694 |
| TrV_IGR | | | 221 |
| TSV_IGR | TSV | Taura syndrome virus | 250 |

TABLE 6

Exemplary cellular IRESs

| IRES name | Source name | IRES size [nt] |
|---|---|---|
| AML1/RUNX1 | AML1/RUNX1 | 1561 |
| Antp-D | Antp | 252 |
| Antp-DE | | 408 |
| Antp-CDE | | 1730 |
| Apaf-1 | Apaf-1 | 583 |
| Apaf-1 | Apaf-1 | 231 |
| AQP4 | AQP4 | 284 |
| AT1R_var1 | hAT1R-B | 356 |
| AT1R_var2 | hAT1R-A | 272 |
| AT1R_var3 | hAT1R-C | 330 |
| AT1R_var4 | hAT1R-D | 414 |
| BAG1_p36delta236nt | BAG-1 | 130 |
| BAG1_p36 | | 366 |
| BCL2 | BCL2 | 1137 |
| BiP_-222_-3 | BiP | 222 |
| c-IAP1_285-1399 | c-IAP1 | 1115 |
| c-IAP1_1313-1462 | | 150 |
| c-jun | c-jun | 301 |
| c-myc | c-myc | 393 |
| Cat-1_224 | Cat-1 | 224 |
| CCND1 | CCND1 | 209 |
| DAPS | DAPS | 305 |
| eIF4G | eIF4G | 357 |
| eIF4GI-ext | eIF4GI | 196 |
| eIF4GII | eIF4GII | 256 |
| eIF4GII-long | eIF4GII | 327 |
| ELG1 | ELG1 | 460 |
| ELH | ELH | 319 |
| FGF1A | FGF1 | 434 |
| FMR1 | FMR1 | 252 |
| Gtx-133-141 | GM | 9 |
| Gtx-1-166 | | 166 |
| Gtx-1-120 | | 120 |
| Gtx-1-196 | | 196 |
| hairless | Hairless | 435 |
| HAP4 | HAP4 | 270 |
| HIF1a | Hif1a | 257 |
| hSNM1 | hSNM1 | 918 |
| Hsp101 | Hsp101 | 161 |
| hsp70 | Hsp70Aa | 503 |
| hsp70 | HSPA1A | 193 |
| Hsp90 | Hsp83 | 149 |

TABLE 6-continued

Exemplary cellular IRESs

| IRES name | Source name | IRES size [nt] |
|---|---|---|
| IGF2 Jeader2 | IGF2 | 121 |
| Kv1.4_1.2 | Kcna4 | 1197 |
| L-myc | L-myc | 52 |
| LamB1_-335_-1 | LamB1 | 335 |
| LEF1 | LEF1 | 1167 |
| MNT_75-267 | MNT | 193 |
| MNT_36-160 | | 125 |
| MTG8a | MTG8a | 199 |
| MYB | c-myb | 150 |
| MYT2_997-1152 | MYT2 | 156 |
| n-MYC | n-MYC | 320 |
| NDST1 | NDST1 | 420 |
| NDST2 | NDST2 | 750 |
| NDST3 | NDST3 | 247 |
| NDST4L | NDST4L | 672 |
| NDST4S | NDST4S | 418 |
| NRF_-653_-17 | NRF | 637 |
| NtHSF1 | NtHSF1 | 453 |
| ODC1 | ODC1 | 303 |
| p27kip1 | p27kip1 | 152 |

TABLE 6-continued

Exemplary cellular IRESs

| IRES name | Source name | IRES size [nt] |
|---|---|---|
| p53_128-269 | p53/p47 | 142 |
| PDGF2/c-sis | PDGF2/c-sis | 1022 |
| Pim-1 | PIM1 | 396 |
| PITSLRE_p58 | PITSLRE | 381 |
| Rbm3 | Rbm3 | 22 |
| reaper | Rpr | 168 |
| Scamper | Scamper | 365 |
| TFIID | TBP1 | 188 |
| TIF4631 | TIF4631 | 348 |
| Ubx_1-966 | Ubx | 966 |
| Ubx_373-961 | | 589 |
| UNR | UNR | 429 |
| Ure2 | Ure2 | 167 |
| UtrA | Utrn | 506 |
| VEGF-A_-133_-1 | VEGF-A | 133 |
| XIAP_5-464 | XIAP | 460 |
| XIAP_305-466 | | 162 |
| YAP1 | YAP1 | 164 |

That which is claimed is:

1. An adeno-associated virus (AAV) genome encoding a circular RNA, wherein the AAV genome comprises, from 5' to 3':
   (a) a first inverted terminal repeat;
   (b) a first intronic element;
   (c) a nucleotide sequence of interest;
   (d) a second intronic element;
   (e) a second inverted terminal repeat;
   wherein (c) is directly coupled to (b) and (d), respectively; and
   wherein the first intronic element and the second intronic element are at least one pair selected from the group consisting of:
   the first intronic element consists of SEQ ID NO:13 and the second intronic element comprises SEQ ID NO:14;
   the first intronic element consists of SEQ ID NO:15 and the second intronic element comprises SEQ ID NO:16;
   the first intronic element consists of SEQ ID NO:15 and the second intronic the first intronic element consists of SEQ ID NO:15 and the second intronic element comprises SEQ ID NO:18;
   the first intronic element consists of SEQ ID NO:17 and the second intronic element comprises SEQ ID NO:18;
   the first intronic element consists of SEQ ID NO:17 and the second intronic the first intronic element consists of SEQ ID NO:17 and the second intronic element comprises SEQ ID NO:16;
   the first intronic element consists of SEQ ID NO:19 and the second intronic element comprises SEQ ID NO:20;
   the first intronic element consists of SEQ ID NO:21 and the second intronic element comprises SEQ ID NO:22;
   the first intronic element consists of SEQ ID NO:23 and the second intronic element comprises SEQ ID NO:24;
   the first intronic element consists of SEQ ID NO:29 and the second intronic element comprises SEQ ID NO:30; and
   the first intronic element consists of SEQ ID NO:31 and the second intronic element comprises SEQ ID NO:32.

2. The AAV genome of claim 1, wherein the first intronic element and the second intronic element are capable of generating a covalently closed circular RNA.

3. The AAV genome of claim 2, wherein the first intronic element and the second intronic element are capable of facilitating formation of a covalently closed circular RNA following transcription of the AAV genome in a mammalian cell.

4. The AAV genome of claim 1, wherein the nucleotide sequence of interest encodes a non-coding RNA.

5. The AAV genome of claim 1, wherein the nucleotide sequence of interest encodes a translatable mRNA.

6. The AAV genome of claim 5, wherein the translatable mRNA encodes a therapeutic protein.

7. The AAV genome of claim 5, comprising an internal ribosome entry site (IRES) capable of driving translation of the translatable mRNA.

8. The AAV genome of claim 7, wherein the IRES is a viral IRES or a cellular IRES.

9. The AAV genome of claim 7, wherein the IRES is from Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, *Homalodisca coagulata* virus-1, Human Immunodeficiency Virus type 1, *Homalodisca coagulata* virus-1, Himetobi P virus, Hepatitis C virus, Hepatitis A virus, Hepatitis GB virus, Foot and mouth disease virus, Human enterovirus 71, Equine rhinitis virus, *Ectropis obliqua* picorna-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPA1, Human AML1/RUNX1, *Drosophila* antennapedia, Human AQP4, Human AT1R, Human BAG-1, Human BCL2, Human BiP, Human c-IAP1, Human c-myc, Human eIF4G, Mouse NDST4L, Human LEF1, Mouse HIF1 alpha, Human n-myc, Mouse Gtx, Human p27kip1, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAP1, WO0155369, tobacco etch virus, or turnip crinkle virus.

10. The AAV genome of claim 7, comprising at least two IRESs.

11. The AAV genome of claim 1, wherein the nucleotide sequence of interest encodes a RNA that is capable of directing alternative splicing in a cell.

12. The AAV genome of claim 1, wherein the nucleotide sequence of interest encodes a RNA silencing molecule, a guide RNA molecule that can target a genomic element, a guide RNA molecule that can target an RNA transcript, a tRNA molecule, a long noncoding RNA molecule, an antisense RNA molecule, or any combination thereof.

13. The AAV genome of claim 1, wherein the first inverted terminal repeat and the second inverted terminal repeat are AAV terminal repeats and are derived from any one of AAV serotypes 1, 2, 3, 4, 5, 6, 7, 8, 9, 10, and 11.

14. The AAV genome of claim 13, wherein the first inverted terminal repeat and the second inverted terminal repeat are derived from AAV serotype 2.

15. The AAV genome of claim 14, wherein the first inverted terminal repeat and/or the second inverted terminal repeat sequences comprise one or more insertions, deletions, truncations, and/or missense mutations.

16. The AAV genome of claim 1, comprising a promoter located between the first inverted terminal repeat and the first intronic element.

17. The AAV genome of claim 16, wherein the promoter is a RNA polymerase promoter.

18. The AAV genome of claim 1, comprising a 5' UTR located 3' to the first inverted terminal repeat.

19. The AAV genome of claim 1, comprising a 3' UTR located 5' to the second inverted terminal repeat.

20. The AAV genome of claim 19, comprising a translation regulating region located in the 3' UTR.

21. The AAV genome of claim 20, wherein the translation regulating region comprises a polyadenylation sequence and/or a structural element that stabilizes the circRNA.

22. The AAV genome of claim 21, wherein the polyadenylation sequence is a SV40 polyadenylation sequence.

23. An adeno-associated virus (AAV) capsid or particle comprising the AAV genome of claim 1.

24. The AAV capsid or particle of claim 23, which is of any one of AAV serotypes 1, 2, 3, 4, 5, 6, 7, 8, 9, 10, and 11.

25. The AAV capsid or particle of claim 23, which comprises one or more insertions, deletions and/or substitutions in the capsid or particle sequence relative to a wildtype AAV.

26. A method of expressing a covalently closed circRNA in a mammalian cell, comprising contacting the cell with the AAV capsid or particle of claim 23.

27. The method of claim 26, wherein the first intronic element and the second intronic element facilitate formation of a covalently closed circular RNA following transcription of the AAV genome in the cell.

28. The method of claim 26, wherein the nucleotide sequence of interest is expressed in the cell.

* * * * *

UNITED STATES PATENT AND TRADEMARK OFFICE
CERTIFICATE OF CORRECTION

PATENT NO. : 11,718,862 B2
APPLICATION NO. : 17/506089
DATED : August 8, 2023
INVENTOR(S) : Asokan et al.

Page 1 of 1

It is certified that error appears in the above-identified patent and that said Letters Patent is hereby corrected as shown below:

In the Specification

Column 8, Line 19: Please correct "(3-islet cells" to read --β-islet cells--

Column 49, Line 65, Table 1 (in the row with Bovine AAV, Column 3): Please correct "Hu11" to read --Hu10--

Column 55, Line 13, Table 5: Please correct "HAV-BM175" to read --HAV-HM175--

Column 56, Line 49, Table 6: Please correct "DAPS DAPS" to read --DAP5 DAP5--

Column 56, Line 57, Table 6: Please correct "GM" to read --Gtx--

Column 57, Line 6, Table 6: Please correct "IGF2 Jeader2" to read --IGF2_leader2--

In the Claims

Column 75, Lines 37-39, Claim 1: Please correct "the first intronic element consists of SEQ ID NO:15 and the second intronic the first intronic element consists of SEQ ID NO:15 and the second intronic element comprises SEQ ID NO:18;" to read --the first intronic element consists of SEQ ID NO:15 and the second intronic element comprises SEQ ID NO:18;--

Column 75, Lines 44-46, Claim 1: Please correct "the first intronic element consists of SEQ ID NO:17 and the second intronic the first intronic element consists of SEQ ID NO:17 and the second intronic element comprises SEQ ID NO:16;" to read --the first intronic element consists of SEQ ID NO:17 and the second intronic element comprises SEQ ID NO:16;--

Column 76, Line 51, Claim 9: Please correct "Human p27kip1" to read --Human p27kipl--

Signed and Sealed this
Twenty-fourth Day of October, 2023

Katherine Kelly Vidal
*Director of the United States Patent and Trademark Office*

SEQUENCE LISTING

```
<160> NUMBER OF SEQ ID NOS: 32

<210> SEQ ID NO 1
<211> LENGTH: 25
<212> TYPE: DNA
<213> ORGANISM: Artificial
<220> FEATURE:
<223> OTHER INFORMATION: primer

<400> SEQUENCE: 1
aacatgctac gcagagaggg agtgg                                    25

<210> SEQ ID NO 2
<211> LENGTH: 29
<212> TYPE: DNA
<213> ORGANISM: Artificial
<220> FEATURE:
<223> OTHER INFORMATION: primer

<400> SEQUENCE: 2
catgagacaa ggaaccccta gtgatggag                                29

<210> SEQ ID NO 3
<211> LENGTH: 44
<212> TYPE: DNA
<213> ORGANISM: Artificial
<220> FEATURE:
<223> OTHER INFORMATION: primer

<400> SEQUENCE: 3
gcatgctctt ctcaggagcg caccatcttc ttcaaggacg acgg               44

<210> SEQ ID NO 4
<211> LENGTH: 39
<212> TYPE: DNA
<213> ORGANISM: Artificial
<220> FEATURE:
<223> OTHER INFORMATION: primer

<400> SEQUENCE: 4
gcatgctctt cttacctgga cgtagccttc gggcatggc                     39
```

```
<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
caagtacgcc ccctattgac                                               20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
aagtcccgtt gattttggtg                                               20

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
ggacccaagg actacctcaa ggg                                           23

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
agggcacctc catctcggaa ac                                            22

<210> SEQ ID NO 9
<211> LENGTH: 32
<212> TYPE: DNA
<213> ORGANISM: Artificial
<220> FEATURE:
<223> OTHER INFORMATION: primer

<400> SEQUENCE: 9
ctgcttgtcg gccatgatat agacgttgtg gc                                 32

<210> SEQ ID NO 10
<211> LENGTH: 31
<212> TYPE: DNA
<213> ORGANISM: Artificial
<220> FEATURE:
<223> OTHER INFORMATION: primer

<400> SEQUENCE: 10
caagctgacc ctgaagttca tctgcaccac c                                  31

<210> SEQ ID NO 11
<211> LENGTH: 19
<212> TYPE: DNA
<213> ORGANISM: Artificial
<220> FEATURE:
<223> OTHER INFORMATION: primer
```

<400> SEQUENCE: 11
ccactcctcc acctttgac                                                19

<210> SEQ ID NO 12
<211> LENGTH: 17
<212> TYPE: DNA
<213> ORGANISM: Artificial
<220> FEATURE:
<223> OTHER INFORMATION: primer

<400> SEQUENCE: 12
accctgttgc tgtagcc                                                  17

<210> SEQ ID NO 13
<211> LENGTH: 448
<212> TYPE: DNA
<213> ORGANISM: Artificial
<220> FEATURE:
<223> OTHER INFORMATION: ZKSCAN1 left

<400> SEQUENCE: 13
agtgacagtg gagattgtac agttttttcc tcgatttgtc aggatttttt tttttttgac    60
ggagtttaac ttcttgtctc ccaggtagga agtgcagtgg cgtaatctcg ctcactaca    120
acctccacct cctgggttca agcgtttctc ctgcctcagc tttccgagta gctgggatta   180
caggcgcctg ccaccatgcc ctgctgactt ttgtattttt agtagagacg gggtttcacc   240
atgttggcca ggctggtctt gaactcctga ccgcaggcga ttggcctgcc tcggcctccc   300
aaagtgctga gattacaggc gtgagccacc accccggcc tcaggagcgt tctgatagtg    360
cctcgatgtg ctgcctccta aaagtgtta gcagcacaga tcacttttg taaaggtacg     420
tactaatgac tttttttta tacttcag                                      448

<210> SEQ ID NO 14
<211> LENGTH: 796
<212> TYPE: DNA
<213> ORGANISM: Artificial
<220> FEATURE:
<223> OTHER INFORMATION: ZKSCAN1 right

<400> SEQUENCE: 14
gtaagaagca aggtttcatt taggggaagg gaaatgattc aggacgagag tctttgtgct    60
gctgagtgcc tgtgatgaag aagcatgtta gtcctgggca acgtagcgag accccatctc   120
tacaaaaaat agaaaaatta gccaggtata gtggcgcaca cctgtgattc cagctacgca   180
ggaggctgag gtgggaggat tgcttgagcc caggaggttg aggctgcagt gagctgtaat   240
catgccacta ctccaacctg gcaacacag caaggaccct gtctcaaaag ctacttacag    300
aaaagaatta ggctcggcac ggtagctcac acctgtaatc ccagcacttt gggaggctga   360
ggcgggcaga tcacttgagg tcaggagttt gagaccagcc tggccaacat ggtgaaacct   420
tgtctctact aaaaatatga aaattagcca ggcatggtgg cacattcctg taatcccagc   480
tactcgggag gctgaggcag gagaatcact tgaacccagg aggtggaggt tgcagtaagc   540
cgagatcgta ccactgtgct ctagccttgg tgacagagcg agactgtctt aaaaaaaaa    600
aaaaaaaaaa aagaattaat taaaatttta aaaaaaatg aaaaaaagct gcatgcttgt    660
tttttgtttt tagttattct acattgttgt cattattacc aaatattggg gaaaatacaa    720
cttacagacc aatctcagga gttaaatgtt actacgaagg caaatgaact atgcgtaatg    780
aacctggtag gcatta 796

<210> SEQ ID NO 15
<211> LENGTH: 391
<212> TYPE: DNA
<213> ORGANISM: Artificial
<220> FEATURE:
<223> OTHER INFORMATION: HIPK3 left

<400> SEQUENCE: 15
gcctcagcct ctcaaagtgc taggattaca gggatctata cttttctttt gagggaaaat    60
gttggcaccg tttctagggc atattggcca tttcagcttc tcagtaaata tttgttaagt   120
aattaaatgc acttgattct ttattcttag cctttaacg caatactcag aatagctgaa   180
gcaccaatta actgaaatgg agatattata aagatagtta tcttctccaa gggaaaaaat   240
catcttcatg gaaattaatt actttttac aaattgtgaa tttgacccctt aagagttttc   300
ttcctgatat ttaaaattga aaaaaaaatt gttgacatta atatttcttc tttcctttt    360
tttctttcc tttttttttt tttttttgca g                                   391

<210> SEQ ID NO 16
<211> LENGTH: 754
<212> TYPE: DNA
<213> ORGANISM: Artificial
<220> FEATURE:
<223> OTHER INFORMATION: HIPK3 right

<400> SEQUENCE: 16
gtaggtaaca actccatact ttttggttgt ttattaatgt gaaatttctg ctaaatgaaa    60
tacttttgtg tgtgtttgtg gtagaagaga ccacttcagt taaataagga aatcaagaga   120
ggatcaattt aggttcgttt taagagatt aaaaaaaatc aagacataaa atctacccaa   180
gcaggataga aatctccact gcaaagttcc atgccaaaga catctggtta ttttattt    240
taatggaaga cttgaaggaa tgataggtga ttaataatga tcaaacagaa gtctttaaat   300
gttggaaagt atttacatta atctttgtat atatcattgg gcattttagc acttgagaga   360
aatagtttat taaagatata atcaatcata tgtaactgaa catttagaaa aattatatac   420
aggtttgagt agcccttatc tgaaactttt ggggccagaa gtgttttgga ttccagattt   480
ttccggatt tggaatattt gcactgccaa ctagttaagc accccaaat ttgaaaatc    540
gtttcctttg agtgtcatgt caatgcccaa aaagtttcag atatttggat ttgagatgct   600
caacctgtat aaggattcag aaagttattc tgattaatga ttttaagatt cagatataca   660
ataatcccag caacttggga ggctgaggca ggagaatcac ttgaacccag gagatggagg   720
ttgcagtgag ccgagatcat gccattgcac tcca                               754

<210> SEQ ID NO 17
<211> LENGTH: 165
<212> TYPE: DNA
<213> ORGANISM: Artificial
<220> FEATURE:
<223> OTHER INFORMATION: HIPK3 delta L

<400> SEQUENCE: 17
gcctcagcct ctcaaagtgc taggattaca gggatctata ctacaaattg tgaatttgac    60
ccttaagagt tttcttcctg atatttaaaa ttgaaaaaaa aattgttgac attaatattt   120
cttctttcct tttttttctt ttccttttt tttttttt tgcag                      165

<210> SEQ ID NO 18
<211> LENGTH: 257
<212> TYPE: DNA
<213> ORGANISM: Artificial
<220> FEATURE:
<223> OTHER INFORMATION: HIPK3 delta R

<400> SEQUENCE: 18

```
gtaggtaacc caactagtta agcaccccca aatttgaaaa ttcgtttcct ttgagtgtca      60
tgtcaatgcc caaaaagttt cagatatttg gatttgagat gctcaacctg tataaggatt     120
cagaaagtta ttctgattaa tgattttaag attcagatat acaataatcc cagcaacttg     180
ggaggctgag gcaggagaat cacttgaacc caggagatgg aggttgcagt gagccgagat     240
catgccattg cactcca                                                    257
```

<210> SEQ ID NO 19
<211> LENGTH: 419
<212> TYPE: DNA
<213> ORGANISM: Artificial
<220> FEATURE:
<223> OTHER INFORMATION: ZKSCAN1 delta L

<400> SEQUENCE: 19

```
agtgacagtg gagattgtac agttttttcc tcgatttgtc aggatttttt ttttttttgac    60
ggagtttaac ttcttgtctc ccaggtagga agtgcagtgg cgtaatctcg gctcactaca    120
acctccacct cctgggttca agcgtttctc ctgcctcagc tttccgagta gctgggatta    180
caggcgcctg ccaccatgcc ctgctgactt ttgtattttt agtagagacg ggtttcacc    240
atgttggcca ggctggtctt gaactcctga ccgcaggcga ttggcctgcc tcggcctccc    300
aaagtgctga gattacaggc gtgagccacc acccccggcc tcaggagcgt tctgatagtg    360
cctcgaacag atcacttttt gtaaaggtac gtactaatga cttttttttt atacttcag    419
```

<210> SEQ ID NO 20
<211> LENGTH: 626
<212> TYPE: DNA
<213> ORGANISM: Artificial
<220> FEATURE:
<223> OTHER INFORMATION: ZKSCAN1 delta R

<400> SEQUENCE: 20

```
gtaagaagca ggaggctgag gtgggaggat tgcttgagcc caggaggttg aggctgcagt     60
gagctgtaat catgccacta ctccaacctg gcaacacag caaggaccct gtctcaaaag    120
ctacttacag aaaagaatta ggctcggcac ggtagctcac acctgtaatc ccagcacttt    180
gggaggctga ggcgggcaga tcacttgagg tcaggagttt gagaccagcc tggccaacat    240
ggtgaaacct tgtctctact aaaaatatga aaattagcca ggcatggtgg cacattcctg    300
taatcccagc tactcgggag gctgaggcag gagaatcact tgaacccagg aggtggaggt    360
tgcagtaagc cgagatcgta ccactgtgct ctagccttgg tgacagagcg agactgtctt    420
aaaaaaaaaa aaaaaaaaa aagaattaat taaaaattta aaaaaaaatg aaaaaaagct    480
gcatgcttgt tttttgtttt tagttattct acattgttgt cattattacc aaatattggg    540
gaaaatacaa cttacagacc aatctcagga gttaaatgtt actacgaagg caaatgaact    600
atgcgtaatg aacctggtag gcatta                                         626
```

<210> SEQ ID NO 21
<211> LENGTH: 466
<212> TYPE: DNA

<213> ORGANISM: Artificial
<220> FEATURE:
<223> OTHER INFORMATION: Laccase2 delta L

<400> SEQUENCE: 21

```
tcattgagaa atgactgagt tccggtgctc tcaagtcatt gatctttgtc gacttttatt      60
tggtctctgt aataacgact tcaaaaacat taaattctgt tgcgaagcca gtaagctaca    120
aaaagaaaaa acaagagaga atgctatagt cgtatagtat agtttcccga ctatctgata    180
cccattactt atctagggg  aatgcgaacc caaaatttta tcagttttct cggatatcga    240
tagatattgg ggaataaatt taaataaata aattttgggc gggtttaggg cgtggcaaaa    300
agtttttgg  caaatcgcta gaaatttaca agacttataa aattatgaaa aaatacaaca    360
aaatttaaa  cacgtgggcg tgacagtttt ggacggtttt agtataataa taagctaaat    420
cgagactaag ttttattgtt atatatattt tttttatttt atgcag                   466
```

<210> SEQ ID NO 22
<211> LENGTH: 744
<212> TYPE: DNA
<213> ORGANISM: Artificial
<220> FEATURE:
<223> OTHER INFORMATION: Laccase2 delta R

<400> SEQUENCE: 22

```
gtaagtattc aaaagcattt ccgaccatgt aaagtatata tattcttaat aaggatcaat     60
agccgagtcg atctcgccat gtccgtctgt cttattattt tattaccgcc gagacatcag   120
gaactataaa agctagaagg atgagtttta gcatacagat tctagagaca aggacgcaga   180
gcaagtttgt tgatccatgc tgccacgctt taactttctc aaattgccca aaactgccat   240
gcccacattt ttgaactatt ttcgaaattt tttcataatt gtattactcg tgtaaatttc   300
catcaatttg ccaaaaaact ttttgtcacg cgttaacgcc ctaaagccgc caatttggtc   360
acgcccacac tattgaacaa ttatcaaatt ttttctcatt ttattcccca atatctatcg   420
atatccccga ttatgaaatt attaaatttc gcgttcgcat tcacactagc tgagtaacga   480
gtatctgata gttggggaaa tcgacttatt ttttatatac aatgaaaatg aatttaatca   540
tatgaatatc gattatagct ttttatttaa tatgaatatt tatttgggct taaggtgtaa   600
cctcctcgac ataagactca catggcgcag gcacattgaa gacaaaaata ctcattgtcg   660
ggtctcgcac cctccagcag cacctaaaat tatgtcttca attattgcca acattggaga   720
cacaattagt ctgtggcacc tcag                                           744
```

<210> SEQ ID NO 23
<211> LENGTH: 147
<212> TYPE: DNA
<213> ORGANISM: Artificial
<220> FEATURE:
<223> OTHER INFORMATION: EPHB4 delta L

<400> SEQUENCE: 23

```
ccagctactc aggaggctga ggcagaagaa tcattttaac ccgggaggcg gagattgcag     60
tgagccaaga tcgcgccact gcgctccagg cctgggtgac accacggagt taattcccag   120
ctgacggggc cctgcctgat ttctcag                                        147
```

<210> SEQ ID NO 24
<211> LENGTH: 499
<212> TYPE: DNA
<213> ORGANISM: Artificial

<220> FEATURE:
<223> OTHER INFORMATION: EPHB4 delta R

<400> SEQUENCE: 24

```
gtgagcaccg ttcccactta cacccagagg ccacttgggt taagaagcca ggacagacag    60
tgggtcccag gtcacctcct ccagccttt  cctcttgggc taagccctgg tcctctgcct   120
tttctttttt ttaagacaga gcctcgctct gtcgcccagg ctggagtgca gtggcgcgat   180
ctcggctcat tgctgtctcc acctccaggg ttcaagcgat tctcctgcct cagtctccca   240
agtagctggt actataggca tgcaccacca tgctgactaa ttttttgtatt tttagtagac   300
acagggtttc accatgtagg ccaggctggt atcaaactcc tgacctcaag tgatctcccc   360
acctcagcct cccaaagtgc tggtattaca ggtgtgaggc accacgcctg gccagccctc   420
tgcctttaat tttccctctg ggaaaggctg ggctcctggg accttccttt cccactgccc   480
catacagctg aaggttgtc                                                499
```

<210> SEQ ID NO 25
<211> LENGTH: 590
<212> TYPE: DNA
<213> ORGANISM: Encephalomyocarditis virus

<400> SEQUENCE: 25

```
gatccgcccc tctccctccc cccccctaa cgttactggc cgaagccgct tggaataagg    60
ccggtgtgcg tttgtctata tgttattttc caccatattg ccgtctttg  gcaatgtgag   120
ggcccggaaa cctggccctg tcttcttgac gagcattcct aggggtcttt ccctctcgc    180
caaaggaatg caaggtctgt tgaatgtcgt gaaggaagca gttcctctgg aagcttcttg   240
aagacaaaca acgtctgtag cgaccctttg caggcagcgg aaccccccac ctggcgacag   300
gtgcctctgc ggccaaaagc cacgtgtata agatacacct gcaaaggcgg cacaacccca   360
gtgccacgtt gtgagttgga tagttgtgga aagagtcaaa tggctctcct caagcgtatt   420
caacaagggg ctgaaggatg cccagaaggt accccattgt atgggatctg atctgggcc    480
tcggtacaca tgctttacat gtgtttagtc gaggttaaaa aaacgtctag gccccccgaa   540
ccacggggac gtggttttcc tttgaaaaac acgatgataa tatggccaca               590
```

<210> SEQ ID NO 26
<211> LENGTH: 737
<212> TYPE: DNA
<213> ORGANISM: Unknown
<220> FEATURE:
<223> OTHER INFORMATION: poliovirus

<400> SEQUENCE: 26

```
ttaaaacagc tctggggttg ttcccacccc agaggcccac gtggcggcca gtacactggt    60
attgcggtac ctttgtacgc ctgttttata ctcccttccc ccgtaactta gaagcacaat   120
gtccaagttc aataggaggg ggtacaaacc agtaccacca cgaacaagca cttctgttcc   180
cccggtgagg ctgtataggc tgtttccacg gctaaaagcg gctgatccgt tatccgctca   240
tgtacttcga aagcctagt  atcaccttgg aatcttcgat gcgttgcgct caacactcaa   300
ccccagagtg tagcttaggt cgatgagtct ggacgttcct caccgcgac  ggtggtccag   360
gctgcgttgg cggcctacct gtggcccaaa gccacaggac gctagttgtg aacaaggtgt   420
gaagagccta ttgagctacc tgagagtcct ccggccctg  aatgcggcta atcctaacca   480
cggagcaggc agtggcaatc cagcgaccag cctgtcgtaa cgcgcaagtt cgtggcggaa   540
```

```
ccgactactt tgggtgtccg tgtttccttt tatttttaca atggctgctt atggtgacaa     600
tcattgattg ttatcataaa gcaaattgga ttggccatcc ggtgagaatt tgattattaa     660
attactctct tgttgggatt gctcctttga aatcttgtgc actcacacct attggaatta    720
cctcattgtt aagatat                                                    737

<210> SEQ ID NO 27
<211> LENGTH: 580
<212> TYPE: DNA
<213> ORGANISM: Unknown
<220> FEATURE:
<223> OTHER INFORMATION: cytomegalovirus

<400> SEQUENCE: 27
atagtaatca attacggggt cattagttca tagcccatat atggagttcc gcgttacata     60
acttacggta aatggcccgc ctggctgacc gcccaacgac ccccgcccat tgacgtcaat    120
aatgacgtat gttcccatag taacgccaat agggactttc cattgacgtc aatgggtgga    180
gtatttacgg taaactgccc acttggcagt acatcaagtg tatcatatgc caagtacgcc    240
ccctattgac gtcaatgacg gtaaatggcc cgcctggcat tatgcccagt acatgacctt    300
atgggacttt cctacttggc agtacatcta cgtattagtc atcgctatta ccatggtgat    360
gcggttttgg cagtacatca atgggcgtgg atagcggttt gactcacggg gatttccaag    420
tctccacccc attgacgtca atgggagttt gttttggcac caaaatcaac gggactttcc    480
aaaatgtcgt aacaactccg ccccattgac gcaaatgggc ggtaggcgtg tacggtggga    540
ggtctatata agcagagctg gtttagtgaa ccgtcagatc                           580

<210> SEQ ID NO 28
<211> LENGTH: 229
<212> TYPE: DNA
<213> ORGANISM: Simian virus 40

<400> SEQUENCE: 28
tgatcataat cagccatacc acatttgtag aggttttact tgctttaaaa aacctcccac     60
acctccccct gaacctgaaa cataaaatga atgcaattgt tgttgttaac ttgtttattg    120
cagcttataa tggttacaaa taaagcaata gcatcacaaa tttcacaaat aaagcatttt    180
tttcactgca ttctagttgt ggtttgtcca aactcatcaa tgtatctta                 229

<210> SEQ ID NO 29
<211> LENGTH: 199
<212> TYPE: DNA
<213> ORGANISM: Artificial
<220> FEATURE:
<223> OTHER INFORMATION: EPHB4 left

<400> SEQUENCE: 29
ccagctactc aggaggctga ggcagaagaa tcattttaac ccgggaggcg gagattgcag     60
tgagccaaga tcgcgccact gcgctccagg cctgggtgac accacggaga caggggtttg    120
gggctaaaag ctatgagccg agcctccgag tccagtggga gttaattccc agctgacggg    180
gccctgcctg atttctcag                                                  199

<210> SEQ ID NO 30
<211> LENGTH: 525
<212> TYPE: DNA
<213> ORGANISM: Artificial
<220> FEATURE:
<223> OTHER INFORMATION: EPHB4 right
```

<400> SEQUENCE: 30

```
gtgagcaccc tccctggctt ctgcggccac ccggagttcc cacttacacc cagaggccac    60
ttgggttaag aagccaggac agacagtggg tcccaggtca cctcctccag ccttttcctc   120
ttgggctaag ccctggtcct ctgccttttc ttttttttaa gacagagcct cgctctgtcg   180
cccaggctgg agtgcagtgg cgcgatctcg gctcattgct gtctccacct ccagggttca   240
agcgattctc ctgcctcagt ctcccaagta gctggtacta taggcatgca ccaccatgct   300
gactaatttt tgtatttta gtagacacag ggtttcacca tgtaggccag ctggtatca   360
aactcctgac ctcaagtgat ctccccacct cagcctccca aagtgctggt attacaggtg   420
tgaggcacca cgcctggcca gccctctgcc tttaattttc cctctgggaa aggctgggct   480
cctgggaccc tcctttccca ctgccccata cagctgaagg ttgtc              525
```

<210> SEQ ID NO 31
<211> LENGTH: 608
<212> TYPE: DNA
<213> ORGANISM: Artificial
<220> FEATURE:
<223> OTHER INFORMATION: Laccase2 left

<400> SEQUENCE: 31

```
tcattgagaa atgactgagt tccggtgctc tcaagtcatt gatctttgtc gactttatt    60
tggtctctgt aataacgact tcaaaaacat taaattctgt tgcgaagcca gtaagctaca   120
aaaagaaaaa acaagagaga atgctatagt cgtatagtat agtttcccga ctatctgata   180
cccattactt atctagggg aatgcgaacc caaaatttta tcagttttct cggatatcga   240
tagatattgg ggaataaatt taaataaata aattttgggc gggtttaggg cgtggcaaaa   300
agttttttgg caaatcgcta gaaatttaca agacttataa aattatgaaa aaatacaaca   360
aaattttaaa cacgtgggcg tgacagtttt ggacggtttt agggcgttag agtaggcgag   420
gacagggtta catcgactag gctttgatcc tgatcaagaa tatatatact ttataccgct   480
tccttctaca tgttacctat ttttcaacga atctagtata ccttttact gtacgattta   540
tgggtataat aataagctaa atcgagacta agttttattg ttatatatat tttttttatt   600
ttatgcag                                                            608
```

<210> SEQ ID NO 32
<211> LENGTH: 848
<212> TYPE: DNA
<213> ORGANISM: Artificial
<220> FEATURE:
<223> OTHER INFORMATION: Laccase2 right

<400> SEQUENCE: 32

```
gtaagtattc aaaattccaa aatttttac tagaaatatt cgattttta ataggcagtt    60
tctatactat tgtatactat tgtagattcg ttgaaagta tgtaacagga agaataaagc   120
atttccgacc atgtaaagta tatatattct taataaggat caatagccga gtcgatctcg   180
ccatgtccgt ctgtcttatt attttattac cgccgagaca tcaggaacta taaaagctag   240
aaggatgagt tttagcatac agattctaga gacaaggacg cagagcaagt tgttgatcc   300
atgctgccac gctttaactt tctcaaattg cccaaaactg ccatgccac atttttgaac   360
tattttcgaa attttttcat aattgtatta ctcgtgtaaa tttccatcaa tttgccaaaa   420
aacttttgt cacgcgttaa cgccctaaag ccgccaattt ggtcacgccc acactattga   480
```

```
acaattatca aatttttct cattttattc cccaatatct atcgatatcc ccgattatga        540
aattattaaa tttcgcgttc gcattcacac tagctgagta acgagtatct gatagttggg        600
gaaatcgact tattttttat atacaatgaa aatgaattta atcatatgaa tatcgattat        660
agctttttat ttaatatgaa tatttatttg ggcttaaggt gtaacctcct cgacataaga        720
ctcacatggc gcaggcacat tgaagacaaa aatactcatt gtcgggtctc gcaccctcca        780
gcagcaccta aaattatgtc ttcaattatt gccaacattg gagacacaat tagtctgtgg        840
cacctcag                                                                848
```